United States Patent [19]

Onoda et al.

[11] Patent Number: 5,698,560

[45] Date of Patent: Dec. 16, 1997

[54] IMIDAZOQUINAZOLINE DERIVATIVES

[75] Inventors: Yasuo Onoda; Shin-ichi Sasaki, both of Sunto-gun; Daisuke Machii, Naka-gun; Haruki Takai, Yokohama; Tetsuji Ohno, Sunto-gun; Koji Yamada, Sagamihara; Michio Ichimura, Mishima; Hiroshi Kase, Koganei, all of Japan

[73] Assignee: Kyowa Hakko Kogyo Co., Ltd., Tokyo, Japan

[21] Appl. No.: 727,598

[22] PCT Filed: Mar. 1, 1996

[86] PCT No.: PCT/JP96/00497

§ 371 Date: Oct. 23, 1996

§ 102(e) Date: Oct. 23, 1996

[87] PCT Pub. No.: WO96/26940

PCT Pub. Date: Sep. 6, 1996

[30] Foreign Application Priority Data

Mar. 1, 1995 [JP] Japan .................................. 7-041606

[51] Int. Cl.$^6$ .................. A61K 31/505; A61K 31/535; C07D 487/02; C07D 417/02
[52] U.S. Cl. .................. 514/267; 514/228.5; 514/232.8; 514/248; 514/253; 544/60; 544/115; 544/237; 544/238; 544/251
[58] Field of Search .................. 544/60, 115, 237, 544/238, 251; 514/228.5, 232.8, 248, 253, 267

[56] References Cited

FOREIGN PATENT DOCUMENTS

| | | |
|---|---|---|
| 0635507 | 1/1995 | European Pat. Off. . |
| 0668280 | 8/1995 | European Pat. Off. . |
| 7-53556 | 2/1995 | Japan . |

OTHER PUBLICATIONS

Schneller et al., J. Med. Chem., vol. 29, No. 6 (1986) 972–78.
Schneller et al., J. Med. Chem., vol. 32, No. 10 (1989) 2247–54.
Stevenson et al., J. Org. Chem., vol. 51, No. 5 (1986) 616–20.

*Primary Examiner*—Mukund J. Shah
*Assistant Examiner*—Brenda Coleman
*Attorney, Agent, or Firm*—Fitzpatrick, Cella, Harper & Scinto

[57] ABSTRACT

The present invention relates to imidazoquinazoline derivatives represented by formula (I):

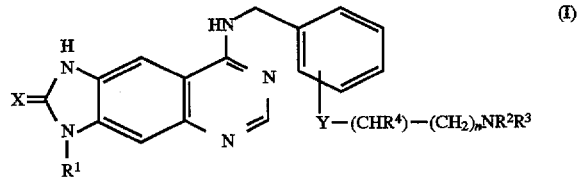

wherein $R^1$ represents hydrogen, substituted or unsubstituted lower alkyl, cycloalkyl, lower alkenyl, substituted or unsubstituted aralkyl, substituted or unsubstituted aryl, substituted or unsubstituted heteroarylalkyl, or substituted or unsubstituted heteroaryl, $R^2$ and $R^3$ represent independently hydrogen, substituted or unsubstituted lower alkyl, substituted or unsubstituted aralkyl, substituted or unsubstituted aryl, substituted or unsubstituted heteroarylalkyl, or substituted or unsubstituted heteroaryl, or $R^2$ and $R^3$ are combined to represent a heterocyclic group containing a nitrogen atom, $R^4$ represents hydrogen or substituted or unsubstituted lower alkyl, X represents O or S, Y represents a single bond or O, n represents 0, 1, 2, or 3, and pharmaceutically acceptable salts thereof.

5 Claims, No Drawings

IMIDAZOQUINAZOLINE DERIVATIVES

This application is a 371 of PCT/JP96/60497, filed Mar. 1, 1996.

1. Technical Field

The present invention relates to imidazoquinazoline derivatives or pharmaceutically acceptable salts thereof which have the cyclic guanosine 3',5'-monophosphate (cGMP)-specific phosphodiesterase (PDE) inhibitory activity and are useful for treating or ameliorating cardiovascular diseases such as thrombosis, angina pectoris, hypertension, heart failure, arterial sclerosis, as well as asthma and the like.

2. Background Art cGMP plays an important role as a second messenger in intracellular signal transduction. An inhibitor of cGMP-specific PDE, an enzyme which degrades cGMP, increases the concentration of intracellular cGMP, enhances the effects of endothelium-derived relaxing factor (EDRF), nitro vasodilator or atrial natriuretic peptide, shows the antiplatelet activity, the anti-vasocontraction activity and the vasodilating activity, and are useful for treating angina pectoris, hypertension, congestive heart failure, post-PTCA restenosis, peripheral vascular diseases, bronchitis, chronic asthma, allergic asthma, allergic gravedo, glaucoma, alimentary canal diseases such as irritable intestine syndrome, and the like.

The PDE inhibitory activity and the adenosine receptor antagonistic activity of imidazo [4,5-g]quinazoline derivatives are described in J. Med. Chem., 29, 972 (1986), J. Med. Chem., 32, 2247 (1989), J. Org. Chem., 51, 616 (1986) and the references cited therein. However, these compounds are neither particularly strong PDE inhibitors nor selective cGMP-specific PDE inhibitors.

Further, 8-anilino-2,3-dihydro-1H-imidazo[4,5-g]quinazolin-2-one deivatives are disclosed in EP635507.

The PDE inhibitors known so far inhibit not only cGMP-specific PDE but also the cyclic adenosine 3',5'-monophosphate (cAMP) PDE which is an enzyme similar thereto, and therefore cause the elevation of the concentration of cAMP as well as intracellular cGMP and may cause side effects and the like. Further, the inhibitory activities thereof are not yet sufficient, and compounds which are more potent and selective are expected and desired.

DISCLOSURE OF THE INVENTION

The present invention relates to imidazoquinazoline derivatives [hereinafter referred to as Compound (I); the same applies to the compounds of other formula numbers] represented by formula (I):

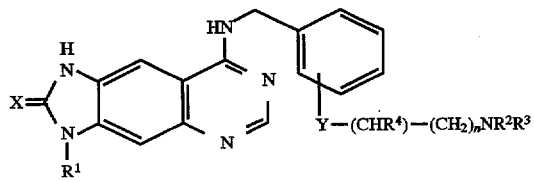

wherein $R^1$ represents hydrogen, substituted or unsubstituted lower alkyl, cycloalkyl, lower alkenyl, substituted or unsubstituted aralkyl, substituted or unsubstituted aryl, substituted or unsubstituted heteroarylalkyl, or substituted or unsubstituted heteroaryl, $R^2$ and $R^3$ represent independently hydrogen, substituted or unsubstituted lower alkyl, substituted or unsubstituted aralkyl, substituted or unsubstituted aryl, substituted or unsubstituted heteroarylalkyl, or substituted or unsubstituted heteroaryl, or $R^2$ and $R^3$ are combined to represent a substituted or unsubstituted heterocyclic group containing a nitrogen atom, $R^4$ represents hydrogen or substituted or unsubstituted lower alkyl, X represents O or S, Y represents a single bond or O, n represents 0, 1, 2, or 3, or pharmaceutically acceptable salts thereof.

In the definitions of the groups of formula (I), the lower alkyl means a straight-chain or branched alkyl group having 1 to 8 carbon atoms, such as methyl, ethyl, propyl, isopropyl, butyl, isobutyl, sec-butyl, tert-butyl, pentyl, isopentyl, neopentyl, sec-pentyl, hexyl, isohexyl, heptyl, octyl, and isooctyl. The cycloalkyl means a cycloalkyl group having 3 to 8 carbon atoms, such as cyclopropyl, cyclobutyl, cyclopentyl, cyclohexyl, cycloheptyl, and cyclooctyl. The lower alkenyl means a straight-chain or branched alkenyl group having 2 to 6 carbon atoms, such as vinyl, allyl, propenyl, methacryl, butenyl, crotyl, pentenyl, and hexenyl. The aralkyl means an aralkyl group having 7 to 15 carbon atoms, such as benzyl, phenethyl, benzhydryl, and naphthylmethyl. The aryl means phenyl and naphthyl, and the heteroaryl means pyridyl, pyrazinyl, pyrimidinyl, pyridazinyl, quinolyl, isoquinolyl, phthalazinyl, quinazolinyl, quinoxalinyl, naphthyridinyl, thienyl, furyl, pyrrolyl, imidazolyl, pyrazolyl, oxazolyl, thiazolyl, triazolyl, tetrazolyl, benzothienyl, benzofuryl, indolyl, indazolyl, benzimidazoyl, benzotriazolyl, purinyl, and the like. The heterocyclic group containing a nitrogen atom means pyrrolidinyl, piperidino, piperazinyl, morpholino, thiomorpholino, homopiperidinyl, homopiperazinyl, tetrahydropyridinyl, and the like. The alkyl moiety and heteroaryl moiety of the heteroarylalkyl have the same meanings as the above-defined lower alkyl and above-defined heteroaryl, respectively.

The substituted lower alkyl has the same or different 1 to 3 substituents such as cycloalkyl, hydroxy, lower alkoxy, carboxy, lower alkoxycarbonyl, amino, monoalkyl-substituted amino, dialkyl-substituted amino, nitro, halogen, or substituted or unsubstituted alicyclic heterocyclic group. Examples of the alicyclic heterocyclic group are tetrahydrofuranyl, tetrahydropyranyl, piperidino, piperidinyl, piperazinyl, homopiperazinyl, morpholino, morpholinyl, thiomorpholinyl, thiomorpholino, pyrrolidinyl, and the like. The halogen includes fluorine, chlorine, bromide and iodine. The alkyl moiety of the lower alkoxy, lower alkoxycarbonyl, monoalkyl-substituted amino, and dialkyl-substituted amino has the same meaning as the lower alkyl defined above, and the cycloalkyl has the same meaning as the cycloalkyl defined above. The substituted alicyclic heterocyclic group has the same or different 1 to 3 substituents such as lower alkyl, aralkyl, aryl, heteroarylalkyl, or heteroaryl, and the lower alkyl, aralkyl, aryl, heteroarylalkyl, and heteroaryl have the same meanings as defined above, respectively.

The substituted aralkyl, substituted aryl, substituted heteroarylalkyl, and substituted heteroaryl each has the same or different 1 to 5 substituents such as lower alkyl, hydroxy, lower alkoxy, carboxy, lower alkoxycarbonyl, amino, monoalkyl-substituted amino, dialkyl-substituted amino, nitro, sulfonamido, halogen, trifluoromethyl, or the like. The lower alkyl and the alkyl moiety of the lower alkoxy, lower alkoxycarbonyl, monoalkyl-substituted amino, dialkyl-substituted amino have the same meaning as the lower alkyl defined above, and the halogen has the same meaning as the halogen defined above.

The substituted heterocyclic group containing a nitrogen atom has the same or different 1 to 3 substituents such as substituted or unsubstituted lower alkyl, substituted or unsubstituted aralkyl, substituted or unsubstituted aryl, hydroxy, lower alkoxy, carboxy, lower alkoxycarbonyl, lower alkanoyl, amino, monoalkyl-substituted amino, dialkyl-substituted amino, nitro, sulfonamido, halogen, trifluoromethyl, oxo, heteroarylalkyl, heteroaryl, or the like. The lower alkanoyl means a straight-chain or branched alkanoyl group having 1 to 8 carbon atoms, such as formyl, acetyl, propionyl, butyryl, isobutyryl, valeryl, pivaloyl, hexanoyl, heptanoyl, and octanoyl, and the lower alkyl, aralkyl, aryl, lower alkoxy, lower alkoxycarbonyl, monoalkyl-substituted amino, dialkyl-substituted amino, halogen, heteroarylalkyl, and heteroaryl have the same meanings as defined above, respectively. The substituted lower alkyl has the same or different 1 to 3 substituents such as hydroxy, hydroxy-substituted or unsubstituted lower alkoxy, carbamoyl, or alkylcarbamoyl, the lower alkoxy has the same meaning as defined above, and the alkyl moiety of the alkylcarbamoyl has the same meaning as the lower alkyl defined above. The substituted aryl and substituted aralkyl each has the same or different 1 to 3 substituents such as hydroxy, lower alkoxy, halogen, methylenedioxy, or the like, and the lower alkoxy and halogen have the same meanings as defined above, respectively.

The pharmaceutically acceptable salts of Compounds (I) include acid addition salts, for example, inorganic acid addition salts such as hydrochloride, hydrobromide, hydroiodide, nitrate, sulfate, phosphate, and the like, and organic acid addition salts such as formate, acetate, benzoate, tartrate, maleate, fumarate, succinate, oxalate, glyoxylate, aspartate, methanesulfonate, benzenesulfonate, and the like.

Then, a process for preparing Compound (I) is described below.

Process 1:

Compound (Ia) wherein X is O

Compound (Ia) can be prepared according to the following reaction steps.

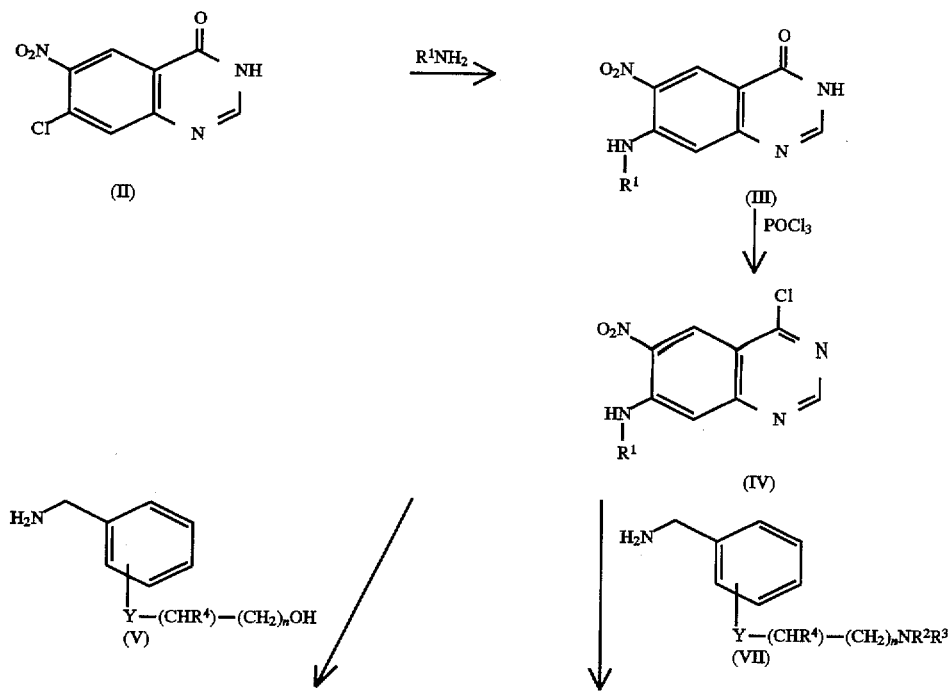

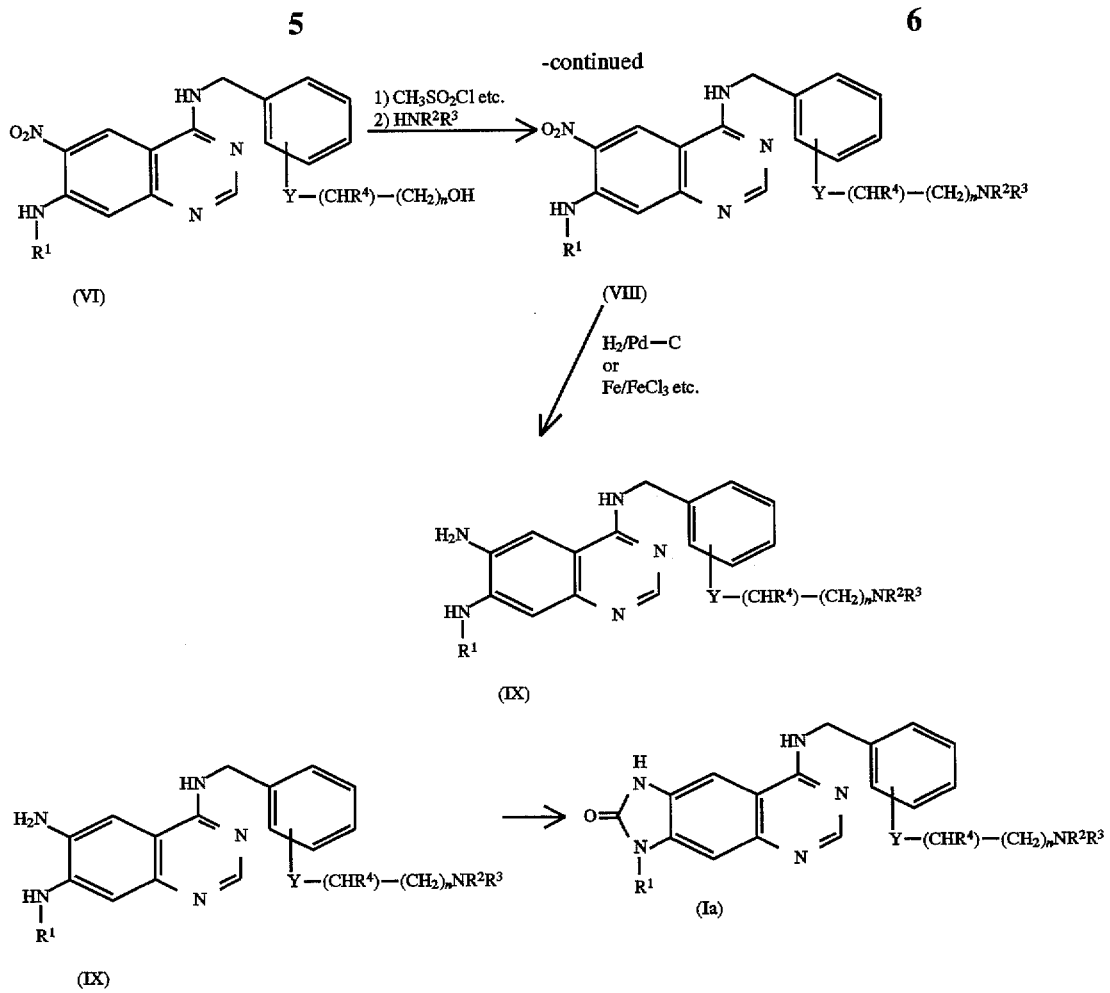

(In the formulae, $R^1$, $R^2$, $R^3$, $R^4$, Y, and n have the same meanings as defined above.)

Starting Compound (II) can be obtained according to the known process [J. Org. Chem., 40, 356 (1975), etc.].

Compound (III) can be obtained by reacting Compound (II) with one equivalent to an excess amount of an amine represented by the formula $R^1NH_2$ (wherein $R^1$ has the same meaning as defined above) or an aqueous solution thereof, in a solvent such as ethanol, or butanol, if necessary, using a sealed container (in a sealed tube), at a temperature between room temperature and 150° C. for 1 to 24 hours.

Compound (IV) can be obtained by reacting Compound (III) with a chlorinating agent such as phosphorus oxychloride, preferably in the presence of an organic base such as triethylamine, without a solvent or in a sovent such as 1,2-dichloroethane at a temperature between room temperature and the boiling point of the chlorinating agent employed for 1 to 24 hours.

Compound (VI) can be obtained by reacting Compound (IV) with one equivalent to an excess amount of Compound (V), preferably in the presence of an organic base such as triethylamine, in a solvent such as tetrahydrofuran at a temperature between room temperature and the boiling point of the solvent employed for 1 to 24 hours. Starting Compound (V) can be obtained according to the processes described in Reference Examples or similar methods thereto.

Compound (VIII) can be obtained by converting a hydroxyl group of Compound (VI) into an appropriate leaving group and reacting the resulting product with an amine represented by the formula $R^2R^3NH$ (wherein $R^2$ and $R^3$ have the same meanings as defined above) in the presence of not less than one equivalent of 2,6-lutidine or the like in a solvent such as N,N-dimethylformamide or 1,2-dichloroethane at a temperature between room temperature and the boiling point of the solvent employed for 1 to 24 hours. The conversion of the hydroxyl group of Compound (VI) into the leaving group can be carried out, for example, by reacting Compound (VI) with 1 to 5 equivalents of methanesulfonyl chloride in the presence of not less than one equivalent of 2,6-lutidine or the like in a solvent such as N,N-dimethylformamide or 1,2-dichloroethane at a temperature between room temperature and the boiling point of the solvent employed for 1 to 24 hours.

Compound (VIII) can also be directly obtained by reacting Compound (IV) with Compound (VII), preferably in the presence of an organic base such as triethylamine, in a solvent such as tetrahydrofuran at a temperature between room temperature and the boiling point of the solvent employed for 1 to 24 hours. Starting Compound (VII) can be obtained according to the processes described in Reference Examples or similar methods thereto.

Alternatively, Compound (VI) and Compound (VIII) can be obtained by reacting Compound (II) with a chlorinating agent such as phosphorus oxychloride or the like, and reacting the resulting product with Compound (V) or Compound (VII), followed by reaction with an amine represented by the formula $R^1NH_2$ (wherein $R^1$ has the same meaning as defined above) or an aqueous solution thereof, by changing the order of the above reactions.

Compound (IX) can be obtained by catalytic reduction of Compound (VIII) in the presence of a catalyst such as palladium on carbon in a solvent such as tetrahydrofuran, ethanol, or N,N-dimethylformamide under hydrogen atmosphere, or in the presence of a reducing agent such as iron or ferric chloride in a solvent such as ethanol or water, at a temperature between room temperature and the boiling point of the solvent employed.

Compound (Ia) can be obtained by cyclization of Compound (IX) using not less than one equivalent of N,N'-carbonyldiimidazole, phosgene, or the like, if necessary, in the presence of a base, in an inert solvent. The examples of the base are triethylamine, pyridine, and the like. The examples of the inert solvent are water, alcohols (methanol, ethanol, and the like), non-polar solvents (ethyl acetate, ether, and the like), aprotic polar solvents (acetonitrile, dimethylformamide, dimethyl sulfoxide, tetrahydrofuran, dioxane, and the like), and halogenated hydrocarbons (dichloromethane, chloroform, and the like). The reaction is carried out at a temperature between 0° C. and the boiling point of the solvent employed and is completed in 10 minutes to 48 hours.

Process 2:

Compound (Ib) wherein X is S

Compound (Ib) can be prepared according to the following reaction step:

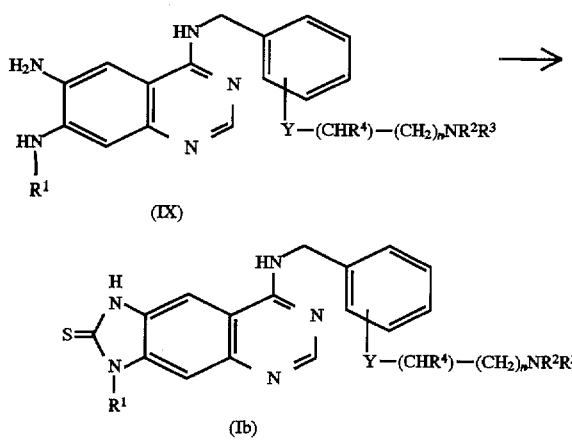

(In the formulae, $R^1$, $R^2$, $R^3$, $R^4$, Y, and n have the same meanings as defined above.)

Compound (Ib) can be obtained by cyclization of Compound (IX) using not less than one equivalent of N,N'-thiocarbonyldiimidazole, carbon disulfide, thiophosgene, or the like, if necessary, in the presence of a base, in an inert solvent. The examples of the base and inert solvent are the same as those described for preparation of Compound (Ia). The reaction is carried out at a temperature between 0° C. and the boiling point of the solvent employed and is completed in 10 minutes to 48 hours.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without purification.

Among Compounds (I), some may have a tautomer.

The present invention includes all possible isomers including tautomers and mixtures thereof.

In the case where a salt of Compound (I) is desired and it is produced in the form of the desired salt, it can be subjected to purification as such. In the case where Compound (I) is produced in the free form and its salt is desired, Compound (I) is dissolved or suspended in a suitable solvent, followed by addition of an acid to form a salt, which may be isolated and purified.

Compounds (I) and pharmaceutically acceptable salts thereof may be in the form of adducts with water or various solvents, which are also within the scope of the present invention.

The examples of Compound (I) obtained in the present invention are shown in Table 1.

TABLE 1-1

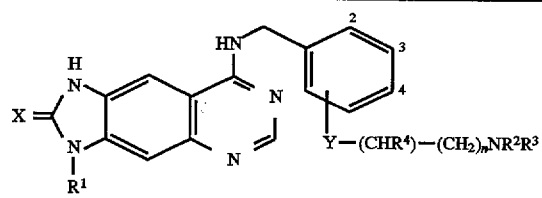

| Compd. No. | X | $R^1$ | position of substitution (2,3,4) | Y | n | $R^2$ | $R^3$ | $R^4$ |
|---|---|---|---|---|---|---|---|---|
| 1 | O | $C_2H_5$ | 2 | — | 0 | $-(CH_2)_2-O-(CH_2)_2-$ | | H |
| 2 | O | $C_2H_5$ | 3 | — | 0 | $-(CH_2)_2-O-(CH_2)_2-$ | | H |
| 3 | O | $C_2H_5$ | 4 | — | 0 | $-(CH_2)_5-$ | | H |
| 4 | S | $C_2H_5$ | 2 | — | 0 | $-(CH_2)_2-O-(CH_2)_2-$ | | H |
| 5 | S | $C_2H_5$ | 2 | — | 0 | $-(CH_2)_5-$ | | H |
| 6 | S | $C_2H_5$ | 2 | — | 0 | $C_2H_5$ | $C_2H_5$ | H |

TABLE 1-1-continued

[Structure: benzimidazole with X=, N-R¹, connected to -C(=N...)NH-CH₂-phenyl(2,3,4 positions) and N=CH-N ring with Y—(CHR⁴)—(CH₂)ₙNR²R³]

| Compd. No. | X | R¹ | position of substitution (2,3,4) | Y | n | R² | R³ | R⁴ |
|---|---|---|---|---|---|---|---|---|
| 7 | S | C₂H₅ | 2 | — | 0 | —(CH₂)₂—N(CH₃)—(CH₂)₂— | | H |
| 8 | S | C₂H₅ | 2 | — | 0 | —(CH₂)₂—N(CH₂C₆H₅)—(CH₂)₂— | | H |
| 9 | S | C₂H₅ | 2 | — | 0 | —(CH₂)₂—N(2-pyridyl)—(CH₂)₂— | | H |
| 10 | S | C₂H₅ | 2 | — | 0 | H | CH₂-(2-pyridyl) | H |

TABLE 1-2

[Same structure as above]

| Compd. No. | X | R¹ | position of substitution (2,3,4) | Y | n | R² | R³ | R⁴ |
|---|---|---|---|---|---|---|---|---|
| 11 | S | C₂H₅ | 2 | — | 0 | —(CH₂)₂—O—(CH₂)₂— | | CH₃ |
| 12 | S | C₂H₅ | 2 | — | 0 | —(CH₂)₂—N(CH₃)—(CH₂)₂— | | CH₃ |
| 13 | S | C₂H₅ | 3 | — | 0 | —(CH₂)₂—O—(CH₂)₂— | | H |
| 14 | S | C₂H₅ | 4 | — | 0 | —(CH₂)₂—O—(CH₂)₂— | | H |
| 15 | S | C₂H₅ | 4 | — | 0 | —(CH₂)₅— | | H |
| 16 | S | C₂H₅ | 4 | — | 0 | —(CH₂)₂—N(CH₃)—(CH₂)₂— | | H |
| 17 | S | C₂H₅ | 4 | — | 0 | H | (CH₂)₃CH₃ | H |
| 18 | S | C₂H₅ | 4 | — | 0 | H | (CH₂)₂CH₃ | H |
| 19 | S | C₂H₅ | 4 | — | 0 | H | CH₂-(2-pyridyl) | H |
| 20 | S | C₂H₅ | 4 | — | 0 | —(CH₂)₄— | | H |

TABEL 1-3

| Compd. No. | X | R¹ | position of substitution (2,3,4) | Y | n | R² | R³ | R⁴ |
|---|---|---|---|---|---|---|---|---|
| 21 | O | $C_2H_5$ | 2 | O | 1 | $-(CH_2)_2-O-(CH_2)_2-$ | | H |
| 22 | O | $C_2H_5$ | 2 | O | 1 | $-(CH_2)_5-$ | | H |
| 23 | O | $C_2H_5$ | 2 | O | 1 | $C_2H_5$ | $C_2H_5$ | H |
| 24 | O | $C_2H_5$ | 2 | O | 1 | $-(CH_2)_2-N(CH_3)-(CH_2)_2-$ | | H |
| 25 | O | $C_2H_5$ | 3 | O | 2 | $CH_3$ | $CH_3$ | H |
| 26 | O | $C_2H_5$ | 4 | O | 2 | $CH_3$ | $CH_3$ | H |
| 27 | O | $C_2H_5$ | 2 | O | 3 | $-(CH_2)_2-O-(CH_2)_2-$ | | H |
| 28 | O | $C_2H_5$ | 2 | O | 3 | $-(CH_2)_5-$ | | H |
| 29 | S | $C_2H_5$ | 2 | O | 1 | $-(CH_2)_2-O-(CH_2)_2-$ | | H |
| 30 | S | $C_2H_5$ | 2 | O | 1 | $-(CH_2)_5-$ | | H |

TABLE 1-4

| Compd. No. | X | R¹ | position of substitution (2,3,4) | Y | n | R² | R³ | R⁴ |
|---|---|---|---|---|---|---|---|---|
| 31 | S | $C_2H_5$ | 2 | O | 1 | $C_2H_5$ | $C_2H_5$ | H |
| 32 | S | $C_2H_5$ | 2 | O | 1 | $-(CH_2)_2-N(CH_3)-(CH_2)_2-$ | | H |
| 33 | S | $C_2H_5$ | 2 | O | 2 | $CH_3$ | $CH_3$ | H |
| 34 | S | $C_2H_5$ | 2 | O | 2 | $-(CH_2)_2-O-(CH_2)_2-$ | | H |
| 35 | S | $C_2H_5$ | 2 | O | 1 | $-(CH_2)_2-O-(CH_2)_2-$ | | $CH_3$ |
| 36 | S | $C_2H_5$ | 2 | O | 3 | $-(CH_2)_2-O-(CH_2)_2-$ | | H |
| 37 | S | $C_2H_5$ | 2 | O | 3 | $-(CH_2)_5-$ | | H |
| 38 | S | $C_2H_5$ | 3 | O | 1 | $-(CH_2)_2-O-(CH_2)_2-$ | | H |
| 39 | S | $C_2H_5$ | 3 | O | 1 | $-(CH_2)_5-$ | | H |
| 40 | S | $C_2H_5$ | 3 | O | 1 | $C_2H_5$ | $C_2H_5$ | H |

TABLE 1-5

| Compd. No. | X | R¹ | position of substitution (2,3,4) | Y | n | R² | R³ | R⁴ |
|---|---|---|---|---|---|---|---|---|
| 41 | S | $C_2H_5$ | 3 | O | 2 | $CH_3$ | $CH_3$ | H |
| 42 | S | $C_2H_5$ | 4 | O | 1 | $-(CH_2)_2-O-(CH_2)_2-$ | | H |
| 43 | S | $C_2H_5$ | 4 | O | 2 | $CH_3$ | $CH_3$ | H |
| 44 | S | $C_2H_5$ | 2 | — | 0 | $-(CH_2)_2-N-(CH_2)_2-$ (N-phenyl) | | H |
| 45 | S | $C_2H_5$ | 2 | — | 0 | $-(CH_2)_2-N-(CH_2)_2-$ (N-(2-Cl-phenyl)) | | H |
| 46 | S | $C_2H_5$ | 2 | — | 0 | $-(CH_2)_2-N-(CH_2)_2-$ (N-(2-OCH₃-phenyl)) | | H |
| 47 | S | $C_2H_5$ | 2 | — | 0 | $-(CH_2)_4-$ | | H |
| 48 | S | $C_2H_5$ | 2 | — | 0 | $-(CH_2)_2-N(CH_2CH_3)-(CH_2)_2-$ | | H |
| 49 | S | $C_2H_5$ | 2 | — | 0 | $CH_2CH_2OH$ | $CH_2CH_2OH$ | H |
| 50 | S | $C_2H_5$ | 2 | — | 0 | $-(CH_2)_2-N(CH_3)-(CH_2)_3-$ | | H |

TABLE 1-6

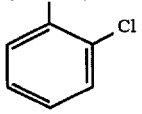

| Compd. No. | X | R¹ | position of substitution (2,3,4) | Y | n | R² | R³ | R⁴ |
|---|---|---|---|---|---|---|---|---|
| 51 | S | $C_2H_5$ | 2 | — | 0 | $-(CH_2)_6-$ | | H |
| 52 | S | $C_2H_5$ | 2 | — | 0 | H | $(CH_2)_3CH_3$ | H |
| 53 | O | $C_2H_5$ | 2 | — | 0 | $-(CH_2)_2-N(CH_3)-(CH_2)_3-$ | | H |
| 54 | S | $C_2H_5$ | 4 | — | 0 | $C_2H_5$ | $C_2H_5$ | H |
| 55 | O | $C_2H_5$ | 4 | — | 0 | $C_2H_5$ | $C_2H_5$ | H |

TABLE 1-6-continued

[Structure: benzimidazolone with X=, R¹, HN-CH-phenyl(2,3,4)-Y-(CHR⁴)-(CH₂)ₙNR²R³, with N=CH-N substituent]

| Compd. No. | X | R¹ | position of substitution (2,3,4) | Y | n | R² | R³ | R⁴ |
|---|---|---|---|---|---|---|---|---|
| 56 | O | $C_2H_5$ | 4 | — | 0 | $-(CH_2)_2-N(CH_3)-(CH_2)_2-$ | | H |
| 57 | S | $C_2H_5$ | 2 | O | 2 | $-(CH_2)_5-$ | | H |
| 58 | S | $C_2H_5$ | 2 | O | 2 | $C_2H_5$ | $C_2H_5$ | H |
| 59 | O | $C_2H_5$ | 2 | O | 2 | $-(CH_2)_5-$ | | H |
| 60 | O | $C_2H_5$ | 2 | O | 2 | $CH_3$ | $CH_3$ | H |

TABLE 1-7

[Structure: benzimidazolone with X=, R¹, HN-CH-phenyl(2,3,4)-Y-(CHR⁴)-(CH₂)ₙNR²R³, with N=CH-N substituent]

| Compd. No. | X | R¹ | position of substitution (2,3,4) | Y | n | R² | R³ | R⁴ |
|---|---|---|---|---|---|---|---|---|
| 61 | O | $C_2H_5$ | 2 | O | 2 | $-(CH_2)_2-O-(CH_2)_2-$ | | H |
| 62 | S | $C_2H_5$ | 4 | O | 1 | $C_2H_5$ | $C_2H_5$ | H |
| 63 | S | $C_2H_5$ | 4 | O | 1 | $-(CH_2)_5-$ | | H |
| 64 | S | $C_2H_5$ | 4 | O | 1 | $-(CH_2)_2-N(CH_3)-(CH_2)_2-$ | | H |
| 65 | S | $C_2H_5$ | 4 | O | 1 | $-(CH_2)_2-N(CH_2CH_3)-(CH_2)_2-$ | | H |
| 66 | S | $C_2H_5$ | 4 | O | 1 | $-(CH_2)_2-N(CH_2CH_2OH)-(CH_2)_2-$ | | H |
| 67 | S | $C_2H_5$ | 4 | O | 1 | $-(CH_2)_4-$ | | H |
| 68 | S | $C_2H_5$ | 4 | O | 2 | $C_2H_5$ | $C_2H_5$ | H |
| 69 | S | $C_2H_5$ | 4 | O | 3 | $C_2H_5$ | $C_2H_5$ | H |
| 70 | O | $C_2H_5$ | 4 | O | 1 | $C_2H_5$ | $C_2H_5$ | H |

TABLE 1-8

| Compd. No. | X | $R^1$ | position of substitution (2,3,4) | Y | n | $R^2$ | $R^3$ | $R^4$ |
|---|---|---|---|---|---|---|---|---|
| 71 | S | $C_2H_5$ | 2 | — | 0 | $-CH_2-CH=CH-(CH_2)_2-$ | | H |
| 72 | S | $C_2H_5$ | 2 | — | 0 | $-(CH_2)_2-N(CH_2CH_2OCH_2CH_2OH)-(CH_2)_2-$ | | H |
| 73 | S | $C_2H_5$ | 2 | — | 0 | $-(CH_2)_2-N(CH_2CONHCH(CH_3)_2)-(CH_2)_2-$ | | H |
| 74 | S | $C_2H_5$ | 2 | — | 0 | $-(CH_2)_2-N(CH_2\text{-(benzo[1,3]dioxol-5-yl)})-(CH_2)_2-$ | | H |
| 75 | S | $C_2H_5$ | 2 | — | 0 | $-(CH_2)_2-CH(CO_2C_2H_5)-(CH_2)_2-$ | | H |
| 76 | O | $C_2H_5$ | 2 | — | 0 | $-(CH_2)_2-CH(CO_2C_2H_5)-(CH_2)_2-$ | | H |
| 77 | O | $C_2H_5$ | 2 | — | 0 | $-(CH_2)_2-N(\text{2-pyridyl})-(CH_2)_2-$ | | H |
| 78 | O | $C_2H_5$ | 2 | O | 2 | $C_2H_5$ | $C_2H_5$ | H |
| 79 | S | $C_2H_5$ | 3 | O | 2 | $-(CH_2)_2-O-(CH_2)_2-$ | | H |
| 80 | S | $C_2H_5$ | 3 | O | 2 | $C_2H_5$ | $C_2H_5$ | H |

TABLE 1-9

| Compd. No. | X | $R^1$ | position of substitution (2,3,4) | Y | n | $R^2$ | $R^3$ | $R^4$ |
|---|---|---|---|---|---|---|---|---|
| 81 | O | $C_2H_5$ | 3 | O | 2 | $-(CH_2)_2-O-(CH_2)_2-$ | | H |
| 82 | S | $C_2H_5$ | 4 | O | 2 | $-(CH_2)_2-O-(CH_2)_2-$ | | H |
| 83 | S | $C_2H_5$ | 4 | O | 3 | $-(CH_2)_2-O-(CH_2)_2-$ | | H |
| 84 | S | $C_2H_5$ | 4 | O | 3 | $C_2H_5$ | $C_2H_5$ | H |
| 85 | O | $C_2H_5$ | 2 | — | 0 | $-(CH_2)_2-N(CH_2CH_3)-(CH_2)_2-$ | | H |
| 86 | O | $C_2H_5$ | 3 | O | 1 | $-(CH_2)_2-O-(CH_2)_2-$ | | H |
| 87 | O | $C_2H_5$ | 3 | O | 1 | $-(CH_2)_5-$ | | H |
| 88 | O | $C_2H_5$ | 3 | O | 2 | $C_2H_5$ | $C_2H_5$ | H |
| 89 | S | $C_2H_5$ | 2 | — | 0 | $CH_3$ | $CH_3$ | H |

Then, PDE inhibitory activity and pharmacological activity of the representative Compounds (I) are described in more detail by Test Examples.

Test Example 1:

The inhibitory activity on PDE derived from canine tracheal smooth muscle (1) Purification of an enzyme According to the method of Torphy et al. [Mol. Pharmacol., 37, 206 (1990)], PDE V (cGMP-specific PDE) was purified from canine tracheal smooth muscle.

(2) Measurement of PDE activity

The activity was measured based on the method of Kincaid et al. [J. D. Corbin et al., Methods Enzymol., 159, 457 (1988), Academic Press, New York]. The measurement was carried out using, as a substrate, 1.0 μM [$^3$H]cGMP, and the reaction was carried out in a buffer having the following composition:

50 mM N,N-bis(2-hydroxyethyl)-2-aminoethanesulfonic acid (pH 7.2), 1 mM MgCl$_2$, 0.1 mg/ml soybean trypsin inhibitor The reaction was started by addition of an enzyme and stopped by addition of hydrochloric acid after 10 to 30 minutes at 30° C. Thereafter, sodium hydroxide was added for neutralization and 5'-GMP was converted into guanosine using 5'-nucleotidase. The reaction solution was subjected to DEAE-Sephadex A-25 column. [$^3$H]Guanosine was eluted with distilled water and the radioactivity was measured with a liquid scintillation counter. The inhibitor was dissolved in 1.7% DMSO.

The results on the PDE inhibitory activity are shown in Table 2.

TABLE 2

| Compd. No. | PDE V Inhibitory activity* |
|---|---|
| 1 | 74% (1 nM) |
| 4 | 97% (1 nM) |
| 15 | 63% (1 nM) |
| 21 | 29% (1 nM) |
| 29 | 91% (1 nM) |
| 32 | 79% (1 nM) |
| 42 | 89% (1 nM) |
| 71 | 97% (1 nM) |
| 75 | 92% (1 nM) |
| 76 | 88% (1 nM) |
| 79 | 95% (1 nM) |
| 80 | 92% (1 nM) |

*: inhibition rate (%)

Test Example 2:

The hypotensive effect in rats

After a male Sprague-Dawley rat anesthetized with urethane was fixed in the supine position, a cannula was inserted into trachea and the rat was artificially ventilated under the conditions of a tidal volume of 10 mg/kg and 60 breathes/min. The carotid artery and the duodenum were cannulated for measuring blood pressure and administering a drug, respectively. The drug was dissolved in distilled water and administered duodenally using the above cannula. Mean blood pressure (mBP) until 30 minutes after the drug-administration was measured and the maximum loweing rate (%) from the value before the drug-administration (100%) was determined. The average value of 2 samples was calculated in each dose. No change of mBP was observed during 30 minutes in case of administering distilled water.

The results are shown in Table 3.

TABLE 3

| | Hypotensive activity (rat, i.d.) N = 2 | | |
|---|---|---|---|
| Dose of drug (mg/kg) | 0.1 | 1 | 10 |
| Compound 4 Maximum lowering rate (%) | 9.0 | 21.5 | 25.1 |
| Compound 71 Maximum lowering rate (%) | 16.1 | 22.8 | 23.2 |

Compound (I) or pharmaceutically acceptable salts thereof can be formulated into the normally employed forms, for example, tablets, capsules, injections, drops, suppositories, or the like, and the resulting preparations can be administered orally or parenterally, for example, intramuscularly, intravenously, intra-arterialy, by instillation, or rectally by suppositories. Formulation into those oral or parenteral preparations normally uses the known methods. Preparations may contain various excipients, lubricants, binders, disintegrating agents, suspending agents, isotonizing agents, emulsifiers, and the like.

The examples of carriers to be used for preparations are water, distilled water for injection, physiological saline, glucose, sucrose, mannitol, lactose, starch, cellulose, methylcellulose, carboxymethyl cellulose, hydroxypropyl cellulose, alginate, talc, sodium citrate, calcium carbonate, calcium hydrogenphosphate, magnesium stearate, urea, silicone resin, sorbitan fatty acid ester, glyceric acid ester, and the like.

The dose and frequency of administration varies depending upon the mode of administration, the age, weight and conditions of patients, and the like. Normally, the oral dose of 0.05–5 g/60 kg/day is suitable. In the case of instillation, the dose is preferably in a range of 0.01–5 mg/kg/min. and preferably does not exceed the limit of the oral dose per day.

Certain embodiments of the present invention are illustrated in the following Examples and Reference Examples.

BEST MODE FOR CARRYING OUT THE INVENTION

The measurement of proton nuclear magnetic resonance spectrum (NMR) used in Examples and Reference Examples was carried out at 270 MHz unless otherwise indicated. Peak positions are expressed as units of 1/million (ppm) downfield from tetramethylsilane. Peak shapes are expressed as follows: s:singlet, d:doublet, t:triplet, q:quartet, m:multiplet, br:broad

REFERENCE EXAMPLE 1

7-Ethylamino-6-nitro-4(3H)-quinazolone (Compound III-1)

A 70% aqueous ethylamine solution (40 ml) was added to a solution (70 ml) of 7-chloro-6-nitro-4(3H)-quinazolone (6.31 g, 28.0 mmol) in ethanol and the mixture was heated with stirring at 110° C. for 4 hours in a sealed tube. After cooling to room temperature, the reaction mixture was poured into water and the precipitated crystals were collected by filtration. The crystals were washed with ethanol and dried to give the title compound (2.6 g, 39%).

$^1$H-NMR (DMSO-d$_6$) δ(ppm): 1.26(3H, t, J=6.9 Hz), 3.35–3.50(2H, m), 6.92(1H, s), 8.07(1H, s), 8.10–8.15(1H, m), 8.74(1H, br).

REFERENCE EXAMPLE 2

4-Chloro-7-ethylamino-6-nitroquinazoline (Compound IV-1)

7-Ethylamino-6-nitro-4(3H)-quinazolone (12.0 g, 51.3 mmol) obtained in Reference Example 1 was added to phosphorus oxychloride (126 ml) and the mixture was stirred at 120° C. for 2 hours. After a solvent was distilled off, the residue was subjected to azeotrope with toluene. After azeotropy, a saturated aqueous solution of sodium bicarbonate was added thereto, the mixture was extracted with ethyl acetate, and the organic layer was dried over anhydrous magnesium sulfate. The drying agent was filtered off and the filtrate was concentrated under reduced pressure to give the title compound (11.58 g, 89%) as a crude product. Compound (IV-1) was used in the subsequent reaction without further purification.

REFERENCE EXAMPLE 3

2-(Hydroxymethyl)benzylamine

Lithium aluminium hydride (17.4 g, 458 mmol) was suspended in dried tetrahydrofuran (300 ml), followed by stirring under ice-cooling in an argon atmosphere. A solution of 2-cyanobenzaldehyde (20.0 g, 153 mmol) dissolved in dried tetrahydrofuran (100 ml) was dropwise and portion-wise added thereto and the reaction solution was stirred for 3 hours under heating at reflux. After the reaction, the solution was ice-cooled and sodium sulfate 10 hydrate was portionwise added thereto until foaming and fever ceased. The reaction solution was filtered and the filtrate was concentrated to give the title compound (20.9 g, quantitative) as oily substances. This compound was used in the subsequent reaction without further purification.

REFERENCE EXAMPLE 4

7-Ethylamino-4-[2-(hydroxymethyl)benzylamino]-6-nitroquinazoline

4-Chloro-7-ethylamino-6-nitroquinazoline (11.58 g, 45.9 mmol) obtained in Reference Example 2 was suspended in tetrahydrofuran (400 ml), and 2-(hydroxymethyl)benzylamine (7.50 g, 54.7 mmol) obtained in Reference Example 3 and triethylamine (30 ml) were added thereto, followed by stirring at room temperature for one night. After the reaction, the reaction mixture was concentrated under reduced pressure, and the residue was purified by silica gel column chromatography (elution of chloroform—chloroform/methanol=100) to give the title compound (10.60 g, 65%).

$^1$H-NMR (CDCl$_3$) δ(ppm): 1.39(3H, t, J=7.1 Hz), 3.38 (2H, q, J=7.1 Hz), 4.75(2H, s), 4.85(2H, s), 6.89(1H, s), 7.25–7.30(2H, m), 7.41–7.44(2H, m), 7.69(1H, s), 8.36(1H, s), 8.95(1H, br), 9.27(1H, s).

REFERENCE EXAMPLE 5

7-Ethylamino-4-[3-(hydroxymethyl)benzylamino]-6-nitroquinazoline

According to a similar manner as that in Reference Example 4 except that 4-chloro-7-ethylamino-6-nitroquinazoline obtained in Reference Example 2 and 3-(hydroxymethyl)benzylamine, which is prepared from 3-cyanobenzaldehyde according to a similar manner as that in Reference Example 3, were used, the title compound was obtained.

$^1$H-NMR (DMSO-d$_6$) δ(ppm): 1.27(3H, t, J=7.1 Hz), 3.35(2H, q, J=7.1 Hz), 4.48(2H, d, J=5.6 Hz), 4.74(2H, d, J=5.6 Hz), 5.17(1H, t, J=5.6 Hz), 6.86(1H, s), 7.17–7.32(4H, m), 7.74(1H, br), 8.33(1H, s), 9.23(1H, br), 9.29(1H, s).

REFERENCE EXAMPLE 6

7-Ethylamino-4-[4-(hydroxymethyl)benzylamino]-6-nitroquinazoline

According to a similar manner as that in Reference Example 4 except that 4-chloro-7-ethylamino-6-nitroquinazoline obtained in Reference Example 2 and 4-(hydroxymethyl)benzylamine, which is prepared from 4-cyanobenzaldehyde according to a similar manner as that in Reference Example 3, were used, the title compound was obtained.

$^1$H-NMR (CDCl$_3$-CD$_3$OD) δ(ppm): 1.41(3H, t, J=7.3 Hz), 3.42 (2H, q, J=7.3 Hz), 4.64(2H, s), 4.82(2H, s), 6.95 (1H, s), 7.32–7.42(4H, m), 8.41(1H, s), 9.03(1H, s).

REFERENCE EXAMPLE 7

2-(1-Hydroxyethyl)benzylamine

A 1M solution of methylmagnesium bromide in tetrahydrofuran (12 ml, 12 mmol) was dropwise and portionwise added to a solution of 2-cyanobenzaldehyde (1.31 g, 10.0 mmol) dissolved in dried tetrahydrofuran (25 ml), followed by stirring at room temperature for one night. After the reaction, water was added to the reaction mixture followed by extraction with ethyl acetate. The organic layer was dried over anhydrous magnesium sulfate, the drying agent was filtered off, and the solution was concentrated under reduced pressure to give 1-(2-cyanophenyl)ethanol (1.47 g, quantitative).

$^1$H-NMR (CDCl$_3$) δ(ppm): 1.54(3H, d, J=6.6 Hz), 5.51 (1H, q, J=6.6 Hz), 7.31(1H, d, J=6.9 Hz), 7.35–7.50(2H, m), 7.83(1H, d, J=7.6 Hz).

Lithium aluminium hydride (0.758 g, 20.0 mmol) was suspended in dried tetrahydrofuran (20 ml), followed by stirring under ice-cooling in an argon atmosphere. A solution of 1-(2-cyanophenyl)ethanol (1.47 g) obtained above dissolved in dried tetrahydrofuran (20 ml) was dropwise and portionwise added thereto and the reaction solution was stirred for one hour under heating at reflux. After the reaction, the solution was ice-cooled and sodium sulfate 10 hydrate was portionwise added thereto until foaming and fever ceased. The reaction solution was filtered and the filtrate was concentrated to give the title compound (1.21 g, 84%) as oily substances. This compound was used in the subsequent reaction without further purification.

REFERENCE EXAMPLE 8

7-Ethylamino-4-[2-(1-hydroxyethyl)benzylamino]-6-nitroquinazoline

According to a similar manner as that in Reference Example 4 except that 4-chloro-7-ethylamino-6-nitroquinazoline obtained in Reference Example 2 and 2-(1-hydroxyethyl)benzylamine obtained in Reference Example 7 were used, the title compound was obtained.

$^1$H-NMR (CDCl$_3$) δ(ppm): 1.39(3H, t, J=7.3 Hz), 1.62 (3H, d, J=6.6 Hz), 3.35(2H, q, J=7.3 Hz), 4.89(2H, s), 5.24 (1H, q, J=6.6 Hz), 6.88(1H, s), 7.26–7.43(4H, m), 7.52(1H, dd, J=1.5 Hz, 7.6 Hz), 7.68(1H, br), 8.34 (1H, s), 8.90(1H, s).

REFERENCE EXAMPLE 9

7-Ethylamino-4-[2-(morpholinomethyl)
benzylamino]-6-nitroquinazoline

7-Ethylamino-4-[2-(hydroxymethyl)benzylamino]-6-nitroquinazoline (2.0 g, 5.67 mmol) obtained in Reference Example 4 was dissolved in N,N-dimethylformamide (50 ml), and 2,6-lutidine (1.46 ml, 12.5 mmol) was added thereto at room temperature. Methanesulfonyl chloride (0.96 ml, 12.5 mmol) was added to the mixture, followed by stirring at 50° C. for one hour. After the reaction, water was added to the reaction mixture and the precipitated solid was dried to give a solid (2.9 g).

The solid (1.45 g) obtained above was dissolved in N,N-dimethylformamide (50 ml), and morpholine (1.0 ml, 11.50 mmol) and sodium iodide (0.85 g, 5.66 mmol) were added thereto, followed by stirring at 100° C. for 2 hours. After the reaction, water was added to the reaction mixture and the precipitated solid was dried to give the title compound (980 mg, 82%).

$^1$H-NMR (CDCl$_3$) δ(ppm): 1.40(3H, t, J=7.1 Hz), 2.50–2.60 (4H, m), 3.38(2H, q, J=7.1 Hz), 3.62(2H, s), 3.70–3.80(4H, m), 4.89(2H, s), 7.01(1H, s), 7.27–7.37 (3H, m), 7.50–7.60(1H, m), 7.67–7.82(2H, m), 8.56(1H, s), 8.74 (1H, s).

The following compounds of Reference Examples 10 to 19, 21 to 25, and 49 to 58 were prepared according to a manner similar to that in Reference Example 9 except for using 7-ethylamino-4-[2-(hydroxymethyl)benzylamino]-6-nitroquinazoline, 7-ethylamino-4-[3-(hydroxymethyl)benzylamino]-6-nitroquinazoline, 7-ethylamino-4-[4-(hydroxymethyl)benzylamino]-6-nitroquinazoline, or 7-ethylamino-4-[2-(1-hydroxyethyl)benzylamino]-6-nitroquinazoline obtained in Reference Example 4, 5, 6, or 8, and converting the hydroxyl groups into appropriate leaving groups, and thereafter using the corresponding amines in place of morpholine.

REFERENCE EXAMPLE 10

7-Ethylamino-4-[3-(morpholinomethyl)
benzylamino]-6-nitroquinazoline

The title compound was obtained from 7-ethylamino-4-[3-(hydroxymethyl)benzylamino]-6-nitroquinazoline obtained in Reference Example 5 and morpholine.

$^1$H-NMR (CDCl$_3$) δ(ppm): 1.39(3H, t, J=7.4 Hz), 2.43–2.50 (4H, m), 3.36(2H, q, J=7.4 Hz), 3.47(2H, s), 3.64–3.77(4H, m), 4.85(2H, s), 6.60(1H, br), 6.99(1H, s), 7.27–7.36(2H, m), 7.41(1H, s), 7.65–7.69(1H, m), 8.52(1H, s), 8.79(1H, s).

REFERENCE EXAMPLE 11

7-Ethylamino-6-nitro-4-[4-(piperidinomethyl)
benzylamino]quinazoline

The title compound was obtained from 7-ethylamino-4-[4-(hydroxymethyl)benzylamino]-6-nitroquinazoline obtained in Reference Example 6 and piperidine.

$^1$H-NMR (CDCl$_3$) δ(ppm): 1.39(3H, t, J=7.2 Hz), 1.50–2.00 (6H, m), 2.80–3.00(2H, m), 3.50–3.70(4H, m), 3.36 (2H, q, J=7.2 Hz), 4.80(2H, s), 6.94(1H, s), 7.40 (2H, d, J=7.9 Hz), 7.51(2H, d, J=7.9 Hz), 7.60–7.70 (1H, m), 8.47(1H, s), 8.97(1H, s).

REFERENCE EXAMPLE 12

7-Ethylamino-6-nitro-4-[2-(piperidinomethyl)
benzylamino]quinazoline

The title compound was obtained from 7-ethylamino-4-[2(hydroxymethyl)benzylamino]-6-nitroquinazoline obtained in Reference Example 4 and piperidine.

$^1$H-NMR (CDCl$_3$) δ(ppm): 1.40(3H, t, J=7.1 Hz), 1.50–1.80 (6H, m), 2.50–2.60(4H, m), 3.37(2H, q, J=7.1 Hz), 3.58(2H, s), 4.86(2H, d, J=4.3 Hz), 6.96(1H, s), 7.23–7.35(3H, m), 7.57(1H, d, J=6.3 Hz), 7.68(1H, br), 8.41(1H, br), 8.55(1H, s), 8.70(1H, s).

REFERENCE EXAMPLE 13

4-[2-(Diethylaminomethyl)benzylamino]-7-
ethylamino-6-nitroquinazoline

The title compound was obtained from 7-ethylamino-4-[2-(hydroxymethyl)benzylamino]-6-nitroquinazoline obtained in Reference Example 4 and diethylamine.

$^1$H-NMR (CDCl$_3$) δ(ppm): 1.11(6H, t, J=7.2 Hz), 1.38 (3H, t, J=7.2 Hz), 2.70–2.85(4H, m), 3.34(2H, q, J=7.2 Hz), 3.74(2H, s), 4.89(2H, d, J=3.5 Hz), 6.91(1H, s), 7.20–7.30 (3H, m), 7.45–7.50(1H, m), 7.60–7.70(1H, m), 8.51(1H, s), 8.60(1H, s), 9.85(1H, br).

REFERENCE EXAMPLE 14

7-Ethylamino-4-[2-(4-methylpiperazin-1-ylmethyl)
benzylamino]-6-nitroquinazoline The title compound was obtained from 7-ethylamino-4-[2-(hydroxymethyl)benzylamino]-6-nitroquinazoline obtained in Reference Example 4 and 1-methylpiperazine.

$^1$H-NMR (CDCl$_3$) δ(ppm): 1.41(3H, t, J=7.2 Hz), 2.28 (3H, s), 2.32–2.62(8H, m), 3.36(2H, q, J=7.2 Hz), 3.60 (2H, s), 4.84(2H, d, J=6.9 Hz), 6.98(1H, s), 7.20–7.32(3H, m), 7.55–7.59(1H, m), 7.68(1H, br), 7.83 (1H, br), 8.56(1H, s), 8.68(1H, s).

REFERENCE EXAMPLE 15

4-[2-(4-Benzylpiperazin-1-ylmethyl)benzylamino]-
7-ethylamino-6-nitroquinazoline The title compound was obtained from 7-ethylamino-4-[2-(hydroxymethyl)benzylamino]-6-nitroquinazoline obtained in Reference Example 4 and 1-benzylpiperazine.

$^1$H-NMR (CDCl$_3$) δ(ppm): 1.41(3H, t, J=7.3 Hz), 2.40–2.65 (8H, m), 3.39(2H, q, J=7.3 Hz), 3.44(2H, s), 3.59 (2H, s), 4.83(2H, d, J=5.0 Hz), 6.98(1H, s), 7.21–7.35(8H, m), 7.57(1H, d, J=6.6 Hz), 7.69(1H, br), 8.00(1H, br), 8.56 (1H, s), 8.72(1H, s).

REFERENCE EXAMPLE 16

7-Ethylamino-6-nitro-4-{2-[4-(2-pyridyl)piperazin-
1-ylmethyl]benzylamino}quinazoline The title compound was obtained from 7-ethylamino-4-[2-(hydroxymethyl)benzylamino]-6-nitroquinazoline obtained in Reference Example 4 and 1-(2-pyridyl)piperazine.

$^1$H-NMR (CDCl$_3$) δ(ppm): 1.36(3H, t, J=7.3 Hz), 2.68–2.72(4H, m), 3.35(2H, q, J=7.3 Hz), 3.57–3.61(4H, m), 3.68(2H, s), 4.91(2H, s), 6.61–6.69(2H, m), 6.98 (1H, s), 7.23–7.40(4H, m), 7.45–7.60(3H, m), 8.16 (1H, d, J=3.6 Hz), 8.55(1H, s), 8.66(1H, s).

REFERENCE EXAMPLE 17

7-Ethylamino-6-nitro-4-{2-{[(2-pyridyl)methyl]
aminomethyl}benzylamino}quinazoline The title compound was obtained from 7-ethylamino-4-[2-(hydroxymethyl)benzylamino]-6-nitroquinazoline obtained in Reference Example 4 and [(2-pyridyl)methyl]amine.

¹H-NMR (DMSO-d₆) δ(ppm): 1.27(3H, t, J=7.1 Hz), 3.34(2H, q, J=7.1 Hz), 3.83(2H, s), 3.86(2H, s), 4.82(2H, d, J=4.3 Hz), 6.85(1H, s), 7.18–7.90(7H, m), 8.29(1H, s), 8.44(1H, d, J=4.0 Hz), 9.21(1H, s), 9.30(1H, br).

REFERENCE EXAMPLE 18

7-Ethylamino-4-[2-(1-morpholinoethyl)benzylamino]-6-nitroquinazoline

The title compound was obtained from 7-ethylamino-4-[2-(1-hydroxyethyl)benzylamino]-6-nitroquinazoline obtained in Reference Example 8 and morpholine.

¹H-NMR (CDCl₃) δ(ppm): 1.39–1.43(6H, m), 2.43–2.50 (2H, m), 2.50–2.62(2H, m), 3.39(2H, q, J=7.3 Hz), 3.64–3.73(4H, m), 3.89(1H, q, J=6.6 Hz), 4.75–4.82(1H, m), 5.05–5.13(1H, m), 6.80(1H, br), 7.00(1H, s), 7.26–7.38(2H, m), 7.43–7.50(2H, m), 7.69(1H, br), 8.56(1H, s), 8.70(1H, s).

REFERENCE EXAMPLE 19

7-Ethylamino-4-{2-[1-(4-methylpiperazin-1-yl)ethyl]benzylamino}-6-nitroquinazoline The title compound was obtained from 7-ethylamino-4-[2-(1-hydroxyethyl)benzylamino]-6-nitroquinazoline obtained in Reference Example 8 and 1-methylpiperazine.

¹H-NMR (CDCl₃) δ(ppm): 1.38–1.44(6H, m), 2.21(3H, s), 2.35–2.70(8H, m), 3.39(2H, q, J=7.3 Hz), 3.97(1H, q, J=6.9 Hz), 4.70–4.75(1H, m), 5.02–5.09(1H, m), 6.93–7.00 (1H, m), 7.00(1H, s), 7.25–7.40(2H, m), 7.43–7.50(2H, m), 7.78(1H, br), 8.56(1H, s), 8.67 (1H, s).

REFERENCE EXAMPLE 20

7-Ethylamino-4-[4-(morpholinomethyl)benzylamino]-6-nitroquinazoline

7-Ethylamino-4-[4-(hydroxymethyl)benzylamino]-6-nitroquinazoline (1.5 g, 4.25 mmol) obtained in Reference Example 6 was suspended in 1,2-dichloroethane (50 ml), and 2,6-lutidine (0.74 ml, 6.35 mmol) was added thereto. Methanesulfonyl chloride (0.48 ml, 6.35 mmol) was added to the mixture, followed by stirring at 70° C. for one hour. After the reaction, water was added to the reaction mixture, the mixture was extracted with chloroform, and the organic layer was dried over anhydrous magnesium sulfate. The drying agent was filtered off and the filtrate was concentrated under reduced pressure to give oily substances (1.56 g).

The oily substances (1.56 g) obtained above was dissolved in N,N-dimethylformamide (50 ml), and morpholine (2.24 ml, 25.7 mmol) and sodium iodide (1.27 g, 8.47 mmol) were added thereto, followed by stirring at 100° C. After the reaction, the reaction mixture was concentrated under reduced pressure and the residue was purified by silica gel column chromatography (eluent: chloroform—chloroform/methanol=100) to give the title compound (1.78 g, 99%).

¹H-NMR (CDCl₃) δ(ppm): 1.39(3H, t, j=7.3 Hz), 2.42–2.46 (4H, m), 3.36(2H, q, J=7.3 Hz), 3.49(2H, s), 3.67–3.71(4H, m), 4.83(2H, d, J=5.3 Hz), 6.97(1H, s), 6.94–7.01(1H, m), 7.29–7.37(4H, m), 7.65–7.69(1H, m), 8.51(1H, s), 8.87(1H, s).

REFERENCE EXAMPLE 21

7-Ethylamino-4-[4-(4-methylpiperazin-1-ylmethyl)benzylamino]-6-nitroquinazoline

The title compound was obtained from 7-ethylamino-4-[4-(hydroxymethyl)benzylamino]-6-nitroquinazoline obtained in Reference Example 6 and 1-methylpiperazine.

¹H-NMR (CDCl₃) δ(ppm): 1.41(3H, t, J=7.2 Hz), 2.45 (3H, s), 2.88–2.91(4H, m), 3.29–3.34(4H, m), 3.38(2H, q, J=7.2 Hz), 3.65(2H, s), 4.86(2H, s), 6.99(1H, s), 7.30(2H, d, J=7.9 Hz), 7.40(2H, d, J=7.9 Hz), 8.48(1H, s), 9.00(1H, s).

REFERENCE EXAMPLE 22

4-{4-[(1-Butylamino)methyl]benzylamino}-7-ethylamino-6-nitroquinazoline

The title compound was obtained from 7-ethylamino-4-[4-(hydroxymethyl)benzylamino]-6nitroquinazoline obtained in Reference Example 6 and 1-butylamine.

¹H-NMR (DMSO-d₆) δ(ppm): 0.87(3H, t, J=7.6 Hz), 1.24–1.34 (5H, m), 1.47–1.53(2H, m), 2.72(2H, t, J=7.6 Hz), 3.39(2H, q, J=6.9 Hz), 3.94(2H, s), 4.75(2H, d, J=5.0 Hz), 6.86(1H, s), 7.38(4H, s), 7.77(1H, t, J=5.0 Hz), 8.32(1H, s), 9.28(2H, m).

REFERENCE EXAMPLE 23

7-Ethylamino-6-nitro-4-{4-[(1-propylamino)methyl]benzylamino}quinazoline

The title compound was obtained from 7-ethylamino-[4-(hydroxymethyl)benzylamino]-6-nitroquinazoline obtained in Reference Example 6 and 1-propylamine.

¹H-NMR (DMSO-₆) δ(ppm): 0.89(3H, t, J=7.3 Hz), 1.27 (3H, t, J=7.1 Hz), 1.54–1.63(2H, m), 2.80(2H, t, J=7.7 Hz), 3.37(2H, q, J=7.1 Hz), 4.06(2H, s), 4.76 (2H, d, J=5.4 Hz), 6.87(1H, s), 7.41(4H, s), 7.77 (1H, t, J=5.4 Hz), 8.31(1H, s), 9.29(2H, m).

REFERENCE EXAMPLE 24

7-Ethylamino-6-nitro-4-{4-{[(2-pyridyl)methyl]aminomethyl}benzylamino}quinazoline The title compound was obtained from 7-ethylamino-4-[4-(hydroxymethyl)benzylamino]-6-nitroquinazoline obtained in Reference Example 6 and [(2-pyridyl)methyl]amine.

¹NMR (DMSO-d₆) δ(ppm): 1.27(3H, t, J=7.1 Hz), 3.39 (2H, q, J=7.1 Hz), 3.69(2H, s), 3.76(2H, s), 4.73(2H, d, J=6.9 Hz), 6.86(1H, s), 7.23(1H, dd, J=5.0 Hz, 7.6 Hz), 7.30–7.34(1H, m), 7.44(1H, d, J=7.9 Hz), 7.70–7.77(2H, m), 8.30–8.33(2H, m), 8.47(1H, d, J=4.6 Hz), 9.21(1H, br), 9.29(1H, s).

REFERENCE EXAMPLE 25

7-Ethylamino-6-nitro-4-{4-[(1-pyrrolidinyl)methyl]benzylamino}quinazoline

The title compound was obtained from 7-ethylamino-[4-(hydroxymethyl)benzylamino]-6-nitroquinazoline obtained in Reference Example 6 and pyrrolidine.

¹H-NMR (DMSO-d₆) δ(ppm): 1.27(3H, t, J=7.0 Hz), 1.81–1.88 (4H, m), 3.08–3.14(4H, m), 3.40(2H, q, J=7.0 Hz), 4.30(2H, s), 4.78(2H, d, J=5.6 Hz), 6.88(1H, s), 7.39–7.45(4H, m), 7.74(1H, t, J=5.6 Hz), 8.32(1H, s), 9.29 (2H, m).

REFERENCE EXAMPLE 26

2-(2-Hydroxyethoxy)benzylamine

2-Cyanophenol (1.0 g, 8.39 mmol) was dissolved in N,N-dimethylformamide (5 ml), and potassium carbonate (1.22 g, 8.82 mmol) and methyl bromoacetate (0.85 ml, 8.98 mmol) were added thereto, followed by stirring at room temperature for one hour. After the reaction, water was added to the reaction mixture, and the precipitated solid was collected followed by drying (1.33 g, 83%).

Lithium aluminium hydride (6.0 g, 158.0 mmol) was suspended in dried tetrahydrofuran (150 ml), and a solution of the solid (10.0 g) obtained above dissolved in dried tetrahydrofuran (80 ml) was dropwise and portionwise added thereto, followed by stirring for 5 hours under heating at reflux. After the reaction, the solution was ice-cooled and sodium sulfate 10 hydrate was portionwise added thereto until foaming and fever ceased. The reaction solution was filtered and the filtrate was concentrated to give the title compound (6.08 g, 70%) as oily substances.

$^1$H-NMR (CDCl$_3$) δ(ppm): 3.73–3.85(4H, m), 4.14(2H, t, J=4.3 Hz), 6.83–6.91(2H, m), 7.08–7.30(2H, m).

REFERENCE EXAMPLE 27

7-Ethylamino-4-[2-(2-hydroxyethoxy)benzylamino]-6-nitroquinazoline

4-Chloro-7-ethylamino-6-nitroquinazoline (3.90 g, 15.4 mmol) obtained in Reference Example 2 was suspended in tetrahydrofuran (200 ml), and triethylamine (4.8 ml, 34.2 mmol) was added thereto, followed by stirring at room temperature. A solution of 2-(2-hydroxyethoxy)benzylamine (3.15 g, 18.9 mmol) obtained in Reference Example 26 dissolved in tetrahydrofuran (30 ml) was dropwise added to the mixture, followed by stirring for one night. After the reaction, water was added to the reaction mixture, and the precipitated solid was collected followed by drying to give the title compound (3.62 g, 61%).

$^1$H-NMR (CDCl$_3$) δ(ppm): 1.39(3H, t, J=7.1 Hz), 3.37 (2H, q, J=7.1 Hz), 3.93(2H, t, J=4.3 Hz), 4.14(2H, t, J=4.3 Hz), 4.85(2H, d, J=5.3 Hz), 6.85–6.95(3H, m), 7.22–7.29 (1H, m), 7.37(1H, s), 7.44(1H, d, J=7.3 Hz), 7.60(1H, dd, J=5.3 Hz, 5.3 Hz), 8.43(1H, s), 8.55(1H, br), 9.23(1H, s).

REFERENCE EXAMPLE 28

7-Ethylamino-4-[2-(2-morpholinoethoxy)benzylamino]-6-nitroquinazoline

7-Ethylamino-4-[2-(2-hydroxyethoxy)benzylamino]-6-nitroquinazoline (1.0 g, 2.61 mmol) obtained in reference Example 27 was suspended in N,N-dimethylformamide (100 ml), and 2,6-lutidine (0.8 ml, 6.8 mmol) and methanesulfonyl chloride (0.5 ml, 6.2 mmol) were added thereto, followed by stirring at 50° C. for one hour. After the reaction, the solvent was removed under reduced pressure, water was added to the residue, and the precipitated solid was collected by filtration followed by drying (0.95 g).

The solid (0.475 g) obtained above was dissolved in N,N-dimethylformamide (20 ml), and morpholine (0.6 ml, 7.02 mmol) and sodium iodide (0.35 g, 2,34 mmol) were added thereto, followed by stirring at 100° C. for 8 hours. After the reaction, water was added to the reaction mixture, the mixture was extracted with chloroform, and the organic layer was dried over anhydrous magnesium sulfate. The drying agent was filtered off, the filtrate was concentrated, and the residue was purified by silica gel column chromatography (eluent:chloroform/methanol=100) to give the title compound (0.43 g, 73%).

$^1$H-NMR (CDCl$_3$) δ(ppm): 1.40(3H, t, J=7.1 Hz), 2.58–2.62 (4H, m), 2.89(2H, t, J=5.8 Hz), 3.37(2H, q, J=7.1 Hz), 3.65–3.69(4H, m), 4.22(2H, t, J=5.8 Hz), 4.86(2H, d, J=5.6 Hz), 6.78–6.82(1H, m), 6.90–7.00 (3H, m), 7.25–7.40 (2H, m), 7.60–7.70(1H, m), 8.52(1H, s), 8.70(1H, s).

The following compounds of Reference Examples 29 to 31, 42, 44 to 46, 48, and 63 to 68 were prepared according to a manner similar to that in Reference Example 28.

REFERENCE EXAMPLE 29

7-Ethylamino-6-nitro-4-[2-(2-piperidinoethoxy)benzylamino]quinazoline

The title compound was obtained from 7-ethylamino-[2-(2-hydroxyethoxy)benzylamino]-6-nitroquinazoline obtained in Reference Example 27 and piperidine.

$^1$H-NMR (CDCl$_3$) δ(ppm): 1.35–1.50(2H, m), 1.40(3H, t, J=7.1 Hz), 1.55–1.80(4H, m), 2.50–2.75(4H, m), 2.93 (2H, t, J=5.6 Hz), 3.37(2H, q, J=7.1 Hz), 4.23(2H, t, J=5.6 Hz), 4.86(2H, d, J=5.6 Hz), 6.92–6.99(3H, m), 7.26–7.46(2H, m), 7.62–7.71(1H, m), 8.51(1H, s), 8.83(1H, s).

REFERENCE EXAMPLE 30

4-{2-[2-(Diethylamino)ethoxy]benzylamino}-7-ethylamino-6-nitroquinazoline

The title compound was obtained from 7-ethylamino-4-[2-(2-hydroxyethoxy)benzylamino]-6-nitroquinazoline obtained in Reference Example 27 and diethylamine.

$^1$H-NMR (CDCl$_3$) δ(ppm): 1.06(6H, t, J=7.1 Hz), 1.39 (3H, t, J=7.3 Hz), 2.68(4H, q, J=7.1 Hz), 2.94(2H, t, J=5.6 Hz), 3.35(2H, q, J=7.3 Hz), 4.13(2H, t, J=5.6 Hz), 4.85(2H, d, J=5.6 Hz), 6.89–6.96(3H, m), 7.24–7.30(1H, m), 7.42(1H, d, J=7.3 Hz), 7.67(1H, br), 8.51(1H, s), 8.79(1H, s).

REFERENCE EXAMPLE 31

7-Ethylamino-4-{2-[2-(4-methylpiperazin-1-yl)ethoxy]benzylamino}-6-nitroquinazoline The title compound was obtained from 7-ethylamino-4-[2-(2-hydroxyethoxy)benzylamino]-6-nitroquinazoline obtained in Reference Example 27 and 1-methylpiperazine.

$^1$H-NMR (CDCl$_3$) δ(ppm): 1.40(3H, t, J=7.2 Hz), 2.26 (3H, s), 2.30–2.52(5H, m), 2.57–2.75(3H, m), 2.91(2H, t, J=5.7 Hz), 3.37(2H, q, J=7.2 Hz), 4.21(2H, t, J=5.7 Hz), 4.85(2H, d, J=5.9 Hz), 6.85–6.99(3H, m), 7.05–7.15(1H, m), 7.22–7.30(1H, m), 7.42(1H, dd, J=1.5 Hz, 7.4Hz), 7.62–7.70 (1H, m), 8.52(1H, s), 8.77(1H, s).

REFERENCE EXAMPLE 32

3-[3-(Dimethylamino)propoxy]benzylamine

3-Cyanophenol (3.50 g, 29.4 mmol) was dissolved in N,N-dimethylformamide (5 ml), and 60% sodium hydride (2.70 g, 67.5 mmol) was added thereto under ice-cooling, followed by stirring for one hour. 3-(Dimethylamino)propyl chloride hydrochloride (4.64 g, 29.4 mmol) was added to the mixture followed by stirring from under ice-cooling to at room temperature for 4 hours. After the reaction, water was added to the reaction mixture, the mixture was extracted with ether, and the extract was concentrated under reduced pressure to give oily substances.

Lithium aluminium hydride (3.35 g, 88.2 mmol) was suspended in dried tetrahydrofuran (50 ml), and a solution of the oily substances (5.21 g) obtained above dissolved in dried tetrahydrofuran (100 ml) was dropwise and portionwise added thereto, followed by stirring for 2 hours under heating at reflux. After the reaction, the solution was ice-cooled and sodium sulfate 10 hydrate was portionwise added thereto until foaming and fever ceased. The reaction solution was filtered and the filtrate was concentrated to give the title compound (4.00 g, 95%) as oily substances.

¹H-NMR (CDCl₃) δ(ppm): 1.90–2.00(2H, m), 2.25(6H, s), 2.45(2H, t, J=7.3 Hz), 3.83(2H, br), 4.02(2H, t, J=6.4 Hz), 6.78(1H, dd, J=2.3 Hz, 7.9 Hz), 6.85–6.88 (2H, m), 7.21(1H, d, J=7.9 Hz).

REFERENCE EXAMPLE 33

4-{3-[3-(Dimethylamino)propoxy]benzylamino}-7-ethylamino-6-nitroquinazoline

4-Chloro-7-ethylamino-6-nitroquinazoline (2.70 g, 10.7 mmol) obtained in Reference Example 2 was suspended in tetrahydrofuran (150 ml), and triethylamine (7.4 ml, 53.1 mmol) was added thereto, followed by stirring at room temperature. A solution of 3-[(3-dimethylamino)propoxy]benzylamine (3.33 g, 16.0 mmol) obtained in Reference Example 32 dissolved in tetrahydrofuran (50 ml) was dropwise added to the mixture, followed by stirring for one night. After the reaction, the reaction mixture was concentrated under reduced pressure and the residue was purified by silica gel column chromatography (eluent: chloroform/methanol= 50) to give the title compound (4.15 g, 92%).

¹H-NMR (CDCl₃) δ(ppm): 1.37(3H, t, J=7.3 Hz), 2.09–2.20 (2H, m), 2.58(6H, s), 2.82–2.97(2H, m), 3.32(2H, q, J=7.3 Hz), 3.97(2H, t, J=5.2 Hz), 4.79(2H, s), 6.67–6.70 (1H, m), 6.89(1H, s), 6.88–6.98(1H, m), 7.09–7.18(1H, m), 7.58–7.62(1H, m), 8.46(1H, s), 9.12(1H, s).

The following compounds of Reference Examples 34, 35, 37 to 39, 60, 62, 70, and 72 were prepared according to a manner similar to that in Reference Example 33.

REFERENCE EXAMPLE 34

4-{4-[3-(Dimethylamino)propoxy]benzylamino}-7-ethylamino-6-nitroquinazoline

The title compound was obtained from 4-chloro-7-ethylamino-6-nitroquinazoline obtained in Reference Example 2 and 4-[3-(dimethylamino)propoxy]benzylamine, which is prepared from 4-cyanophenol according to a similar manner as that in Reference Example 32.

¹H-NMR (CDCl₃) δ(ppm): 1.40(3H, t, J=7.2 Hz), 1.95–2.05(2H, m), 2,31(6H, s), 2.52(2H, t, J=7.4 Hz), 3.39 (2H, q, J=7.2 Hz), 4.02(2H, t, J=5.2 Hz), 4.76(2H, d, J=5.4 Hz), 6.20–6.24(1H, m), 6.89(2H, d, J=8.3 Hz), 6.98(1H, s), 7.31(2H, d, J=8.3 Hz), 7.63–7.70(1H, m), 8.54(1H, s), 8.72(1H, s).

REFERENCE EXAMPLE 35

4-{2-[3-(Dimethylamino)propoxy]benzylamino}-7-ethylamino-6-nitroquinazoline

The title compound was obtained from 4-chloro-7-ethylamino-6-nitroquinazoline obtained in Reference Example 2 and 2-[3-(dimethylamino)propoxy]benzylamine, which is prepared from 2-cyanophenol according to a similar manner as that in Reference Example 32.

¹H-NMR (CDCl₃) δ(ppm): 1.38(3H, t, J=7.2 Hz), 2.00–2.11(2H, m), 2.27(6H, s), 2.57(2H, t, J=7.2 Hz), 3.34 (2H, q, J=7.2 Hz), 4.11(2H, t, J=6.2 Hz), 4.84(2H, s), 6.83–6.92(3H, m), 7.20–7.25(1H, m), 7.25–7.37 (1H, m), 7.60–7.67(1H, m), 8.48(1H, s), 8.82(1H, s).

REFERENCE EXAMPLE 36

2-(3-Morpholinopropoxy)benzylamine

2-Cyanophenol (1.19 g, 10.00 mmol) was dissolved in N,N-dimethylformamide (10 ml), and 60% sodium hydride (0.48 g, 12.0 mmol) was added thereto under ice-cooling, followed by stirring for one hour. 1-Bromo-3-chloropropane (1.2 ml, 12.0 mmol) was added to the mixture followed by stirring from under ice-cooling to at room temperature for 4 hours. After the reaction, water was added to the reaction mixture, the mixture was extracted with ethyl acetate, and the extract was concentrated under reduced pressure to give oily substances.

The oily substances (3.4 g) obtained above was dissolved in N,N-dimethylformamide (10 ml), and morpholine (0.87 ml, 20.0 mmol) was added thereto, followed by stirring for one night. After the reaction, water was added to the reaction mixture, and the mixture was extracted with ether. The organic layer was dried, the drying agent was filtered off, and the filtrate was concentrated under reduced pressure to give 2-(3-morpholinopropoxy)benzonitrile (1.62 g, 66%).

¹H-NMR (CDCl₃) δ(ppm): 2.00–2.09(2H, m), 2.40–2.50 (4H, m), 2.57(2H, t, J=4.5 Hz), 3.68–3.74(4H, m), 4.16 (2H, t, J=6.3 Hz), 6.95–7.03(2H, m), 7.49–7.56(2H, m).

Lithium aluminium hydride (0.356 g, 9.35 mmol) was suspended in dried tetrahydrofuran (10 ml), and a solution of 2-(3-morpholinopropoxy)benzonitrile (0.814 g, 3.31 mmol) obtained above dissolved in dried tetrahydrofuran (5 ml) was added thereto under ice-cooling in an argon atmosphere, followed by stirring for one hour under heating at reflux. After the reaction, the solution was ice-cooled and sodium sulfate 10 hydrate was portionwise added thereto until foaming and fever ceased. The reaction solution was filtered and the filtrate was concentrated to give the title compound (0.71 g, 86%) as oily substances. This compound was used in the subsequent reaction without further purification.

REFERENCE EXAMPLE 37

7-Ethylamino-4-[2-(3-morpholinopropoxy)benzylamino]-6-nitroquinazoline

The title compound was obtained from 4-chloro-7-ethylamino-6-nitroquinazoline obtained in Reference Example 2 and 2-(3-morpholinopropoxy)benzylamine obtained in Reference Example 36.

¹H-NMR-(CDCl₃) δ(ppm): 1.37(3H, t, J=7.1 Hz), 1.96–2.07 (2H, m), 2.39–2.50(4H, m), 2.52(2H, t, J=7.1 Hz), 3.32(2H, q, J=7.1 Hz), 3.65–3.70(4H, m), 4.09(2H, t, J=6.3 Hz), 4.84(2H, d, J=5.6 Hz), 6.87–6.91(3H, m), 7.06–7.12 (1H, m), 7.23(1H, d, J=8.2 Hz), 7.27–7.34(1H, m), 7.61–7.67(1H, m), 8.49(1H, s), 8.75 (1H, s).

REFERENCE EXAMPLE 38

7-Ethylamino-4-[2-(4-morpholinobutoxy)benzylamino]-6-nitroquinazoline

The title compound was obtained from 4-chloro-7-ethylamino-6-nitroquinazoline obtained in Reference Example 2 and 2-(4-morpholinobutoxy)benzylamine, which is prepared from 2-cyanophenol, 4-bromo-1-chlorobutane, and morpholine according to a similar manner as that in Reference Example 36.

¹H-NMR (CDCl₃) δ(ppm): 1.40(3H, t, J=7.2 Hz), 1.70–2.00 (4H, m), 2.40–2.50(6H, m), 3.37(2H, q, J=7.2 Hz), 3.62–3.78(4H, m), 4.10(2H, t, J=6.4 Hz), 4.85(2H, s), 6.70(1H, br), 6.80–7.00(2H, m), 7.20–7.40(2H, m), 7.60–7.70(1H, m), 8.52(1H, s), 8.71(1H, s).

REFERENCE EXAMPLE 39

7-Ethylamino-6-nitro-4-[2-(4-piperidinobutoxy)benzylamino]quinazoline

The title compound was obtained from 4-chloro-7-ethylamino-6-nitroquinazoline obtained in Reference Example 2 and 2-(4-piperidinobutoxy)benzylamine, which is prepared from 2-cyanophenol, 4-bromo-1-chlorobutane, and piperidine according to a similar manner as that in Reference Example 36.

¹H-NMR (CDCl₃) δ(ppm): 0.85–0.95(4H, m), 1.39(3H, t, J=7.3 Hz), 1.80–2.00(6H, m), 2.15–2.30(2H, m), 2.90–3.10 (4H, m), 3.35(2H, q, J=7.3 Hz), 4.06(2H, t, J=5.6 Hz), 4.85(2H, s), 6.81–6.94(3H, m), 7.21 (1H, dd, J=6.6 Hz, 7.6 Hz), 7.41(1H, d, J=7.6 Hz), 7.63(1H, br), 7.86(1H, br), 8.42(1H, s), 9.06(1H, s).

REFERENCE EXAMPLE 40

2-[1-(Hydroxymethyl)ethoxy]benzylamine

2-Cyanophenol (1.0 g, 8.39 mmol) was dissolved in N,N-dimethylformamide (5 ml), and 60% sodium hydride (0.40 g, 10 mmol) was added thereto under ice-cooling, followed by stirring for one hour. Methyl (±)-2-bromopropionate (1.03 ml, 9.23 mmol) was added to the mixture followed by stirring at room temperature for one night. After the reaction, water was added to the reaction mixture, and the mixture was extracted with ethyl acetate. The organic layer was dried, the drying agent was filtered off, and the filtrate was concentrated under reduced pressure to give 2-[1-(methoxycarbonyl)ethoxy]benzonitrile (1.70 g, 99%).

¹H-NMR (CDCl₃) δ(ppm): 1.69(3H, d, J=6.9 Hz), 3.76 (3H, s), 4.90(1H, q, J=6.9 Hz), 6.86(1H, d, J=8.6 Hz), 7.05(1H, dd, J=7.6 Hz, 7.6 Hz), 7.51(1H, dd, J=7.6 Hz, 8.6 Hz), 7.57(1H, d, J=7.6 Hz).

Lithium aluminium hydride (0.980 g, 25.8 mmol) was suspended in dried tetrahydrofuran (20 ml), and a solution of 2-[1-(methoxycarbonyl)ethoxy]benzonitrile (1.70 g) obtained above dissolved in dried tetrahydrofuran (20 ml) was added thereto under ice-cooling in an argon atmosphere, followed by stirring for one hour under heating at reflux. After the reaction, the solution was ice-cooled and sodium sulfate 10 hydrate was portionwise added thereto until foaming and fever ceased. The reaction solution was filtered and the filtrate was concentrated to give the title compound (0.71 g, 86%) as oily substances. This compound was used in the subsequent reaction without further purification.

The following compounds of Reference Examples 41, 43, 47, 79, 81, 83, 85, and 87 were prepared according to a manner similar to that in Reference Example 4.

REFERENCE EXAMPLE 41

7-Ethylamino-4-{2-[1-(hydroxymethyl)ethoxy]benzylamino}-6-nitroquinazoline

The title compound was obtained from 4-chloro-7-ethylamino-6-nitroquinazoline obtained in Reference Example 2 and 2-[1-(hydroxymethyl)ethoxy]benzylamine obtained in Reference Example 40.

¹H-NMR (CDCl₃) δ(ppm): 1.37(3H, t, J=7.2 Hz), 1.41 (3H, d, J=6.4 Hz), 3.31(2H, q, J=7.2 Hz), 3.80–3.87(1H, m), 3.97–3.99(1H, m), 4.60–4.75(2H, m), 5.03–5.10(1H, m), 6.83–6.96(3H, m), 7.21–7.26(1H, m), 7.40(1H, d, J=7.9 Hz), 7.45–7.60(1H, br), 7.60–7.65(1H, m), 8.39(1H, s), 8.88(1H, s).

REFERENCE EXAMPLE 42

7-Ethylamino-4-{2-[1-(morpholinomethyl)ethoxy]benzylamino}-6-nitroquinazoline

The title compound was obtained from 7-ethylamino-4-{2-[1-(hydroxymethyl)ethoxy]benzylamino)-6-nitroquinazoline obtained in Reference Example 41 and morpholine.

¹H-NMR (CDCl₃) δ(ppm): 1.30–1.43(6H, m), 2.00–2.20 (2H, m), 2.40–2.60(4H, m), 3.38(2H, m), 3.52–3.70(4H, m), 4.60–4.90(3H, m), 6.85–7.00(3H, m), 7.20–7.41 (2H, m), 7.60–7.70(1H, m), 8.52(1H, s), 8.76(1H, s).

REFERENCE EXAMPLE 43

7-Ethylamino-4-[3-(2-hydroxyethoxy)benzylamino]-6-nitroquinazoline

The title compound was obtained from 4-chloro-7-ethylamino-6-nitroquinazoline obtained in Reference Example 2 and 3-(2-hydroxyethoxy)benzylamine, which is prepared from 3-cyanophenol according to a similar manner as that in Reference Example 26.

¹H-NMR (CDCl₃) δ(ppm): 1.28(3H, t, J=6.9 Hz), 3.34 (2H, q, J=6.9 Hz), 3.70(2H, t, J=4.9 Hz), 3.94(2H, t, J=4.9 Hz), 4.72(2H, d, J=5.4 Hz), 4.75–4.85(1H, m), 6.79–6.85 (2H, m), 6.88–6.94(2H, m), 7.23(1H, dd, J=7.9 Hz, 8.4 Hz), 7.70–7.74(1H, m), 8.32(1H, s), 9.15–9.23(1H, m), 9.28(1H, s).

REFERENCE EXAMPLE 44

7-Ethylamino-4-[3-(2-morpholinoethoxy)benzylamino]-6-nitroquinazoline

The title compound was obtained from 7-ethylamino-4-[3-(2-hydroxyethoxy)benzylamino]-6-nitroquinazoline obtained in Reference Example 43 and morpholine.

¹H-NMR (CDCl₃) δ(ppm): 1.28(3H, t, J=7.2 Hz), 2.46–2.52 (4H, m), 2.70(2H, t, J=5.7 Hz), 3.36(2H, q, J=7.2 Hz), 3.76–3.80(4H, m), 4.07(2H, t, J=5.7 Hz), 4.73(2H, s), 6.81–6.85(2H, m), 6.92–6.95(2H, m), 7.23(1H, dd, J=7.9 Hz, 8.4 Hz), 7.71–7.76(1H, m), 8.33(1H, s), 9.28(1H, s).

REFERENCE EXAMPLE 45

7-Ethylamino-6-nitro-4-[3-(2-piperidinoethoxy)benzylamino]quinazoline

The title compound was obtained from 7-ethylamino-4-[3-(2-hydroxyethoxy)benzylamino]-6-nitroquinazoline obtained in Reference Example 43 and piperidine.

¹H-NMR (CDCl₃) δ(ppm): 1.28(3H, t, J=7.2 Hz), 1.50–1.80 (6H, m), 3.03(2H, t, J=4.9 Hz), 3.30–3.50(6H, m), 4.26(2H, t, J=4.9 Hz), 4.74(2H, d, J=5.4 Hz), 6.87 (1H, s), 6.89(1H, d, J=7.4 Hz), 6.98–7.01(2H, m), 7.28(1H, dd, J=7.4 Hz, 7.9 Hz), 7.74–7.78(1H, m), 8.34(1H, s), 9.24–9.29(2H, m).

REFERENCE EXAMPLE 46

4-{3-[2-(Diethylamino)ethoxy]benzylamino}-7-ethylamino-6-nitroquinazoline

The title compound was obtained from 7-ethylamino-4-[3-(2-hydroxyethoxy)benzylamino]-6-nitroquinazoline obtained in Reference Example 43 and diethylamine.

¹H-NMR (CDCl₃) δ(ppm): 1.36–1.51(9H, m), 3.30–3.43 (6H, m), 3.57(2H, t, J=4.7 Hz), 4.48(2H, t, J=4.7 Hz), 4.82(2H, s), 6.83(1H, dd, J=2.5 Hz, 7.9 Hz), 6.95 (1H, s), 7.06(1H, dd, J=2.5 Hz, 7.4 Hz), 7.15(1H, s), 7.22(1H, dd, J=7.4 Hz, 7.9 Hz), 7.72–7.75(1H, m), 8.44(1H, s), 9.16(1H, s).

REFERENCE EXAMPLE 47

7-Ethylamino-4-[4-(2-hydroxyethoxy)benzylamino]-6-nitroquinazoline

The title compound was obtained from 4-chloro-7-ethylamino-6-nitroquinazoline obtained in Reference Example 2 and 4-(2-hydroxyethoxy)benzylamine, which is prepared from 4-cyanophenol according to a similar manner as that in Reference Example 26.

$^1$H-NMR (DMSO-d$_6$) δ(ppm): 1.26(3H, t, J=7.1 Hz), 3.35(2H, q, J=7.1 Hz), 3.69–3.72(2H, m), 3.95(2H, t, J=5.0 Hz), 4.67(2H, d, J=5.3 Hz), 4.86(1H, t, J=5.4 Hz), 6.84(1H, s), 6.89(2H, d, J=8.4 Hz), 7.29 (2H, d, J=8.4 Hz), 7.73(1H, br), 8.33(1H, s), 9.18 (1H, br), 9.26(1H, s).

REFERENCE EXAMPLE 48

7-Ethylamino-4-[4-(2-morpholinoethoxy)benzylamino]-6nitroquinazoline

The title compound was obtained from 7-ethylamino-[4-(2-hydroxyethoxy)benzylamino]-6-nitroquinazoline obtained in Reference Example 47 and morpholine.

$^1$H-NMR (DMSO-d$_6$) δ(ppm): 1.29(3H, t, J=7.1 Hz), 2.47–2.51 (4H, m), 2.69(2H, t, J=5.8 Hz), 3.39(2H, q, J=7.1 Hz), 3.56–3.59(4H, m), 4.05(2H, t, J=5.8 Hz), 4.68(2H, d, J=5.3 Hz), 6.86(1H, s), 6.88(2H, d, J=8.3 Hz), 7.28(2H, d, J=8.3 Hz), 7.72–7.76(1H, m), 8.33(1H, s), 9.10–9.15(1H, m), 9.28(1H, s).

REFERENCE EXAMPLE 49

7-Ethylamino-6-nitro-4-[2-(4-Phenylpiperazin-1-ylmethyl)benzylamino]quinazoline The title compound was obtained from 7-ethylamino-[2-(hydroxymethyl)benzylamino]-6-nitroquinazoline obtained in Reference Example 4 and 1-phenylpiperazine.

$^1$H-NM$_{(CDCl_3)}$ δ(ppm): 1.36(3H, t, J=7.3 Hz), 2.70–2.75 (4H, m), 3.15–3.19(4H, m), 3.34(2H, q, J=7.3 Hz), 3.66(2H, s), 4.87(2H, d, J=5.0 Hz), 6.82–6.88(2H, m), 6.93(1H, s), 7.21–7.38(7H, m), 7.50–7.57(1H, m), 7.85–7.90(1H, m), 8.55(1H, s), 8.65(1H, s).

REFERENCE EXAMPLE 50

4-{2-[4-(2-Chlorophenyl)piperazin-1-ylmethyl]benzylamino}-7-ethylamino-6-nitroquinazoline The title compound was obtained from 7-ethylamino-4-[2-(hydroxymethyl)benzylamino]-6-nitroquinazoline obtained in Reference Example 4 and 1-(2-chlorophenyl)piperazine.

$^1$H-NMR (CDCl$_3$) δ(ppm): 1.38(3H, t, J=7.3 Hz), 2.74–2.78 (4H, m), 3.04–3.07(4H, m), 3.35(2H, q, J=7.3 Hz), 3.68(2H, s), 4.86(2H, d, J=5.0 Hz), 6.93–6.98(3H, m), 7.15–7.38(5H, m), 7.55–7.60 (1H, m), 7.60–7.67 (1H, m), 7.90–7.99(1H, m), 8.56(1H, s), 8.73(1H, s).

REFERENCE EXAMPLE 51

7-Ethylamino-4-{2-[4-(2-methoxyphenyl)piperazin-1-ylmethyl]benzylamino}-6-nitroquinazoline The title compound was obtained from 7-ethylamino-4-[2-(hydroxymethyl)benzylamino]-6-nitroquinazoline obtained in Reference Example 4 and 1-(2-methoxyphenyl)piperazine.

$^1$NMR (CDCl$_3$) δ(ppm): 1.38(3H, m), 2.74–2.83(4H, m), 3.00–3.10(4H, m), 3.34(2H, m), 3.67(2H, s), 3.83 (3H, s), 4.86(2H, d, J=5.0 Hz), 6.82–7.00(5H, m), 7.27–7.45(3H, m), 7.50–7.56(1H, m), 7.60(1H, br), 8.56(1H, s), 8.73(1H, s).

REFERENCE EXAMPLE 52

7-Ethylamino-6-nitro-4-{2-[(1-pyrrolidinyl)methyl]benzylamino}quinazoline

The title compound was obtained from 7-ethylamino-4-[2-(hydroxymethyl)benzylamino]-6-nitroquinazoline obtained in Reference Example 4 and pyrrolidine. $^1$H-NMR (CDCl$_3$) δ(ppm): 1.39(3H, t, J=7.3 Hz), 1.85–1.97 (4H, m), 2.63–2.72(4H, m), 3.36(2H, q, J=7.3 Hz), 3.72(2H, s), 4.86(2H, s), 6.94(1H, s), 7.24–7.33 (3H, m), 7.43–7.53(2H, m), 7.60–7.70(1H, m), 8.49 (1H, s), 8.53(1H, s).

REFERENCE EXAMPLE 53

7-Ethylamino-4-[2-(4-ethylpiperazin-1-ylmethyl)benzylamino]-6-nitroquinazoline The title compound was obtained from 7-ethylamino-4-[2-(hydroxymethyl)benzylamino]-6-nitroquinazoline obtained in Reference Example 4 and 1-ethylpiperazine.

$^1$H-NMR (CDCl$_3$) δ(ppm): 1.07(3H, t, J=7.3 Hz), 1.41 (3H, t, J=7.1 Hz), 2.36(2H, q, J=7.3 Hz), 2.40–2.62(8H, m), 3.37(2H, q, J=7.1 Hz), 3.60(2H, s), 4.85(2H, d, J=5.0 Hz), 6.96(1H, s), 7.25–7.33(3H, m), 7.54–7.57 (1H, m), 7.65(1H, br), 7.87(1H, br), 8.56(1H, s), 8.67(1H, s).

REFERENCE EXAMPLE 54

4-{2-[Bis(2-hydroxyethyl)aminomethyl]benzylamino}-7-ethylamino-6-nitroquinazoline The title compound was obtained from 7-ethylamino-4-[2-(hydroxymethyl)benzylamino]-6-nitroquinazoline obtained in Reference Example 4 and diethanolamine.

$^1$H-NMR (CDCl$_3$) δ(ppm): 1.37(3H, t, J=7.1 Hz), 2.77–2.81 (4H, m), 3.31(2H, q, J=7.1 Hz), 3.69–3.74(4H, m), 3.85(2H, s), 4.99(2H, d, J=5.6 Hz), 6.82(1H, s), 7.23–7.31(3H, m), 7.52–7.58(2H, m), 7.95(1H, br), 8.41 (1H, s), 8.88(1H, s).

REFERENCE EXAMPLE 55

7-Ethylamino-4-[2-(4-methylhexahydro-1H-1,4-diazepin-1-ylmethyl)benzylamino]-6-nitroquinazoline The title compound was obtained from 7-ethylamino-4-[2-(hydroxymethyl)benzylamino]-6-nitroquinazoline obtained in Reference Example 4 and 1-methylhomopiperazineo $^1$H-NMR (CDCl$_3$) δ(ppm): 1.35–1.42(3H, m), 2.10–2.18 (2H, m), 2.67(3H, s), 2.97–3.03(2H, m), 3.08–3.10(4H, m), 3.12–3.18(2H, m), 3.32–3.36(2H, m), 3.82(2H, s), 4.95(2H, s), 6.88(1H, s), 7.24–7.28(3H, m), 7.30(1H, s), 7.41–7.45 (1H, m), 7.63–7.69(1H, m), 8.44(1H, s), 8.76(1H, s).

REFERENCE EXAMPLE 56

7-Ethylamino-4-[2-(hexahydroazepinomethyl)benzylamino]-6-nitroquinazoline

The title compound was obtained from 7-ethylamino-4-[2-(hydroxymethyl)benzylamino]-6-nitroquinazoline obtained in Reference Example 4 and homopiperidine.

$^1$H-NMR (DMSO-d$_6$) δ(ppm): 1.27(3H, t, J=7.1 Hz), 1.58(8H, br), 2.59(4H, m), 3.34–3.48(2H, q, J=7.1 Hz), 3.69 (2H, s), 4.91(2H, d, J=5.3 Hz), 6.87(1H, s), 7.19–7.28(4H, m), 7.77(1H, t, J=5.3 Hz), 8.31(1H, s), 9.16(1H, t, J=5.6 Hz), 9.24(1H, s).

REFERENCE EXAMPLE 57

4-{2-[(1-Butylamino)methyl]benzylamino}-7-ethylamino-6-nitroquinazoline

The title compound was obtained from 7-ethylamino-4-[2-(hydroxymethyl)benzylamino]-6-nitroquinazoline obtained in Reference Example 4 and 1-butylamine.

¹H-NMR (DMSO-d₆) δ(ppm): 0.84(3H, t, J=7.3 Hz), 1.26(3H, t, J=7.1 Hz), 1.27–1.40(2H, m), 1.60–1.70(2H, m), 3.06(2H, t, J=7.6 Hz), 3.40(2H, q, J=7.1 Hz), 4.36 (2H, s), 4.80(2H, s), 6.89(1H, s), 7.35–7.54(4H, m), 7.80(1H, t, J=5.4 Hz), 8.32(1H, s), 8.84(1H, br), 9.30(1H, s).

REFERENCE EXAMPLE 58

4-{4-[(Diethylamino)methyl]benzylamino}-7-ethylamino-6-nitroquinazoline

The title compound was obtained from 7-ethylamino-4-[4-(hydroxymethyl)benzylamino]-6-nitroquinazoline obtained in Reference Example 6 and diethylamine.

¹H-NMR (CDCl₃) δ(ppm): 1.50–1.56(9H, m), 3.10–3.30 (6H, m), 4.32(2H, s), 4.91(2H, s), 6.94(1H, s), 7.32 (1H, s), 7.56(2H, d, J=7.9 Hz), 7.66(2H, d, J=7.9 Hz), 8.45(1H, s), 9.29(1H, s).

REFERENCE EXAMPLE 59

2-(3-Piperidinopropoxy)benzylamine

According to a similar manner as that in Reference Example 36 except that 2-cyanophenol, 1-bromo-3-chloropropane, and piperidine were used, 2-(3-piperidinopropoxy)benzonitrile (77%) was obtained as a crude product.

¹H-NMR (CDCl₃) δ(ppm): 1.40–1.50(2H, m), 1.50–1.62 (4H, m), 1.92–2.08(2H, m), 2.25–2.40(4H, m), 2.51(2H, t, J=7.3 Hz), 4.13(2H, t, J=6.3 Hz), 6.95–7.08(2H, m), 7.48–7.57(2H, m).

According to a similar manner as that in Reference Example 36, the crude product of 2-(3-piperidinopropoxy) benzonitrile obtained above was reduced by lithium aluminium hydride to give the title compound (83%) as a crude product. This compound was used in the subsequent reaction without further purification.

REFERENCE EXAMPLE 60

7-Ethylamino-6-nitro-4-[2-(3-piperidinopropoxy) benzylamino]quinazoline

The title compound was obtained from 4-chloro-7-ethylamino-6-nitroquinazoline obtained in Reference Example 2 and 2-(3-piperidinopropoxy)benzylamine obtained in Reference Example 59.

¹H-NMR (CDCl₃) δ(ppm): 1.39(3H, t, J=7.1 Hz), 1.52–1.65 (2H, m), 1.90–2.10(6H, m), 2.50–2.60(4H, m), 3.10–3.17(2H, m), 3.38(2H, q, J=7.1 Hz), 4.10(2H, t, J=5.3 Hz), 4.81(2H, d, J=5.3 Hz), 6.84(1H, d, J=8.3 Hz), 6.92–6.99(2H, m), 7.23–7.28(1H, m), 7.55(1H, d, J=7.6 Hz), 7.64(1H, br), 8.47(1H, s), 9.16(1H, s).

REFERENCE EXAMPLE 61

2-[3-(Diethylamino)propoxy]benzylamine

According to a similar manner as that in Reference Example 36 except that 2-cyanophenol, 1-bromo-3-chloropropane, and diethylamine were used, 2-[3-(diethylamino)propoxy]benzonitrile (95%) was obtained as a crude product.

¹H-NMR (CDCl₃) δ(ppm): 1.02(6H, t, J=7.2 Hz), 1.92–2.02 (2H, m), 2.53(4H, q, J=7.2 Hz), 2.64(2H, t, J=6.9 Hz), 4.14(2H, t, J=6.2 Hz), 6.95–7.00(2H, m), 7.47–7.56 (2H, m).

According to a similar manner as that in Reference Example 36, the crude product of 2-[3-(diethylamino) propoxy]benzonitrile obtained above was reduced by lithium aluminium hydride to give the title compound (99%) as a crude product. This compound was used in the subsequent reaction without further purification.

REFERENCE EXAMPLE 62

4-{2-[3-(Diethylamino)propoxy]benzylamino}-7-ethylamino-6-nitroquinazoline

The title compound was obtained from 4-chloro-7-ethylamino-6-nitroquinazoline obtained in Reference Example 2 and 2-[3-(diethylamino)propoxy]benzylamine obtained in Reference Example 61.

¹H-NMR (CDCl₃) δ(ppm): 0.98(6H, t, J=7.1 Hz), 1.39 (3H, t, J=7.1 Hz), 1.98–2.05(2H, m), 2.52(4H, q, J=7.1 Hz), 2.64(2H, t, J=7.2 Hz), 3.36(2H, q, J=7.1 Hz), 4.12 (2H, t, J=6.3 Hz), 4.86(2H, d, J=5.6 Hz), 6.63(1H, br), 6.91–6.98 (3H, m), 7.25–7.37(2H, m), 7.68(1H, br), 8.52(1H, s), 8.69(1H, s).

REFERENCE EXAMPLE 63

4-{4-[2-(Diethylamino)ethoxy]benzylamino}-7-ethylamino-6-nitroquinazoline

The title compound was obtained from 7-ethylamino-4-[4-(2-hydroxyethoxy)benzylamino]-6-nitroquinazoline obtained in Reference Example 47 and diethylamine.

¹H-NMR (CDCl₃) δ(ppm): 1.30–1.50(9H, m), 2.99–3.15 (4H, m), 3.28–3.40(4H, m), 4.33(2H, t, J=5.2 Hz), 4.77 (2H, s), 6.82(2H, d, J=8.9 Hz), 6.98(1H, s), 7.32 (2H, d, J=8.9 Hz), 7.66(1H, br), 8.50(1H, s), 8.98 (1H, s).

REFERENCE EXAMPLE 64

7-Ethylamino-6-nitro-4-[4-(2-piperidinoethoxy) benzylamino]quinazoline

The title compound was obtained from 7-ethylamino-4-[4-(2-hydroxyethoxy)benzylamino]-6-nitroquinazoline obtained in Reference Example 47 and piperidine.

¹H-NMR (CDCl₃) δ(ppm): 1.40(3H, t, J=7.1 Hz), 1.52–1.65 (2H, m), 1.81–1.88(4H, m), 3.05–3.15(4H, m), 3.28 (2H, t, J=5.0 Hz), 3.37(2H, q, J=7.1 Hz), 4.46(2H, t, J=5.0 Hz), 4.78(2H, br), 6.88(2H, d, J=8.6 Hz), 6.99(1H, s), 7.34(2H, d, J=8.6 Hz), 7.67(1H, br), 8.53(1H, s), 8.79(1H, s).

REFERENCE EXAMPLE 65

7-Ethylamino-4-{4-[2-(4-methylpiperazin-1-yl) ethoxy]benzylamino}-6-nitroquinazoline The title compound was obtained from 7-ethylamino-4-[4-(2-hydroxyethoxy)benzylamino]-6-nitroquinazoline obtained in Reference Example 47 and 1-methylpiperazine.

¹H-NMR (DMSO-d₆) δ(ppm): 1.29(3H, t, J=7.1 Hz), 2.25(3H, s), 2.50–2.60(8H, m), 2.68(2H, t, J=5.3 Hz), 3.38 (2H, q, J=7.1 Hz), 4.07(2H, t, J=5.3 Hz), 4.68(2H, s), 6.86(1H, s), 6.89(2H, d, J=8.7 Hz), 7.30(2H, d, J=8.7 Hz), 7.75(1H, br), 8.33(1H, s), 9.27(1H, s).

REFERENCE EXAMPLE 66

7-Ethylamino-4-{4-[2-(4-ethylpiperazin-1-yl) ethoxy]benzylamino}-6-nitroquinazoline The title compound was obtained from 7-ethylamino-4-[4-(2-hydroxyethoxy)benzylamino]-6-nitroquinazoline obtained in Reference Example 47 and 1-ethylpiperazine.

$^1$H-NMR (DMSO-d$_6$) δ(ppm): 1.00(3H, t, J=7.3 Hz), 1.26(3H, t, J=7.1 Hz), 2.28–2.73(12H, m), 3.38(2H, q, J=7.1 Hz), 4.04(2H, t, J=5.6 Hz), 4.67(2H, d, J=5.6 Hz), 6.86(1H, s), 6.89(2H, d, J=8.6 Hz), 7.28 (2H, d, J=8.6 Hz), 7.76(1H, t, J=5.1 Hz), 8.33(1H, s), 9.19(1H, t, J=5.6 Hz), 9.27(1H, s).

REFERENCE EXAMPLE 67

7-Ethylamino-4-{4-{2-[4-(2-hydroxyethyl)piperazin-1-yl]ethoxy}benzylamino}-6-nitroquinazoline The title compound was obtained from 7-ethylamino-4-[4-(2-hydroxyethoxy)benzylamino]-6-nitroquinazoline obtained in Reference Example 47 and 1-(2-hydroxyethyl)piperazine.

$^1$H-NMR (DMSO-d$_6$) δ(ppm): 1.26(3H, t, J=7.1 Hz), 2.36–2.71 (12H, m), 3.48–3.56(4H, m), 4.04(2H, t, J=5.6 Hz), 4.67(2H, d, J=5.6 Hz), 6.86(1H, s), 6.89(2H, d, J=8.6 Hz), 7.28(2H, d, J=8.6 Hz), 7.75(1H, t, J=5.6 Hz), 8.33(1H, s), 9.20(1H, t, J=5.3 Hz), 9.27 (1H, s).

REFERENCE EXAMPLE 68

7-Ethylamino-6-nitro-4-{4-[2-(1-pyrrolidinyl)ethoxy]benzylamino}quinazoline

The title compound was obtained from 7-ethylamino-4-[4-(2-hydroxyethoxy)benzylamino]-6-nitroquinazoline obtained in Reference Example 47 and pyrrolidine.

$^1$H-NMR (DMSO-d$_6$) δ(ppm): 1.26(3H, t, J=7.1 Hz), 1.72–1.77 (4H, m), 2.75–2.85(4H, m), 3.03(2H, m), 3.42 (2H, q, J=7.1 Hz), 4.10(2H, t, J=5.4 Hz), 4.67(2H, d, J=5.6 Hz), 6.86(1H, s), 6.92(2H, d, J=8.6 Hz), 7.30 (2H, d, J=8.6 Hz), 7.76(1H, t, J=5.3 Hz), 8.33(1H, s), 9.20(1H, t, J=5.6 Hz), 9.27(1H, s).

REFERENCE EXAMPLE 69

4-[3-(Diethylamino)propoxy]benzylamine

According to a similar manner as that in Reference Example 36 except that 4-cyanophenol, 1-bromo-3-chloropropane, and diethylamine were used, 4-[3-(diethylamino)propoxy]benzonitrile (100%) was obtained as a crude product.

According to a similar manner as that in Reference Example 36, the crude product of 4-[3-(diethylamino)propoxy]benzonitrile obtained above was reduced by lithium aluminium hydride to give the title compound (95%) as a crude product. This compound was used in the subsequent reaction without further purification.

REFERENCE EXAMPLE 70

4-{4-[3-(Diethylamino)propoxy]benzylamino}-7-ethylamino-6-nitroquinazoline

The title compound was obtained from 4-chloro-7-ethylamino-6-nitroquinazoline obtained in Reference Example 2 and 4-[3-(diethylamino)propoxy]benzylamine obtained in Reference Example 69.

$^1$H-NMR (DMSO-d$_6$) δ(ppm): 1.17–1.29(9H, m), 2.08–2.17(2H, m), 3.04–3.19(6H, m), 3.38(2H, q, J=7.1 Hz), 4.04 (2H, t, J=5.9 Hz), 4.68(2H, d, J=5.6 Hz), 6.86(1H, s), 6.90(2H, d, J=8.6 Hz), 7.31(2H, d, J=8.6 Hz), 7.77(1H, t, J=5.4 Hz), 8.34(1H, s), 9.27(1H, t, J=5.6 Hz), 9.29(1H, s).

REFERENCE EXAMPLE 71

4-[4-(Diethylamino)butoxy]benzylamine

According to a similar manner as that in Reference Example 36 except that 4-cyanophenol, 1-bromo-4-chlorobutane, and diethylamine were used, 4-[4-(diethylamino)butoxy]benzonitrile (94%) was obtained as a crude product.

According to a similar manner as that in Reference Example 36, the crude product of 4-[4-(diethylamino)butoxy]benzonitrile obtained above was reduced by lithium aluminium hydride to give the title compound (99%) as a crude product. This compound was used in the subsequent reaction without further purification.

REFERENCE EXAMPLE 72

4-{4-[4-(Diethylamino)butoxy]benzylamino}-7-ethylamino-6-nitroquinazoline

The title compound was obtained from 4-chloro-7-ethylamino-6-nitroquinazoline obtained in Reference Example 2 and 4-[4-(diethylamino)butoxy]benzylamine obtained in Reference Example 71.

$^1$H-NMR (DMSO-d$_6$) δ(ppm): 1.15–1.29(9H, m), 1.75 (4H, br), 3.00–3.18(6H, m), 3.35–3.43(2H, m), 3.97(2H, br), 4.67(2H, d, J=5.6 Hz), 6.85(1H, s), 6.90(2H, d, J=8.5 Hz), 7.30(2H, d, J=8.5 Hz), 7.75(1H, t, J=5.6 Hz), 8.33(1H, s), 9.25(1H, t, J=5.3 Hz), 9.29 (1H, s).

REFERENCE EXAMPLE 73

7-Ethylamino-6-nitro-4-[2-(1,2,3,6-tetrahydropyridin-1-ylmethyl)benzylamino]quinazoline 7-Ethylamino-4-[2-(hydroxymethyl)benzylamino]-6-nitroquinazoline (6.04 g, 17.1 mmol) obtained in Reference Example 4 was dissolved in N,N-dimethylformamide (70 ml), and 2,6-lutidine (2.99 ml, 25.7 mmol) and methanesulfonyl chloride (1.99 ml, 25.7 mmol) were added thereto, followed by stirring at room temperature for 40 minutes. After the reaction, a large amount of a saturated aqueous solution of sodium bicarbonate and ice were added to the reaction mixture, and the precipitated solid was collected by filtration followed by drying (5.11 g).

The solid (5.11 g) obtained above was dissolved in N,N-dimethylformamide (150 ml), 1,2,3,6-tetrahydropyridine (1.88 ml, 20.6 mmol) was added thereto, and further triethylamine (9.50 ml, 68.2 mmol) and sodium iodide (4.11 g, 27.4 mmol) were added, followed by stirring at room temperature for 4.5 hours. After the reaction, the reaction mixture was concentrated under reduced pressure, water was added to the residue, and the mixture was extracted with chloroform. The organic layer was dried over anhydrous magnesium sulfate, the drying agent was filtered off, and the filtrate was concentrated under reduced pressure. The obtained oily substances were purified by silica gel column chromatography (eluent: chloroform/hexane=1–chloroform/methanol=100) to give the title compound (3.89 g, 54%) as oily substances.

$^1$H-NMR (CDCl$_3$) δ(ppm): 1.37(3H, t, J=7.3 Hz), 2.18–2.22 (2H, m), 2.74–2.79(2H, m), 3.02–3.05(2H, m), 3.33 (2H, q, J=7.3 Hz), 3.67(2H, s), 4.83(2H, s), 5.58 (1H, d, J=9.9 Hz), 5.76(1H, d, J=9.9 Hz), 6.89(1H, s), 7.26–7.32 (2H, m), 7.54–7.58(2H, m), 8.42(1H, s), 8.52(1H, s).

The following compounds of Reference Examples 74, 76, 77, and 88 were prepared according to a manner similar to that in Reference Example 73.

REFERENCE EXAMPLE 74

7-Ethylamino-4-{2-{4-[2-(2-hydroxyethoxy)ethyl]piperazin-1-ylmethyl}benzylamino}-6-nitroquinazoline The title compound was obtained from 7-ethylamino-4-[2-(hydroxymethyl)benzylamino]-6-nitroquinazoline obtained in Reference Example 4 and 1-[2-(2-hydroxyethoxy)ethyl]piperazine.

¹H-NMR (CDCl₃) δ(ppm): 1.39(3H, t, J=7.2 Hz), 2.17 (2H, s), 2.50–2.70(8H, m), 3.37(2H, q, J=7.2 Hz), 3.47–3.71 (8H, m), 4.85(2H, d, J=4.5 Hz), 6.97(1H, s), 7.24–7.35(3H, m), 7.55(1H, d, J=8.4 Hz), 7.65(1H, br), 7.86(1H, br), 8.55(1H, s), 8.67(1H, s).

The following compound of Reference Examples 75 was prepared according to a manner similar to that in Reference Example 20.

REFERENCE EXAMPLE 75

7-Ethylamino-4-{2-{4-[(isopropylcarbamoyl)methyl]piperazin-1-ylmethyl}benzylamino}-6-nitroquinazoline The title compound was obtained from 7-ethylamino-4-[2-(hydroxymethyl)benzylamino]-6-nitroquinazoline obtained in Reference Example 4 and N-isopropyl-1-piperazineacetamide.

¹H-NMR (CDCl₃) δ(ppm): 1.16(3H, d, J=6.3 Hz), 1.18 (3H, d, J=6.6 Hz), 1.40(3H, t, J=7.3 Hz), 2.60–2.80(6H, m), 3.01(2H, br), 3.32–3.43(4H, m), 3.66 (2H, s), 4.04–4.15(1H, m), 4.86(2H, d, J=5.0 Hz), 6.97(1H, s), 6.98–7.02(1H, m), 7.24–7.37(3H, m), 7.53–7.57(1H, m), 7.68(1H, br), 7.99 (1H, br), 8.55(1H, s), 8.66 (1H, s).

REFERENCE EXAMPLE 76

7-Ethylamino-4-{2-[4-(3,4-methylenedioxybenzyl)piperazin-1-ylmethyl]benzylamino}-6-nitroquinazoline The title compound was obtained from 7-ethylamino-[2-(hydroxymethyl)benzylamino]-6-nitroquinazoline obtained in Reference Example 4 and 1-piperonylpiperazine.

¹H-NMR (CDCl₃) δ(ppm): 1.41(3H, t, J=7.1 Hz), 2.40–2.50 (4H, m), 2.52–2.60(4H, m), 3.35(2H, s), 3.39(2H, q, J=7.1 Hz), 3.59(2H, s), 4.83(2H, d, J=5.0 Hz), 5.92(2H, s), 6.70–6.78(2H, m), 6.86(1H, s), 6.98 (1H, s), 7.22–7.35 (3H, m), 7.57(1H, dd, J=2,3 Hz, 6.3 Hz), 7.65–7.69(1H, m), 7.94(1H, br), 8.56(1H, s), 8.70(1H, s).

REFERENCE EXAMPLE 77

7-Ethylamino-4-{2-[4-(ethoxycarbonyl)piperidin-1-ylmethyl]benzylamino}-6-nitroquinazoline The title compound was obtained from 7-ethylamino-4-[2-(hydroxymethyl)benzylamino]-6-nitroquinazoline obtained in Reference Example 4 and ethyl isonipecotate.

¹H-NMR (DMSO-d₆) δ(ppm): 1.17(3H, t, J=7.1 Hz), 1.29(3H, t, J=7.1 Hz), 1.50–1.58(2H, m), 1.75–1.78(2H, m), 1.98–2.06(2H, m), 2.22–2.28(1H, m), 2.75–2.77(2H, m), 3.37(2H, q, J=7.1 Hz), 3.54(2H, s), 4.04(2H, q, J=7.1 Hz), 4.88(2H, d, J=5.3 Hz), 6.86(1H, s), 7.19–7.33(4H, m), 7.76(1H, t, J=5.3 Hz), 8.32(1H, s), 9.02(1H, s), 9.28(1H, s).

REFERENCE EXAMPLE 78

3-(3-Morpholinopropoxy)benzylamine

3-Cyanophenol (6.70 g, 5.62 mmol) was dissolved N,N-dimethylformamide (50 ml), followed by stirring under ice-cooling in an argon atmosphere. 60% Sodium hydride (2.70 g, 6.73 mmol) was added thereto followed by stirring for one hour, 1-bromo-3-chloropropane (6.7 ml, 6.73 mmol) was added to the mixture, and the mixture was stirred elevating gradually the temperature from under ice-cooling to at room temperature for one night. After the reaction, water was added to the reaction mixture, and the mixture was extracted with ether. The organic layer was dried over anhydrous magnesium sulfate, the drying agent was filtered off, and the filtrate was concentrated under reduced pressure to give oily substances.

A half of the oily substances obtained above was dissolved in N,N-dimethylformamide (13 ml), and morpholine (9.9 ml, 11.3 mmol) and sodium iodide (2 g, 13.3 mmol) were added thereto, followed by stirring at room temperature for one night. After the reaction, water was added to the reaction mixture and the mixture was extracted with ether. The organic layer was dried over anhydrous magnesium sulfate, the drying agent was filtered off, and the filtrate was concentrated under reduced pressure to give oily substances. The obtained oily substances were purified by silica gel column chromatography (eluent: chloroform/methanol= 100) to give 3-(3-morpholinopropoxy)benzonitrile (6.00 g, 87%).

¹H-NMR (CDCl₃) δ(ppm): 1.93–2.03(2H, m), 2.45–2.54 (6H, m), 3.70–3.78(4H, m), 4.05(2H, t, J=6.4 Hz), 7.11–7.15 (2H, m), 7.22(1H, d, J=7.6 Hz), 7.36(1H, dd, J=7.6 Hz, 7.6 Hz).

Lithium aluminium hydride (1.85 g, 48.7 mmol) was suspended in dried tetrahydrofuran (50 ml), and a solution of 3-(3-morpholinopropoxy)benzonitrile (4.00 g, 16.3 mmol) obtained above dissolved in dried tetrahydrofuran (25 ml) was added thereto under ice-cooling in an argon atmosphere, followed by stirring for one hour under heating at reflux. After the reaction, the solution was ice-cooled and sodium sulfate 10 hydrate was portionwise added thereto until foaming ceased. The reaction solution was filtered and the filtrate was concentrated to give the title compound (3.9 g, 96%). This compound was used in the subsequent reaction without further purification.

REFERENCE EXAMPLE 79

7-Ethylamino-4-[3-(3-morpholinopropoxy)benzylamino]-6-nitroquinazoline

The title compound was obtained from 4-chloro-7-ethylamino-6-nitroquinazoline obtained in Reference Example 2 and 3-(3-morpholinopropoxy)benzylamine obtained in Reference Example 78.

¹H-NMR (CDCl₃) δ(ppm): 1.42(3H, t, J=7.9 Hz), 1.93–2.00(2H, m), 2.45–2.55(6H, m), 3.37(2H, q, J=7.9 Hz), 3.70–3.74(4H, m), 4.01(2H, t, J=6.4 Hz), 4.83(2H, d, J=5.6 Hz), 6.82(1H, dd, J=2,3 Hz, 7.9 Hz), 6.94–7.03(4H, m), 7.29(1H, s), 7.67(1H, br), 8.51(1H, s), 8.91 (1H, s).

REFERENCE EXAMPLE 80

3-[3-(Diethylamino)propoxy]benzylamine

According to a similar manner as that in Reference Example 78 except that 3-cyanophenol, 1-bromo-3-chloropropane, and diethylamine were used, 3-[3-(diethylamino)propoxy]benzonitrile (54%) was obtained as a crude product.

¹H-NMR (CDCl₃) δ(ppm): 1.03(6H, t, J=7.3 Hz), 1.89–2.00 (2H, m), 2.51–2.66(6H, m), 4.03(2H, t, J=6.3 Hz), 7.11–7.14(2H, m), 7.21(1H, d, J=7.3 Hz), 7.37(1H, dd, J=6.0 Hz, 7.6 Hz).

According to a similar manner as that in Reference Example 78, 3-[3-(diethylamino)propoxy]benzonitrile obtained above was reduced by lithium aluminium hydride to give the title compound (89%). This compound was used in the subsequent reaction without further purification.

REFERENCE EXAMPLE 81

4-{3-[3-(Diethylamino)propoxy]benzylamino}-7-ethylamino-6-nitroquinazoline

The title compound was obtained from 4-chloro-7-ethylamino-6-nitroquinazoline obtained in Reference Example 2 and 3-[3-(diethylamino)propoxy]benzylamine obtained in Reference Example 80.

$^1$H-NMR (CDCl$_3$) δ(ppm): 1.21(6H, t, J=7.9 Hz), 1.42 (3H, t, J=7.9 Hz), 2.05–2.18(2H, m), 2.80–2.95(6H, m), 3.37 (2H, q, J=7.9 Hz), 4.01(2H, t, J=6.4 Hz), 4.83(2H, d, J=5.6 Hz), 6.82(1H, dd, J=2.3 Hz, 7.9 Hz), 6.95–7.00(3H, m), 7.05–7.10(2H, m), 7.62(1H, br), 8.51 (1H, s), 8.91(1H, s).

REFERENCE EXAMPLE 82

4-(3-Morpholinopropoxy)benzylamine

According to a similar manner as that in Reference Example 78 except that 4-cyanophenol, 1-bromo-3-chloropropane, and morpholine were used, 4-(3-morpholinopropoxy)benzonitrile (quantitative) was obtained as a crude product.

According to a similar manner as that in Reference Example 78, 4-(3-morpholinopropoxy)benzonitrile obtained above was reduced by lithium aluminium hydride to give the title compound (100%). This compound was used in the subsequent reaction without further purification.

REFERENCE EXAMPLE 83

7-Ethylamino-4-[4-(3-morpholinopropoxy)benzylamino]-6-nitroquinazoline

The title compound was obtained from 4-chloro-7-ethylamino-6-nitroquinazoline obtained in Reference Example 2 and 4-(3-morpholinopropoxy)benzylamine obtained in Reference Example 82.

$^1$H-NMR (DMSO-d$_6$) δ(ppm): 1.26(3H, t, J=6.9 Hz), 1.81–1.86(2H, m), 2.34–2.42(6H, m), 3.40(2H, q, J=6.9 Hz), 3.53–3.57(4H, m), 3.96(2H, t, J=6.3 Hz), 4.67(2H, d, J=5.6 Hz), 6.86(1H, s), 6.88(2H, d, J=8.6 Hz), 7.28(2H, d, J=8.6 Hz), 7.45(1H, t, J=6.9 Hz), 8.33 (1H, s), 9.17(1H, t, J=5.6 Hz), 9.27(1H, s).

REFERENCE EXAMPLE 84

4-(4-Morpholinobutoxy)benzylamine

According to a similar manner as that in Reference Example 78 except that 4-cyanophenol, 1-bromo-4-chlorobutane, and morpholine were used, 4-(4-morpholinobutoxy)benzonitrile (86%) was obtained as a crude product.

According to a similar manner as that in Reference Example 78, 4-(4-morpholinobutoxy)benzonitrile obtained above was reduced by lithium aluminium hydride to give the title compound (88%). This compound was used in the subsequent reaction without further purification.

REFERENCE EXAMPLE 85

7-Ethylamino-4-[4-(4-morpholinobutoxy)benzylamino]-6-nitroquinazoline

The title compound was obtained from 4-chloro-7-ethylamino-6-nitroquinazoline obtained in Reference Example 2 and 4-(4-morpholinobutoxy)benzylamine obtained in Reference Example 84.

$^1$H-NMR (DMSO-d$_6$) δ(ppm): 1.25(3H, t, J=7.1 Hz), 1.42–1.78(4H, m), 2.21–2.36(6H, m), 3.36(2H, q, J=7.1 Hz), 3.53–3.56 (4H, m), 3.96(2H, t, J=6.4 Hz), 4.96(2H, s), 6.86(1H, s), 6.93(2H, d, J=8.6 Hz), 7.26(2H, d, J=8.6 Hz), 7.71(1H, br), 8.36(1H, s), 8.89(1H, s).

REFERENCE EXAMPLE 86

4-[4-(Diethylamino)butoxy]benzylamine

According to a similar manner as that in Reference Example 78 except that 4-cyanophenol, 1-bromo-4-chlorobutane, and diethylamine were used, 4-[4-(diethylamino)butoxy]benzonitrile (quantitative) was obtained as a crude product.

According to a similar manner as that in Reference Example 78, 4-[4-(diethylamino)butoxy]benzonitrile obtained above was reduced by lithium aluminium hydride to give the title compound (quantitative). This compound was used in the subsequent reaction without further purification.

REFERENCE EXAMPLE 87

4-{4-[4-(Diethylamino)butoxy]benzylamino}-7-ethylamino-6-nitroquinazoline

The title compound was obtained from 4-chloro-7-ethylamino-6-nitroquinazoline obtained in Reference Example 2 and 4-[4-(diethylamino)butoxy]benzylamine obtained in Reference Example 86.

$^1$H-NMR (DMSO-d$_6$) δ(ppm): 1.15–1.29(9H, m), 1.65–1.82(4H, m), 2.90–3.10(6H, m), 3.37(2H, q, J=6.9 Hz), 3.92–4.01(2H, m), 4.67(2H, d, J=5.6 Hz), 6.85(1H, s), 6.90 (2H, d, J=8.6 Hz), 7.30(2H, d, J=8.6 Hz), 7.75 (1H, br), 8.33(1H, s), 9.25(1H, br), 9.29(1H, s).

REFERENCE EXAMPLE 88

4-{2-[(Dimethylamino)methyl]benzylamino}-7-ethylamino-6-nitroquinazoline

The title compound was obtained from 7-ethylamino-4-[2-(hydroxymethyl)benzylamino]-6-nitroquinazoline obtained in Reference Example 4 and an about 50% aqueous solution of dimethylamine.

$^1$H-NMR (CDCl$_3$) δ(ppm): 1.39(3H, t, J=7.3 Hz), 2.46 (6H, s), 3.37(2H, q, J=7.3 Hz), 3.59(2H, s), 4.86(2H, d, J=5.0 Hz), 6.93(1H, s), 7.26–7.34(3H, m), 7.46–7.49 (1H, m), 7.69(1H, br), 8.52(1H, s), 8.63(1H, s), 10.31 (1H, br).

EXAMPLE 1

3-Ethyl-8-[2-(morpholinomethyl)benzylamino]-2,3-dihydro-1H-imidazo[4,5-g]quinazolin-2-one.2 hydrochloride (Compound 1)

7-Ethylamino-4-[2-(morpholinomethyl)benzylamino]-6-nitroquinazoline (1.30 g, 3.07 mmol) obtained in Reference Example 9 was dissolved in tetrahydrofuran (50 ml), and reduced at room temperature in a hydrogen atmosphere by adding 10% palladium on carbon (270 mg). After the reaction, the catalyst was filtered off and the filtrate was concentrated. A half of the obtained oily substances was dissolved in acetonitrile (30 ml), and N,N'-carbonyldiimidazole (1.50 g, 9.3 mmol) was added thereto, followed by stirring at 80° C. for 2 hours. After the reaction, the solution was concentrated under reduced pressure, and the residue was purified by silica gel column chromatography (eluent: chloroform/methanol=100). The obtained free base (0.50 g) was suspended in methanol (25 ml) under ice-cooling, and a saturated solution of hydrogen chloride in ethyl acetate (25 ml) was added thereto. The solution was further stirred and the precipitated crystals were collected by filtration followed by drying to give the title compound (0.44 g, 58%).

$^1$H-NMR (DMSO-$d_6$) δ(ppm): 1.28(3H, t, J=7.2 Hz), 3.25–3.40 (4H, m), 3.85–4.00(6H, m), 4.61(2H, s), 5.13(2H, d, J=5.4 Hz), 7.35–7.40(2H, m), 7.46(1H, s), 7.47–7.55(2H, m), 7.65–7.72(1H, m), 8.21(1H, s), 8.83 (1H, s), 10.58(1H, br), 11.97(1H, s).

The following compounds of Examples 2, 3, 21 to 28, 53, 55, 56, 59 to 61, 70, 76 to 78, 81, and 85 to 88 were prepared according to a manner similar to that in Example 1.

EXAMPLE 2

3-Ethyl-8-[3-(morpholinomethyl)benzylamino]-2,3-dihydro-1H-imidazo[4,5-g]quinazolin-2-one.2 hydrochloride (Compound 2)

This compound was synthesized from the compound obtained in Reference Example 10.

$^1$H-NMR (DMSO-$d_6$) δ(ppm): 1.28(3H, t, J=7.2 Hz), 2.95–3.20 (4H, m), 3.75–4.00(6H, m), 4.29(2H, s), 4.96(2H, d, J=5.4 Hz), 7.40–7.55(4H, m), 7.63(1H, s), 8.17 (1H, s), 8.80(1H, s), 10.49–10.52(1H, m), 11.99 (1H, s).

EXAMPLE 3

3-Ethyl-8-[4-(piperidinomethyl)benzylamino]-2,3-dihydro-1H-imidazo[4,5-g]quinazolin-2-one.2 hydrochloride (Compound 3)

This compound was synthesized from the compound obtained in Reference Example 11.

$^1$H-NMR (DMSO-$d_6$) δ(ppm): 1.27(3H, t, J=7.2 Hz), 1.60–1.80(6H, m), 2.72–2.90(2H, m), 3.15–3.40(2H, m), 3.95 (2H, q, J=7.2 Hz), 4.24 (2H, s), 4.96(2H, d, J=5.4 Hz), 7.47(2H, d, J=8.4 Hz), 7.49(1H, s), 7.59 (2H, d, J=8.4 Hz), 8.19(1H, s), 8.81(1H, s), 10.58–10.60(2H, m), 12.00(1H, s).

EXAMPLE 4

3-Ethyl-8-[2-(morpholinomethyl)benzylamino]-2,3-dihydro-1H-imidazo[4,5-g]quinazoline-2-thione.2 hydrochloride (Compound 4)

7-Ethylamino-4-[2-(morpholinomethyl)benzylamino]-6-nitroquinazoline (1.3 g, 3.1 mmol) obtained in Reference Example 9 was dissolved in tetrahydrofuran (50 ml), and reduced at room temperature in a hydrogen atmosphere by adding 10% palladium on carbon (270 mg). After the reaction, the catalyst was filtered off and the filtrate was concentrated. A half of the obtained oily substances was dissolved in ethanol (20 ml), and triethylamine (0.5 ml, 3.6 mmol) and carbon disulfide (5 ml, 83.1 mmol) were added thereto, followed by stirring at room temperature for one night. After the reaction, precipitated crystals were collected by filtration and washed with ethanol. The obtained free base was suspended in methanol under ice-cooling, and a saturated solution of hydrogen chloride in ethyl acetate was added thereto. The solution was concentrated, and the residue was dissolved in ethanol, followed by addition of ether. The precipitated crystals were collected by filtration and dried to give the title compound (0.50 g, 64%).

$^1$H-NMR (DMSO-$d_6$) δ(ppm): 1.30(3H, t, J=7.2 Hz), 3.25–3.50 (4H, m), 3.85–4.05(4H, m), 4.34(2H, q, J=7.2 Hz), 4.62(2H, s), 5.16(2H, d, J=5.4 Hz), 7.36–7.50(2H, m), 7.50–7.56(1H, m), 7.78–7.82(2H, m), 8.49(1H, s), 8.88(1H, s), 10.95(1H, br), 11.48(1H, br), 13.76(1H, s).

The following compounds of Examples 5 to 20, 29 to 52, 54, 57, 58, 62 to 69, 72 to 75, 79, 80, 82 to 84, and 89 were prepared according to a manner similar to that in Example 4.

EXAMPLE 5

3-Ethyl-8-[2-(piperidinomethyl)benzylamino]-2,3-dihydro-1H-imidazo[4,5-g]quinazoline-2-thione.2 hydrochloride (Compound 5)

This compound was synthesized from the compound obtained in Reference Example 12.

$^1$H-NMR (DMSO-$d_6$) δ(ppm): 1.30(3H, t, J=6.9 Hz), 1.75–2.00 (6H, m), 3.00–3.20(2H, m), 3.30–3.50(2H, m), 4.35 (2H, q, J=6.9 Hz), 4.54(2H, s), 5.12(2H, d, J=4.9 Hz), 7.36–7.44(2H, m), 7.44–7.54(1H, m), 7.60–7.70(2H, m), 8.44(1H, s), 8.88(1H, s), 10.81 (1H, br), 13.75(1H, s).

EXAMPLE 6

8-[2-(Diethylaminomethyl)benzylamino]-3-ethyl-2,3-dihydro-1H-imidazo[4,5-g]quinazoline-2-thione.2 hydrochloride (Compound 6)

This compound was synthesized from the compound obtained in Reference Example 13.

$^1$H-NMR (DMSO-$d_6$) δ(ppm): 1.25–1.40(9H, m), 3.20–3.30(4H, m), 4.36(2H, q, J=6.9 Hz), 4.58(2H, s), 5.10(2H, d, J=5.6 Hz), 7.36–7.43(2H, m), 7.52–7.57(1H, m), 7.71–7.75(2H, m), 8.45(1H, s), 8.88(1H, s), 10.51 (1H, br), 10.86(1H, br), 13.73(1H, s).

EXAMPLE 7

3-Ethyl-8-[2-(4-methylpiperazin-1-ylmethyl)benzylamino]-2,3-dihydro-1H-imidazo[4,5-g]quinazoline-2-thione.3 hydrochloride (Compound 7)

This compound was synthesized from the compound obtained in Reference Example 14.

$^1$H-NMR (DMSO-$d_6$) δ(ppm): 1.31(3H, t, J=6.9 Hz), 2.83(3H, s), 3.20–3.60(10H, m), 4.36(2H, q, J=6.9 Hz), 5.14 (2H, d, J=5.4 Hz), 7.35–7.40(2H, m), 7.42–7.50(1H, m), 7.53–7.65(1H, m), 7.72(1H, s), 8.44(1H, s), 8.92(1H, s), 10.72(1H, br), 13.73(1H, s).

EXAMPLE 8

8-[2-(4-Benzylpiperazin-1-ylmethyl)benzylamino]-3-ethyl-2,3-dihydro-1H-imidazo[4,5-g]quinazoline-2-thione.3 hydrochloride (Compound 8)

This compound was synthesized from the compound obtained in Reference Example 15.

$^1$H-NMR (DMSO-$d_6$) δ(ppm): 1.30(3H, t, J=7.1 Hz), 3.40–3.80(12H, m), 4.35(2H, q, J=7.1 Hz), 5.12(2H, s), 7.30–7.51(7H, m), 7.60–7.75(2H, m), 7.75(1H, s), 8.45(1H, s), 8.93(1H, s), 10.82(1H, br), 13.76(1H, s).

EXAMPLE 9

3-Ethyl-8-{2-[4-(2-pyridyl)piperazin-1-ylmethyl]benzylamino}-2,3-dihydro-1H-imidazo[4,5-g]quinazoline-2-thione.3 hydrochloride (Compound 9)

This compound was synthesized from the compound obtained in Reference Example 16.

¹H-NMR (DMSO-d₆) δ(ppm): 1.31(3H, t, J=7.1 Hz), 3.40–4.10 (8H, m), 4.35(2H, q, J=7.1 Hz), 4.66(2H, s), 5.17(2H, d, J=5.3 Hz), 6.93(1H, dd, J=6.3 Hz, 6.3 Hz), 7.26(1H, d, J=8.9 Hz), 7.40–7.50(2H, m), 7.51–7.55 (1H, m), 7.80–7.90(2H, m), 8.13(1H, d, J=4.3 Hz), 8.46(1H, s), 8.93(1H, s), 10.90(1H, br), 13.76(1H, s).

EXAMPLE 10

3-Ethyl-8-{2-{[(2-pyridyl)methyl]aminomethyl}benzylamino}-2,3-dihydro-1H-imidazo[4,5-g]quinazoline-2-thione.3 hydrochloride (Compound 10)

This compound was synthesized from the compound obtained in Reference Example 17.

¹H-NMR (DMSO-d₆) δ(ppm): 1.30(3H, t, J=7.3 Hz), 4.35(2H, q, J=7.3 Hz), 4.50(4H, s), 5.07(2H, d, J=5.0 Hz), 7.39–7.69(6H, m), 7.76(1H, s), 7.92(1H, t, J=7.6 Hz), 8.45 (1H, s), 8.64(1H, d, J=4.0 Hz), 8.87 (1H, s), 10.79(1H, br), 13.78(1H, s).

EXAMPLE 11

3-Ethyl-8-[2-(1-morpholinoethyl)benzylamino]-2,3-dihydro-1H-imidazo[4,5-g]quinazoline-2-thione.2 hydrochloride (Compound 11)

This compound was synthesized from the compound obtained in Reference Example 18.

¹H-NMR (DMSO-d₆) δ(ppm): 1.31(3H, t, J=7.1 Hz), 1.70(3H, d, J=6.3 Hz), 3.41–3.46(4H, m), 3.80–4.10(4H, m), 4.35(2H, q, J=7.1 Hz), 4.90–5.15(3H, m), 7.35–7.44 (2H, m), 7.55(1H, dd, J=1.6 Hz, 7.2 Hz), 8.21(1H, d, J=7.2 Hz), 8.52(1H, s), 8.87(1H, s), 10.98(1H, br), 11.74(1H, br), 13.76(1H, s).

EXAMPLE 12

3Ethyl-8-{2-[1-(4-methylpiperazin-1-yl)ethyl]benzylamino}-2,3-dihydro-1H-imidazo[4,5-g]quinazoline-2-thione.3 hydrochloride (Compound 13)

This compound was synthesized from the compound obtained in Reference Example 19.

¹H-NMR (DMSO-d₆) δ(ppm): 1.30(3H, t, J=7.2 Hz), 1.63(3H, d, J=4.9 Hz), 2.84(3H, s), 3.20–3.60(8H, m), 4.35 (2H, q, J=7.2 Hz), 4.90–5.00(1H, br), 5.04(2H, d, J=4.5 Hz), 7.35–7.45(2H, m), 7.53–7.56(1H, m), 7.73 (1H, s), 8.02(1H, br), 8.49(1H, s), 8.97(1H, s), 10.90(1H, br), 13.75(1H, s).

EXAMPLE 13

3-Ethyl-8-[3-(morpholinomethyl)benzylamino]-2,3-dihydro-1H-imidazo[4,5-g]quinazoline-2-thione.2 hydrochloride (Compound 13)

This compound was synthesized from the compound obtained in Reference Example 10.

¹H-NMR (DMSO-d₆) δ(ppm): 1.32(3H, t, J=6.9 Hz), 3.00–3.30(4H, m), 3.75–3.95(4H, m), 4.29(2H, s), 4.36(2H, q, J=6.9 Hz), 4.98(2H, d, J=5.3 Hz), 7.40–7.58(3H, m), 7.69(1H, s), 7.76(1H, s), 8.42(1H, s), 8.85 (1H, s), 10.78(1H, s), 11.68(1H, br), 13.74(1H, s).

EXAMPLE 14

3-Ethyl-8-[4-(morpholinomethyl)benzylamino]-2,3-dihydro-1H-imidazo[4,5-g]quinazoline-2-thione.2 hydrochloride (Compound 14)

This compound was synthesized from the compound obtained in Reference Example 20.

¹H-NMR (DMSO-d₆) δ(ppm): 1.30(3H, t, J=7.2 Hz), 3.00–3.25 (2H, m), 3.30–3.50(4H, m), 3.70–4.00(3H, m), 4.25–4.40(3H, m), 4.97(2H, d, J=5.9 Hz), 7.49(2H, d, J=8.4 Hz), 7.60(2H, d, J=8.4 Hz), 7.70(1H, s), 8.37 (1H, s), 8.86(1H, s), 10.71(1H, br), 13.77(1H, s).

EXAMPLE 15

3-Ethyl-8-[4-(piperidinomethyl)benzylamino]-2,3-dihydro-1H-imidazo[4,5-g]quinazoline-2-thione.2 hydrochloride (Compound 15)

This compound was synthesized from the compound obtained in Reference Example 11.

¹H-NMR (DMSO-d₆) δ(ppm): 1.31(3H, t, J=7.2 Hz), 1.66–1.80 (4H, m), 2.70–2.90(2H, m), 3.15–3.40(4H, m), 4.23 (2H, s), 4.36(2H, q, J=7.2 Hz), 4.98(2H, d, J=5.4 Hz), 7.48(2H, d, J=8.4 Hz), 7.60(2H, d, J=8.4 Hz), 7.72(1H, s), 8.39(1H, s), 8.86(1H, s), 10.65–10.74(2H, m), 13.75(1H, s).

EXAMPLE 16

3-Ethyl-8-[4-(4-methylpiperazin-1-ylmethyl)benzylamino]-2,3-dihydro-1H-imidazo[4,5-g]quinazoline-2-thione.3 hydrochloride (Compound 16)

This compound was synthesized from the compound obtained in Reference Example 21.

¹H-NMR (DMSO-d₆) δ(ppm): 1.31(3H, t, J=6.9 Hz), 2.79(3H, s), 3.30–3.70(10H, m), 4.36(2H, q, J=6.9 Hz), 4.98 (2H, d, J=5.9 Hz), 7.45–7.60(4H, m), 7.70 (1H, s), 8.38(1H, s), 8.87(1H, s), 10.70–10.80(1H, m), 13.75(1H, s).

EXAMPLE 17

8-{4-[(1-Butylamino)methyl]benzylamino}-3-ethyl-2,3-dihydro-1H-imidazo[4,5-g]quinazoline-2-thione.2 hydrochloride (Compound 17)

This compound was synthesized from the compound obtained in Reference Example 22.

¹H-NMR (DMSO-d₆) δ(ppm): 0.87(3H, t, J=7.3 Hz), 1.17–1.35 (5H, m), 1.60–1.75(2H, m), 2.84(2H, br), 4.09 (2H, br), 4.35(2H, q, J=7.3 Hz), 4.96(2H, d, J=5.6 Hz), 7.45(2H, d, J=8.3 Hz), 7.54(2H, d, J=8.3 Hz), 7.73 (1H, s), 8.40(1H, s), 8.84(1H, s), 9.26(2H, br), 10.76(1H, br), 13.76 (1H, s).

EXAMPLE 18

3-Ethyl-8-{4-[(1-propylamino)methyl]benzylamino}-2,3-dihydro-1H-imidazo[4,5-g]quinazoline-2-thione.2 hydrochloride(Compound 18)

This compound was synthesized from the compound obtained in Reference Example 23.

¹H-NMR (DMSO-d₆) δ(ppm): 0.88(3H, t, J=7.4 Hz), 1.30(3H, t, J=6.9 Hz), 1.61–1.71(2H, m), 2.80(2H, br), 4.09 (2H, s), 4.35(2H, q, J=6.9 Hz), 4.96(2H, d, J=5.6 Hz), 7.45(2H, d, J=8.3 Hz), 7.54(2H, d, J=8.3 Hz), 7.73(1H, s), 8.40(1H, s), 8.83(1H, s), 9.27(2H, m), 10.73(1H, br), 13.76 (1H, s).

EXAMPLE 19

3-Ethyl-8-{4-{[(2-pyridyl)methyl]aminomethyl}benzylamino}-2,3-dihydro-1H-imidazo[4,5-g]quinazoline-2-thione.3 hydrochloride (Compound 19)

This compound was synthesized from the compound obtained in Reference Example 24.

¹H-NMR (DMSO-d₆) δ(ppm): 1.30(3H, t, J=7.3 Hz), 4.21(2H, s), 4.29(2H, s), 4.35(2H, q, J=7.3 Hz), 4.97(2H, d, J=5.6 Hz), 7.34–7.63(6H, m), 7.78(1H, s), 7.93(1H, dd, J=7.6 Hz, 7.6 Hz), 8.45(1H, s), 8.65(1H, d, J=5.0 Hz), 8.92(1H, s), 10.91(1H, br), 13.79(1H, s).

EXAMPLE 20

3-Ethyl-8-[4-[(1-pyrrolidinyl)methyl]benzylamino]-2,3-dihydro-1H-imidazo[4,5-g]quinazoline-2-thione.2 hydrochloride This compound was synthesized from the compound obtained in Reference Example 25.

¹H-NMR (DMSO-d₆) δ(ppm): 1.30(3H, t, J=7.1 Hz), 1.80–2.01 (4H, m), 2.99–3.35(4H, m), 4.30–4.37(4H, m), 4.98 (2H, d, J=5.6 Hz), 7.47(2H, d, J=7.9 Hz), 7.58(2H, d, J=7.9 Hz), 7.70(1H, s), 8.37(1H, s), 8.86(1H, s), 10.71(1H, br), 13.76(1H, s).

EXAMPLE 21

3-Ethyl-8-[2-(2-morpholinoethoxy)benzylamino]-2,3-dihydro-1H-imidazo[4,5-g]quinazolin-2-one.2 hydrochloride (Compound 21)

This compound was synthesized from the compound obtained in Reference Example 28.

¹H-NMR (DMSO-d₆) δ(ppm): 1.31(3H, t, J=6.8 Hz), 3.20–3.45 (4H, m), 3.55–3.65(2H, m), 3.85–4.05(6H, m), 4.51 (2H, br), 4.93(2H, br), 6.90–7.07(2H, m), 7.26–7.35 (2H, m), 7.46(1H, s), 8.29(1H, s), 8.79(1H, s), 10.42(1H, s), 11.95(1H, s).

EXAMPLE 22

3-Ethyl-8-[2-(2-piperidinoethoxy)benzylamino]-2,3-dihydro-1H-imidazo[4,5-g]quinazolin-2-one.2 hydrochloride (Compound 22)

This compound was synthesized from the compound obtained in Reference Example 29.

¹H-NMR (DMSO-d₆) δ(ppm): 1.28(3H, t, J=6.9 Hz), 1.28–1.50 (2H, m), 1.65–1.95(4H, m), 2.95–3.10(2H, m), 3.50–3.60(4H, m), 3.95(2H, q, J=6.9 Hz), 4.42–4.51(2H, m), 4.90(2H, br), 6.90–6.97(1H, m), 6.98–7.05(1H, m), 7.27–7.33(2H, m), 7.50(1H, s), 8.30(1H, s), 8.80(1H, s), 10.48(1H, s), 10.83 (1H, br), 12.00 (1H, s).

EXAMPLE 23

8-{2-[2-(Diethylamino)ethoxy]benzylamino}-3-ethyl-2,3-dihydro-1H-imidazo[4,5-g]quinazolin-2-one.2 hydrochloride (Compound 23)

This compound was synthesized from the compound obtained in Reference Example 30.

¹H-NMR (DMSO-d₆) δ(ppm): 1.18–1.35(9H, m), 3.15–3.45(4H, m), 3.50–3.60(2H, m), 3.85–4.00(2H, m), 4.40–4.50 (2H, m), 4.92(2H, d, J=4.5 Hz), 6.91–6.97(1H, m), 7.08(1H, d, J=7.9 Hz), 7.27–7.33(2H, m), 7.53(1H, s), 8.32(1H, s), 8.80(1H, s), 10.51(1H, br), 10.80 (1H, br), 12.00(1H, s).

EXAMPLE 24

3-Ethyl-8-{2-[2-(4-methylpiperazin-1-yl)ethoxy]benzylamino}-2,3-dihydro-1H-imidazo[4,5-g]quinazolin-2-one.3 hydrochloride (Compound 24)

This compound was synthesized from the compound obtained in Reference Example 31.

¹H-NMR (DMSO-d₆) δ(ppm): 1.29(3H, t, J=7.2 Hz), 2.86(3H, s), 3.30–4.00(12H, m), 4.49(2H, s), 4.95(2H, d, J=5.4 Hz), 6.94(1H, dd, J=7.4 Hz, 7.4 Hz), 7.05(1H, d, J=8.4 Hz), 7.50(1H, s), 8.28(1H, s), 8.20–8.35 (1H, br), 8.85(1H, s), 10.40(1H, br), 11.98(1H, s).

EXAMPLE 25

8-{3-[3-(Dimethylamino)propoxy]benzylamino}-3-ethyl-2,3-dihydro-1H-imidazo[4,5-g]quinazolin-2-one.2 hydrochloride (Compound 25)

This compound was synthesized from the compound obtained in Reference Example 33.

¹H-NMR (DMSO-d₆) δ(ppm): 1.27(3H, t, J=7.1 Hz), 2.08–2.17 (2H, m), 2.74(3H, s), 2.75(3H, s), 3.13–3.21(2H, m), 3.94(2H, q, J=7.1 Hz), 4.04(2H, t, J=5.9 Hz), 4.89(2H, d, J=5.6 Hz), 6.84(1H, d, J=7.3 Hz), 6.97–7.00(2H, m), 7.26(1H, dd, J=7.9 Hz, 8.3 Hz), 7.55 (1H, s), 8.26(1H, s), 8.80(1H, s), 10.65–10.68(1H, m), 10.88(1H, br), 12.03(1H, s).

EXAMPLE 26

8-{4-[3-(Dimethylamino)propoxy]benzylamino}-3-ethyl-2,3-dihydro-1H-imidazo[4,5-g]quinazolin-2-one.2 hydrochloride (Compound 26)

This compound was synthesized from the compound obtained in Reference Example 34.

¹H-NMR (DMSO-d₆) δ(ppm): 1.24(3H, t, J=7.4 Hz), 2.09–2.20 (2H, m), 2.75(3H, s), 2.76(3H, s), 3.12–3.25(2H, m), 3.93(2H, q, J=7.4 Hz), 4.04(2H, t, J=6.2 Hz), 4.85(2H, d, J=5.4 Hz), 6.91(2H, d, J=8.4 Hz), 7.35 (2H, d, J=8.4 Hz), 7.54(1H, s), 8.21(1H, s), 8.79(1H, s), 10.58–10.63(1H, m), 10.89(1H, br), 12.01 (1H, s).

EXAMPLE 27

3-Ethyl-8-[2-(4-morpholinobutoxy)benzylamino]-2,3-dihydro-1H-imidazo[4,5-g]quinazolin-2-one.2 hydrochloride (Compound 27)

This compound was synthesized from the compound obtained in Reference Example 38.

¹H-NMR (DMSO-d₆) δ(ppm): 1.29(3H, t, J=7.2 Hz), 1.77–1.94 (4H, m), 2.95–3.20(6H, m), 3.80–4.00(6H, m), 4.07 (2H, t, J=5.7 Hz), 4.93(2H, d, J=5.4 Hz), 6.89(1H, dd, J=7.4 Hz, 7.4 Hz), 7.02(1H, d, J=8.4 Hz), 7.19 (1H, d, J=7.4 Hz), 7.27(1H, dd, J=7.4 Hz, 8.4 Hz), 7.49(1H, s), 8.21(1H, s), 8.82(1H, s), 10.28(1H, br), 11.14(1H, br), 11.98(1H, s).

EXAMPLE 28

3-Ethyl-8-[2-(4-piperidinobutoxy)benzylamino]-2,3-dihydro-1H-imidazo[4,5-g]quinazolin-2-one.2 hydrochloride (Compound 28)

This compound was synthesized from the compound obtained in Reference Example 39.

¹H-NMR (DMSO-d₆) δ(ppm): 1.28(3H, t, J=7.2 Hz), 1.70–2.00 (10H, m), 2.75–2.90(2H, m), 2.95–3.10(2H, m), 3.30–3.40(2H, m), 3.95(2H, q, J=7.2 Hz), 4.07(2H, t, J=5.7 Hz), 4.93(2H, d, J=5.4 Hz), 6.89(1H, dd, J=7.4 Hz, 7.4 Hz), 7.02(1H, d, J=8.4 Hz), 7.19(1H, d, J=7.4 Hz), 7.27(1H, dd, J=7.4 Hz, 8.4 Hz), 8.23(1H, s), 8.82(1H, s), 10.30–10.50 (2H, m), 12.00(1H, s), 14.85(1H, s).

EXAMPLE 29

3-Ethyl-8-[2-(2-morpholinoethoxy)benzylamino]-2,3-dihydro-1H-imidazo[4,5-g]quinazoline-2-thione.2 hydrochloride This compound was synthesized from the compound obtained in Reference Example 28.

¹H-NMR (DMSO-d₆) δ(ppm): 1.32(3H, t, J=6.9 Hz), 3.45–3.70 (6H, m), 3.85–4.00(4H, m), 4.25–4.55(4H, m), 4.94 (2H, br), 6.85–7.10(2H, m), 7.15–7.40 (2H, m), 7.70 (1H, s), 8.48(1H, s), 8.85(1H, s), 10.61(1H, s), 1.50–11.80 (1H, br), 13.74(1H, s).

EXAMPLE 30

3-Ethyl-8-[2-(2-piperidinoethoxy)benzylamino]-2,3-dihydro-1H-imidazo[4,5-g]quinazoline-2-thione.2 hydrochloride (Compound 30)

This compound was synthesized from the compound obtained in Reference Example 29.

¹H-NMR (DMSO-d₆) δ(ppm): 1.31(3H, t, J=7.1 Hz), 1.60–2.05 (6H, m), 2.92–3.12(2H, m), 3.30–3.60(4H, m), 4.35(2H, q, J=7.1 Hz), 4.45–4.57(2H, m), 4.93(2H, d, J=4.6 Hz), 6.89–7.00(1H, m), 7.07(1H, d, J=7.9 Hz), 7.20–7.35 (2H, m), 7.78(1H, s), 8.52(1H, s), 8.86 (1H, s), 10.74(1H, br), 11.03(1H, br), 13.78(1H, s).

EXAMPLE 31

8-{2-[2-(Diethylamino)ethoxy]benzylamino}-3-ethyl-2,3-dihydro-1H-imidazo[4,5-g]quinazoline-2-thione.2 hydrochloride (Compound 31)

This compound was synthesized from the compound obtained in Reference Example 30.

¹H-NMR (DMSO-d₆) δ(ppm): 1.26–1.33(9H, m), 3.20–3.40(4H, m), 3.50–3.60(2H, m), 4.36(2H, q, J=5.9 Hz), 4.45–4.50(2H, m), 4.94(2H, d, J=5.4 Hz), 6.92–6.98(1H, m), 7.09(1H, d, J=7.9 Hz), 7.29–7.34(2H, m), 7.74 (1H, s), 8.50(1H, s), 8.85(1H, s), 10.68(1H, br), 10.81(1H, br), 13.76(1H, s).

EXAMPLE 32

3-Ethyl-8-{2-[2-(4-methylpiperazin-1-yl)ethoxy]benzylamino}-2,3-dihydro-1H-imidazo[4,5-g]quinazoline-2-thione.3 hydrochloride (Compound 32)

This compound was synthesized from the compound obtained in Reference Example 31.

¹H-NMR (DMSO-d₆) δ(ppm): 1.31(3H, t, J=7.2 Hz), 2.85(3H, s), 3.40–4.00(10H, m), 4.36(2H, q, J=7.2 Hz), 4.50 (2H, s), 4.97(2H, d, J=4.5 Hz), 6.96(1H, dd, J=7.4 Hz, 7.9 Hz), 7.07(1H, d, J=7.9 Hz), 7.27–7.34 (2H, m), 7.74(1H, s), 8.49(1H, s), 8.92(1H, s), 10.62(1H, br), 13.75(1H, s).

EXAMPLE 33

8-{2-[3-(Dimethylamino)propoxy]benzylamino}-3-ethyl-2,3-dihydro-1H-imidazo[4,5-g]quinazoline-2-thione.2 hydrochloride (Compound 33)

This compound was synthesized from the compound obtained in Reference Example 35.

¹H-NMR (DMSO-d₆) δ(ppm): 1.31(3H, t, J=7.1 Hz), 2.15–2.24 (2H, m), 2.75(3H, s), 2.77(3H, s), 3.20–3.35(2H, m), 4.13(2H, t, J=5.9 Hz), 4.35(2H, q, J=7.1 Hz), 4.92(2H, d, J=5.3 Hz), 6.91(1H, dd, J=7.3 Hz, 7.6 Hz), 7.04(1H, d, J=7.9 Hz), 7.23–7.30(2H, m), 7.75(1H, s), 8.47(1H, s), 8.87(1H, s), 10.58(1H, br), 10.77(1H, br), 13.76(1H, s).

EXAMPLE 34

3-Ethyl-8-[2-(3-morpholinopropoxy)benzylamino]-2,3-dihydro-1H-imidazo[4,5-g]quinazoline-2-thione.2 hydrochloride (Compound 34)

This compound was synthesized from the compound obtained in Reference Example 37.

¹H-NMR (DMSO-d₆) δ(ppm): 1.31(3H, t, J=7.2 Hz), 2.20–2.30 (2H, m), 2.95–3.20(2H, m), 3.30–3.50(4H, m), 3.80–4.00(4H, m), 4.14(2H, t, J=5.9 Hz), 4.35(2H, q, J=7.2 Hz), 4.93(2H, d, J=5.0 Hz), 6.91(1H, dd, J=7.4 Hz, 7.4 Hz), 7.05(1H, d, J=7.9 Hz), 7.22–7.31 (2H, m), 7.75(1H, s), 8.47(1H, s), 8.86(1H, s), 10.57(1H, br), 11.43(1H, br), 13.76(1H, s).

EXAMPLE 35

3-Ethyl-8-{2-[1-(morpholinomethyl)ethoxy]benzylamino}-2,3-dihydro-1H-imidazo[4,5-g]quinazoline-2-thione.2 hydrochloride (Compound 35)

This compound was synthesized from the compound obtained in Reference Example 42.

¹H-NMR (DMSO-d₆) δ(ppm): 1.21(3H, d, J=5.9 Hz), 1.30(3H, t, J=6.9 Hz), 3.39–3.60(6H, m), 3.85–4.00(4H, m), 4.34(2H, q, J=6.9 Hz), 4.80–5.00(2H, m), 5.31–5.33 (1H, m), 6.95(1H, dd, J=7.4 Hz, 7.4 Hz), 7.21(1H, d, J=7.9 Hz), 7.25–7.36(2H, m), 7.78(1H, s), 8.52(1H, s), 8.85(1H, s), 10.67(1H, s), 11.60(1H, br), 3.77 (1H, s).

EXAMPLE 36

3-Ethyl-8-[2-(4-morpholinobutoxy)benzylamino]-2,3-dihydro-1H-imidazo[4,5-g]quinazoline-2-thione.2 hydrochloride (Compound 36)

This compound was synthesized from the compound obtained in Reference Example 38.

¹H-NMR (DMSO-d₆) δ(ppm): 1.31(3H, t, J=7.2 Hz), 1.72–1.92(4H, m), 2.95–3.20(6H, m), 3.80–4.00(4H, m), 4.07 (2H, t, J=5.9 Hz), 4.36(2H, q, J=7.2 Hz), 4.94(2H, d, J=5.4 Hz), 6.90(1H, dd, J=7.4 Hz, 7.9 Hz), 7.04 (1H, d, J=7.9 Hz), 7.21(1H, d, J=6.9 Hz), 7.28(1H, dd, J=6.9 Hz, 7.4 Hz), 7.75(1H, s), 8.44(1H, s), 8.87(1H, s), 10.51(1H, br), 11.24(1H, br), 13.76 (1H, s).

EXAMPLE 37

3-Ethyl-8-[2-(4-piperidinobutoxy)benzylamino]-2,3-dihydro-1H-imidazo[4,5-g]quinazoline-2-thione.2 hydrochloride (Compound 37)

This compound was synthesized from the compound obtained in Reference Example 39.

¹H-NMR (DMSO-d₆) δ(ppm): 1.31(3H, t, J=7.2 Hz), 1.65–1.95(10H, m), 2.75–2.90(2H, m), 2.95–3.10(2H, m), 3.30–3.45(2H, m), 4.06(2H, t, J=5.7 Hz), 4.36(2H, q, J=7.2 Hz), 4.94(2H, d, J=5.4 Hz), 6.89(1H, dd, J=7.4 Hz, 7.9 Hz), 7.03(1H, d, J=7.9 Hz), 7.20–7.30(2H, m), 7.76(1H, s), 8.46(1H, s), 8.88(1H, s), 10.44–10.54(2H, m), 13.76(1H, s).

EXAMPLE 38

3-Ethyl-8-[3-(2-morpholinoethoxy)benzylamino]-2,3-dihydro-1H-imidazo [4,5-g]quinazoline-2-thione (Compound 38)

This compound was synthesized from the compound obtained in Reference Example 44.

¹H-NMR (DMSO-d₆) δ(ppm): 1.29(3H, t, J=6.9 Hz), 2.40–2.43(4H, m), 2.63(2H, t, J=5.7 Hz), 3.51–3.55(4H, m), 4.03(2H, t, J=5.7 Hz), 4.35(2H, q, J=6.9 Hz), 4.75(2H, d, J=5.4 Hz), 6.81(1H, d, J=7.9 Hz), 6.91–6.94(2H, m), 7.21 (1H, dd, J=7.9 Hz, 8.4 Hz), 7.64(1H, s), 8.08(1H, s), 8.38(1H, s), 8.79–8.83(1H, m), 13.25 (1H, s).

EXAMPLE 39

3-Ethyl-8-[3-(2-piperidinoethoxy)benzylamino]-2,3-dihydro-1H-imidazo[4,5-g]quinazoline-2-thione (Compound 39)

This compound was synthesized from the compound obtained in Reference Example 45.

$^1$H-NMR (DMSO-d$_6$) δ(ppm): 1.29(3H, t, J=7.2 Hz), 1.30–1.40(2H, m), 1.40–1.50(4H, m), 2.33–2.38(4H, m), 2.58 (2H, t, J=5.9 Hz), 4.00(2H, t, J=5.9 Hz), 4.35(2H, q, J=7.2 Hz), 4.75(2H, d, J=5.4 Hz), 6.80(1H, dd, J=2.0 Hz, 7.9 Hz), 6.90(1H, s), 6.92(1H, dd, J=2.0 Hz, 7.9 Hz), 7.21(1H, dd, J=7.9 Hz, 7.9 Hz), 7.63(1H, s), 8.08(1H, s), 8.38(1H, s), 8.78–8.83(1H, m).

EXAMPLE 40

8-{3-[2-(Diethylamino)ethoxy]benzylamino}-3-ethyl-2,3-dihydro-1H-imidazo[4,5-g]quinazoline-2-thione (Compound 40)

This compound was synthesized from the compound obtained in Reference Example 46.

$^1$H-NMR (DMSO-d$_6$) δ(ppm): 0.93(6H, t, J=6.9 Hz), 1.28(3H, t, J=7.2 Hz), 2.50(4H, q, J=6.9 Hz), 2.71(2H, t, J=6.2 Hz), 3.96(2H, t, J=6.2 Hz), 4.33(2H, q, J=7.2 Hz), 4.75(2H, d, J=5.9 Hz), 6.78(1H, d, J=7.9 Hz), 6.91–6.93(2H, m), 7.20(1H, dd, J=7.9 Hz, 8.4 Hz), 7.49(1H, s), 8.03(1H, s), 8.34(1H, s), 8.65–8.70(1H, m).

EXAMPLE 41

8-{3-[3-(Dimethylamino)propoxy]benzylamino}-3-ethyl-2,3-dihydro-1H-imidazo[4,5-g]quinazoline-2-thione.2 hydrochloride (Compound 41)

This compound was synthesized from the compound obtained in Reference Example 33.

$^1$H-NMR (DMSO-d$_6$) δ(ppm): 1.31(3H, t, J=7.1 Hz), 2.12–2.19(2H, m), 2.74(3H, s), 2.76(3H, s), 3.17–3.25(2H, m), 4.04(2H, t, J=5.9 Hz), 4.34(2H, q, J=7.1 Hz), 4.92(2H, d, J=5.6 Hz), 6.87(1H, d, J=7.7 Hz), 6.90–7.01(2H, m), 7.27(1H, dd, J=7.9 Hz, 8.3 Hz), 7.79(1H, s), 8.46(1H, s), 8.85(1H, s), 10.84–10.88(2H, m), 13.77(1H, s).

EXAMPLE 42

3-Ethyl-8-[4-(2-morpholinoethoxy)benzylamino]-2,3-dihydro-1H-imidazo[4,5-g]quinazoline-2-thione.2 hydrochloride (Compound 42)

This compound was synthesized from the compound obtained in Reference Example 48.

$^1$H-NMR (DMSO-d$_6$) δ(ppm): 1.31(3H, t, J=6.9 Hz), 3.30–3.60(6H, m), 3.75–4.05(4H, m), 4.28–4.49(4H, m), 4.89(2H, d, J=4.6 Hz), 6.98(2H, d, J=8.3 Hz), 7.39(2H, d, J=8.3 Hz), 7.72(1H, s), 8.38(1H, s), 8.86(1H, s), 10.68–10.73(1H, br), 13.70(1H, br).

EXAMPLE 43

8-{4-[3-(Dimethylamino)propoxy]benzylamino}-3-ethyl-2,3-dihydro-1H-imidazo[4,5-g]quinazoline-2-thione.2 hydrochloride (Compound 43)

This compound was synthesized from the compound obtained in Reference Example 34.

$^1$H-NMR (DMSO-d$_6$) δ(ppm): 1.30(3H, t, J=7.2 Hz), 2.11–2.20(2H, m), 2.75(3H, s), 2.76(3H, s), 3.12–3.25(2H, m), 4.04(2H, t, J=5.9 Hz), 4.34(2H, q, J=7.2 Hz), 4.88(2H, d, J=5.4 Hz), 6.92(2H, d, J=8.7 Hz), 7.36(2H, d, J=8.7 Hz), 7.76(1H, s), 8.40(1H, s), 8.85(1H, s), 10.70–10.83(2H, m), 13.75(1H, s).

EXAMPLE 44

3-Ethyl-8-[2-(4-phenylpiperazin-1-ylmethyl)benzylamino]-2,3-dihydro-1H-imidazo[4,5-g]quinazoline-2-thione.3 hydrochloride (Compound 44)

This compound was synthesized from the compound obtained in Reference Example 49.

$^1$H-NMR (DMSO-d$_6$) δ(ppm): 1.32(3H, t, J=6.9 Hz), 3.34–3.62(6H, m), 3.80–3.90(2H, m), 4.36(2H, q, J=6.9 Hz), 4.67(2H, s), 5.19(2H, d, J=5.0 Hz), 6.87(1H, dd, J=6.9 Hz, 7.3 Hz), 6.95–7.03(2H, m), 7.20–7.30(2H, m), 7.40–7.45 (2H, m), 7.50–7.56(1H, m), 7.73(1H, s), 7.80–7.82(1H, m), 8.46(1H, s), 8.91(1H, s), 10.87(1H, br), 11.14(1H, br), 13.76(1H, s).

EXAMPLE 45

8-{2-[4-(2-Chlorophenyl)piperazin-1-ylmethyl]benzylamino}-3-ethyl-2,3-dihydro-1H-imidazo[4,5-g]quinazoline-2-thione.3 hydrochloride (Compound 45)

This compound was synthesized from the compound obtained in Reference Example 50.

$^1$H-NMR (DMSO-d$_6$) δ(ppm): 1.31(3H, t, J=7.1 Hz), 3.30–3.60(8H, m), 4.36(2H, q, J=7.1 Hz), 4.69(2H, s), 5.19(2H, d, J=5.0 Hz), 7.11(1H, dd, J=7.6 Hz, 7.9 Hz), 7.19(1H, d, J=7.6 Hz), 7.30–7.53(5H, m), 7.72(1H, s), 7.83(1H, br), 8.45(1H, s), 8.90(1H, s), 10.82(1H, br), 11.10 (1H, br), 13.76(1H, s).

EXAMPLE 46

3-Ethyl-8-{2-[4-(2-methoxyphenyl)piperazin-1-ylmethyl]benzylamino}-2,3-dihydro-1H-imidazo[4,5-g]quinazoline-2-thione.3 hydrochloride (Compound 46)

This compound was synthesized from the compound obtained in Reference Example 51.

$^1$H-NMR (DMSO-d$_6$) δ(ppm): 1.31(3H, t, J=7.1 Hz), 3.22–3.30(2H, m), 3.35–3.57(6H, m), 3.80(3H, s), 4.35 (2H, q, J=7.1 Hz), 4.67(2H, s), 5.20(2H, d, J=5.3 Hz), 6.88–7.05 (4H, m), 7.38–7.48(2H, m), 7.53–7.57(1H, m), 7.76(1H, s), 7.81–7.84(1H, m), 8.47(1H, s), 8.90(1H, s), 10.89(1H, br), 11.11(1H, br), 13.77(1H, s).

EXAMPLE 47

3-Ethyl-8-{2-[(1-pyrrolidinyl)methyl]benzylamino}-2,3-dihydro-1H-imidazo[4,5-g]quinazoline-2-thione.2 hydrochloride(Compound 47)

This compound was synthesized from the compound obtained in Reference Example 52.

$^1$H-NMR (DMSO-d$_6$) δ(ppm): 1.30(3H, t, J=7.1 Hz), 1.90–2.15(4H, m), 3.20–3.35(2H, m), 3.35–3.50(2H, m), 4.35(2H, q, J=7.1 Hz), 4.66(2H, s), 5.14(2H, d, J=5.3 Hz), 7.35–7.43(2H, m), 7.52–7.55(1H, m), 7.72–7.79(2H, m), 8.48(1H, s), 8.89(1H, s), 10.90(1H, br), 11.11(1H, br), 13.77(1H, s).

EXAMPLE 48

3-Ethyl-8-[2-(4-ethylpiperazin-1-ylmethyl)benzylamino]-2,3-dihydro-1H-imidazo[4,5-g]quinazoline-2-thione.3 hydrochloride (Compound 48)

This compound was synthesized from the compound obtained in Reference Example 53.

¹H-NMR (DMSO-d₆) δ(ppm): 1.25–1.35(6H, m), 3.40–3.70(12H, m), 3.45(2H, q, J=6.9 Hz), 5.15(2H, d, J=4.6 Hz), 7.35–7.45(2H, m), 7.45–7.52(1H, m), 7.60–7.70(1H, m), 7.74(1H, s), 8.44(1H, s), 8.96(1H, s), 10.78(1H, br), 13.77(1H, s).

EXAMPLE 49

8-{2-[Bis(2-hydroxyethyl)aminomethyl]benzylamino}-3-ethyl-2,3-dihydro-1H-imidazo[4,5-g]quinazoline-2-thione.2 hydrochloride (Compound 49)

This compound was synthesized from the compound obtained in Reference Example 54.

¹H-NMR (DMSO-d₆) δ(ppm): 1.31(3H, t, J=7.1 Hz), 3.37–3.50(4H, m), 3.85–3.95(4H, m), 4.36(2H, q, J=7.1 Hz), 4.78(2H, s), 5.08(2H, d, J=4.6 Hz), 7.40–7.45(2H, m), 7.50–7.53(1H, m), 7.72–7.79(2H, m), 8.43(1H, s), 8.88(1H, s), 9.84(1H, br), 10.79(1H, s), 13.76(1H, s).

EXAMPLE 50

3-Ethyl-8-[2-(4-methylhexahydro-1H-1,4-diazepin-1-ylmethyl)benzylamino]-2,3-dihydro-1H-imidazo[4,5-g]quinazoline-2-thione.3 hydrochloride (Compound 50)

This compound was synthesized from the compound obtained in Reference Example 55.

¹H-NMR (DMSO-d₆) δ(ppm): 1.31(3H, t, J=7.1 Hz), 2.26–2.41(2H, m), 2.83(3H, s), 3.47–3.66(4H, m), 3.70–4.05(4H, m), 4.36(2H, q, J=7.1 Hz), 4.68(2H, br), 5.13(2H, s), 7.36–7.44(2H, m), 7.47–7.54(1H, m), 7.73(1H, s), 7.83(1H, br), 8.46(1H, s), 8.96(1H, s), 10.86(1H, br), 11.40–11.90(1H, br).

EXAMPLE 51

3-Ethyl-8-[2-(hexahydroazepinomethyl)benzylamino]-2,3-dihydro-1H-imidazo[4,5-g]quinazoline-2-thione.2 hydrochloride (Compound 51)

This compound was synthesized from the compound obtained in Reference Example 56.

¹H-NMR (DMSO-d₆) δ(ppm): 1.30(3H, t, J=7.3 Hz), 1.60–1.80(4H, m), 1.90–1.94(4H, m), 3.20–3.30(4H, m), 4.35(2H, q, J=7.3 Hz), 4.57(2H, d, J=5.3 Hz), 5.09(2H, d, J=6.3 Hz), 7.38–7.54(2H, m), 7.77(1H, s), 7.82–7.86(1H, m), 8.47(1H, s), 8.89(1H, s), 10.78(1H, br), 10.92(1H, s), 13.79(1H, s).

EXAMPLE 52

8-{2-[(1-Butylamino)methyl]benzylamino}-3-ethyl-2,3-dihydro-1H-imidazo[4,5-g]quinazoline-2-thione.2 hydrochloride (Compound 52)

This compound was synthesized from the compound obtained in Reference Example 57.

¹H-NMR (DMSO-d₆) δ(ppm): 0.90(3H, t, J=7.3 Hz), 1.05–1.45(5H, m), 1.70–1.74(2H, m), 3.04(2H, s), 4.31–4.37 (4H, m), 5.08(2H, d, J=4.6 Hz), 7.37–7.41(2H, m), 7.42–7.52(1H, m), 7.64–7.67(1H, m), 7.74(1H, s), 8.46(1H, s), 8.88(1H, s), 9.36(2H, s), 10.74(1H, br), 13.76(1H, s).

EXAMPLE 53

3-Ethyl-8-[2-(4-methylhexahydro-1H-1,4-diazepin-1-ylmethyl)benzylamino]-2,3-dihydro-1H-imidazo[4,5-g]quinazolin-2-one (Compound 53)

This compound was synthesized from the compound obtained in Reference Example 55.

¹H-NMR (DMSO-d₆) δ(ppm): 1.31(3H, t, J=6.9 Hz), 1.75–1.90(2H, m), 2.46(3H, s), 2.72–2.85(8H, m), 3.78(2H, s), 3.98(2H, q, J=6.9 Hz), 4.97(2H, d, J=4.6 Hz), 7.22–7.27(2H, m), 7.28–7.37(2H, m), 7.40(1H, s), 7.87(1H, s), 8.37(1H, s), 8.52(1H, s).

EXAMPLE 54

8-{4-[(Diethylamino)methyl]benzylamino}-3-ethyl-2,3-dihydro-1H-imidazo[4,5-g]quinazoline-2-thione (Compound 54)

This compound was synthesized from the compound obtained in Reference Example 58.

¹H-NMR (DMSO-d₆) δ(ppm): 1.17–1.32(9H, m), 3.05–3.20(4H, m), 4.29(2H, s), 4.36(2H, q, J=6.9 Hz), 4.87(2H, d, J=5.3 Hz), 7.47(4H, br), 7.63(1H, s), 8.13(1H, s), 8.49(1H, s), 9.27(1H, br), 13.37(1H, s).

EXAMPLE 55

8-{4-[(Diethylamino)methyl]benzylamino}-3-ethyl-2,3-dihydro-1H-imidazo[4,5-g]quinazolin-2-one (Compound 55)

This compound was synthesized from the compound obtained in Reference Example 58.

¹H-NMR (DMSO-d₆) δ(ppm): 1.17–1.29(9H, m), 3.03–3.17(4H, m), 3.94(2H, q, J=7.3 Hz), 4.29(2H, s), 4.87(2H, d, J=5.0 Hz), 7.35(1H, s), 7.42–7.65(4H, m), 7.91(1H, s), 8.49(1H, s), 8.82(1H, br), 9.20(1H, t, J=5.0 Hz).

EXAMPLE 56

3-Ethyl-8-[4-(4-methylpiperazin-1-ylmethyl)benzylamino]-2,3-dihydro-1H-imidazo[4,5-g]quinazolin-2-one (Compound 56)

This compound was synthesized from the compound obtained in Reference Example 21.

¹H-NMR (DMSO-d₆) δ(ppm): 1.25(3H, t, J=7.1 Hz), 2.77(3H, br), 3.30–3.70(10H, m), 3.92(2H, q, J=7.1 Hz), 4.76(2H, d, J=5.3 Hz), 7.23(2H, d, J=7.9 Hz), 7.34(1H, s), 7.31(2H, d, J=7.9 Hz), 7.82(1H, s), 8.32(1H, s), 8.60(1H, t, J=5.3 Hz).

EXAMPLE 57

3-Ethyl-8-[2-(3-piperidinopropoxy)benzylamino]-2,3-dihydro-1H-imidazo[4,5-g]quinazoline-2-thione.2 hydrochloride (Compound 57)

This compound was synthesized from the compound obtained in Reference Example 60.

¹H-NMR (DMSO-d₆) δ(ppm): 1.32(3H, t, J=6.8 Hz), 1.65–1.85(6H, m), 2.21–2.25(2H, m), 2.75–2.85(2H, m), 3.20–3.30(4H, m), 4.13–4.19(2H, m), 4.37(2H, q, J=6.8 Hz), 4.93(2H, d, J=5.3 Hz), 6.91(1H, dd, J=6.6 Hz, 8.2 Hz), 7.03(1H, d, J=8.6 Hz), 7.20–7.31(2H, m), 7.65(1H, s), 8.27(1H, s), 8.42(1H, s), 8.86(1H, s), 10.41(1H, br).

EXAMPLE 58

8-{2-[3-(Diethylamino)propoxy]benzylamino}-3-ethyl-2,3-dihydro-1H-imidazo[4,5-g]quinazoline-2-thione.2 hydrochloride (Compound 58)

This compound was synthesized from the compound obtained in Reference Example 62.

¹H-NMR (DMSO-d₆) δ(ppm): 1.21(6H, t, J=7.3 Hz), 1.31(3H, t, J=7.1 Hz), 2.05–2.15(2H, m), 3.06–3.22(6H, m), 4.15(2H, t, J=5.8 Hz), 4.36(2H, q, J=7.1 Hz), 4.93(2H, d, J=5.3 Hz), 6.92(1H, dd, J=6.9 Hz, 7.6 Hz), 7.04(1H, d, J=7.9 Hz), 7.23–7.32(2H, m), 7.73(1H, s), 8.45(1H, s), 8.89(1H, s), 10.52(1H, br), 10.60(1H, br), 13.76(1H, s).

EXAMPLE 59

3-Ethyl-8-[2-(3-piperidinopropoxy)benzylamino]-2,3-dihydro-1H-imidazo[4,5-g]quinazolin-2-one.2 hydrochloride (Compound 59)

This compound was synthesized from the compound obtained in Reference Example 60.

$^1$H-NMR (DMSO-$d_6$) δ(ppm): 1.28(3H, t, J=7.1 Hz), 1.69–1.85(6H, m), 2.24–2.28(2H, m), 2.77–2.85(2H, m), 3.17–3.20(2H, m), 3.33–3.43(2H, m), 3.95(2H, q, J=7.1 Hz), 4.12(2H, t, J=5.6 Hz), 4.91(2H, d, J=5.0 Hz), 6.90(1H, dd, J=6.9 Hz, 7.6 Hz), 7.03(1H, d, J=8.3 Hz), 7.20–7.30(2H, m), 7.50(1H, s), 8.25(1H, s), 8.32(1H, s), 10.34(1H, br), 10.50 (1H, br), 12.00(1H, s).

EXAMPLE 60

8-{2-[3-(Dimethylamino)propoxy]benzylamino}-3-ethyl-2,3-dihydro-1H-imidazo[4,5-g]quinazolin-2-one (Compound 60)

This compound was synthesized from the compound obtained in Reference Example 35.

$^1$H-NMR (DMSO-$d_6$) δ(ppm): 1.27(3H, t, J=7.1 Hz), 2.05–2.10(2H, m), 2.52(6H, s), 2.91(2H, t, J=7.4 Hz), 3.93 (2H, q, J=7.1 Hz), 4.12(2H, t, J=6.9 Hz), 4.76(2H, d, J=5.0 Hz), 6.84(1H, dd, J=7.3 Hz, 7.6 Hz), 6.97(1H, d, J=7.9 Hz), 7.14–7.22(2H, m), 7.33(1H, s), 7.89(1H, s), 8.30(1H, s), 8.40(1H, t, J=5.0 Hz).

EXAMPLE 61

3-Ethyl-8-[2-(3-morpholinopropoxy)benzylamino]-2,3-dihydro-1H-imidazo[4,5-g]quinazolin-2-one (Compound 61)

This compound was synthesized from the compound obtained in Reference Example 37.

$^1$H-NMR (DMSO-$d_6$) δ(ppm): 1.34(3H, t, J=6.9 Hz), 1.90–2.00(2H, m), 2.27–2.38(4H, m), 2.42–2.50(2H, m), 3.57–3.62(4H, m), 3.96(2H, q, J=6.9 Hz), 4.09(2H, t, J=5.7 Hz), 4.78(2H, br), 6.88–6.93(1H, m), 6.95–7.00(1H, m), 7.10–7.21(2H, m), 7.40(1H, s), 8.23(1H, s), 8.35(1H, s), 8.43(1H, br).

EXAMPLE 62

8-{4-[2-(Diethylamino)ethoxy]benzylamino}-3-ethyl-2,3-dihydro-1H-imidazo[4,5-g]quinazoline-2-thione.2 hydrochloride (Compound 62)

This compound was synthesized from the compound obtained in Reference Example 63.

$^1$H-NMR (DMSO-$d_6$) δ(ppm): 1.23–1.33(9H, m), 3.15–3.27(4H, m), 3.40–3.50(2H, m), 4.30–4.43(4H, m), 4.89(2H, d, J=5.3 Hz), 6.97(2H, d, J=8.6 Hz), 7.39(2H, d, J=8.6 Hz), 7.76(1H, s), 8.41(1H, s), 8.86(1H, s), 10.78–10.80(2H, m), 13.77(1H, s).

EXAMPLE 63

3-Ethyl-8-[4-(2-piperidinoethoxy)benzylamino]-2,3-dihydro-1H-imidazo[4,5-g]quinazoline-2-thione.2 hydrochloride (Compound 63)

This compound was synthesized from the compound obtained in Reference Example 64.

$^1$H-NMR (DMSO-$d_6$) δ(ppm): 1.31(3H, t, J=7.1 Hz), 1.63–1.90(6H, m), 2.90–3.10(2H, m), 3.30–3.50(4H, m), 4.30–4.45(4H, m), 4.88(2H, d, J=5.0 Hz), 6.97(2H, d, J=8.6 Hz), 7.39(2H, d, J=8.6 Hz), 7.77(1H, s), 8.41(1H, s), 8.86 (1H, s), 10.79(1H, br), 10.91(1H, br), 13.76(1H, s).

EXAMPLE 64

3-Ethyl-8-{4-[2-(4-methylpiperazin-1-yl)ethoxy]benzylamino}-2,3-dihydro-1H-imidazo[4,5-g]quinazoline-2-thione.3 hydrochloride (Compound 64)

This compound was synthesized from the compound obtained in Reference Example 65.

$^1$H-NMR (DMSO-$d_6$) δ(ppm): 1.31(3H, t, J=7.1 Hz), 2.83(3H, s), 3.30–3.65(10H, m), 4.30–4.40(4H, m), 4.89 (2H, d, J=5.3 Hz), 6.99(2H, d, J=8.6 Hz), 7.399(2H, d, J=8.6 Hz), 7.75(1H, s), 8.40(1H, s), 8.86(1H, s), 10.77(1H, br), 13.76(1H, s).

EXAMPLE 65

3-Ethyl-8-{4-[2-(4-ethylpiperazin-1-yl)ethoxy]benzylamino}-2,3-dihydro-1H-imidazo[4,5-g]quinazoline-2-thione.3 hydrochloride (Compound 65)

This compound was synthesized from the compound obtained in Reference Example 66.

$^1$H-NMR (DMSO-$d_6$) δ(ppm): 1.26(3H, t, J=7.3 Hz), 1.30(3H, t, J=7.1 Hz), 3.16–3.76(12H, m), 4.33–4.37(4H, m), 4.89(2H, d, J=5.3 Hz), 6.99(2H, d, J=8.7 Hz), 7.38(2H, d, J=8.7 Hz), 7.72(1H, s), 8.38(1H, s), 8.87(1H, s), 10.73 (1H, t, J=5.3 Hz), 13.77(1H, s).

EXAMPLE 66

3-Ethyl-8-{4-{2-[4-(2-hydroxyethyl)piperazin-1-yl]ethoxy}benzylamino}-2,3-dihydro-1H-imidazo[4,5-g]quinazoline-2-thione.3 hydrochloride (Compound 66)

This compound was synthesized from the compound obtained in Reference Example 67.

$^1$H-NMR (DMSO-$d_6$) δ(ppm): 1.30(3H, t, J=7.1 Hz), 3.24–3.99(14H, m), 4.30–4.38(4H, m), 4.88(2H, d, J=5.6 Hz), 6.99(2H, d, J=8.9 Hz), 7.39(2H, d, J=8.9 Hz), 7.77(1H, s), 8.42(1H, s), 8.86(1H, s), 10.81(1H, t, J=5.6 Hz), 13.79 (1H, s).

EXAMPLE 67

3-Ethyl-8-{4-[2-(1-pyrrolidinyl)ethoxy]benzylamino}-2,3-dihydro-1H-imidazo[4,5-g]quinazoline-2-thione.2 hydrochloride (Compound 67)

This compound was synthesized from the compound obtained in Reference Example 68.

$^1$H-NMR (DMSO-$d_6$) δ(ppm): 1.30(3H, t, J=7.1 Hz), 1.88–2.02(4H, m), 3.06–3.10(2H, m), 3.42–3.50(4H, m), 4.33–4.35(4H, m), 4.88(2H, d, J=5.3 Hz), 6.99(2H, d, J=8.6 Hz), 7.39(2H, d, J=8.6 Hz), 7.76(1H, s), 8.42(1H, s), 8.86 (1H, s), 10.81(1H, br), 11.12(1H, br), 13.79(1H, s).

EXAMPLE 68

8-{4-[3-(Diethylamino)propoxy]benzylamino}-3-ethyl-2,3-dihydro-1H-imidazo[4,5-g]quinazoline-2-thione (Compound 68)

This compound was synthesized from the compound obtained in Reference Example 70.

$^1$H-NMR (DMSO-d$_6$) δ(ppm): 1.16–1.35(9H, m), 2.13–2.15(2H, m), 3.10–3.25(6H, m), 4.04(2H, t, J=5.9 Hz), 4.34(2H, q, J=7.0 Hz), 4.76(2H, t, J=5.6 Hz), 6.90(2H, d, J=8.6 Hz), 7.32(2H, d, J=8.6 Hz), 7.66(1H, s), 8.17(1H, s), 8.54(1H, s), 9.44(1H, br), 10.33(1H, br).

EXAMPLE 69

8-{4-[4-(Diethylamino)butoxy]benzylamino}-3-ethyl-2,3-dihydro-1H-imidazo [4,5-g]quinazoline-2-thione (Compound 69)

This compound was synthesized from the compound obtained in Reference Example 72.

$^1$H-NMR (DMSO-d$_6$) δ(ppm): 1.16–1.30(9H, m), 1.70–1.80(4H, m), 3.01–3.22(6H, m), 3.96(2H, t, J=5.4 Hz), 4.33(2H, q, J=6.9 Hz), 4.70(2H, t, J=5.3 Hz), 6.87(2H, d, J=8.6 Hz), 7.29(2H, d, J=8.6 Hz), 7.61(1H, s), 8.09(1H, s), 8.39(1H, s), 8.92(1H, br), 13.50(1H, br).

EXAMPLE 70

8-{4-[2-(Diethylamino)ethoxy]benzylamino}-3-ethyl-2,3-dihydro-1H-imidazo[4,5-g]quinazolin-2-one (Compound 69)

This compound was synthesized from the compound obtained in Reference Example 63.

$^1$H-NMR (DMSO-d$_6$) δ(ppm): 1.00–1.10(6H, m), 1.25 (3H, t, J=6.9 Hz), 2.65–2.80(4H, m), 3.25–3.40(2H, m), 3.94(2H, q, J=6.9 Hz), 4.09(2H, br), 4.70(2H, t, J=5.3 Hz), 6.88(2H, d, J=8.6 Hz), 7.29(2H, d, J=8.6 Hz), 7.33(1H, s), 7.81(1H, s), 8.33(1H, s), 8.54(1H, t, J=5.3 Hz).

EXAMPLE 71

3-Ethyl-8-[2-(1,2,3,6-tetrahydropyridin-1-ylmethyl)benzylamino]-2,3-dihydro-1H-imidazo[4,5-g]quinazoline-2-thione.2 hydrochloride (Compound 71)

7-Ethylamino-6-nitro-4-[2-(1,2,3,6-tetrahydropyridin-1-ylmethyl)benzylamino]quinazoline (3.80 g, 9.09 mmol) obtained in Reference Example 73 was suspended in ethanol (100 ml) followed by stirring at 80° C. under heating. Reduced iron (1.9 g, 34.0 mmol) and water (3 ml) were added thereto, and anhydrous ferric chloride (catalytic amount) was added to the mixture followed by stirring at the same temperature for 1.5 hours. After the reaction, insoluble matters were filtered off using filtration auxiliary(celite). Triethylamine (8.00 ml, 57.6 mmol) and carbon disulfide (30.0 ml, 499 mmol) were added to the obtained filtrate followed by stirring at room temperature for one night. Carbon disulfide (10.0 ml, 166 mmol) was added and the mixture was stirred at room temperature further for one night. After the reaction, the solution was concentrated under reduced pressure and the residue was purified by silica gel column chromatography (eluent:chloroform/methanol= 100) to give a free base (1.49 g). The obtained free base was suspended in methanol under ice-cooling, and an excess amount of 4N hydrogen chloride/ethyl acetate was added thereto. The solution was concentrated and the residue was crystallized from ethanol/ether followed by drying to give the title compound (1.17 g, 26%).

$^1$H-NMR (DMSO-d$_6$) δ(ppm): 1.31(3H, t, J=7.1 Hz), 2.25–2.50(2H, m), 3.30–3.50(2H, m), 3.74–3.78(2H, m), 4.35(2H, q, J=7.1 Hz), 4.65(2H, s), 5.12(2H, d, J=4.6 Hz), 5.75(1H, d, J=9.9 Hz), 5.96(1H, d, J=9.9 Hz), 7.37–7.45(2H, m), 7.53–7.56(1H, m), 7.76–7.79(2H, m), 8.48(1H, s), 8.88 (1H, s), 10.60–10.90(2H, m), 13.76(1H, s).

EXAMPLE 72

3-Ethyl-8-{2-{4-[2-(2-hydroxyethoxy)ethyl]piperazin-1-ylmethyl}benzylamino)-2,3-dihydro-1H-imidazo[4,5-g]quinazoline-2-thione.3 hydrochloride (Compound 72)

This compound was synthesized from the compound obtained in Reference Example 74.

$^1$H-NMR (DMSO-d$_6$) δ(ppm): 1.32(3H, t, J=7.1 Hz), 3.38–3.87(14H, m), 3.90–4.31(2H, m), 4.36(2H, q, J=7.1 Hz), 4.40–4.70(2H, m), 5.16(2H, d, J=5.0 Hz), 7.37–7.39 (2H, m), 7.52–7.55(1H, m), 7.72–7.76(2H, m), 8.45(1H, s), 8.95(1H, s), 10.82(1H, br), 13.72(1H, s).

EXAMPLE 73

3-Ethyl-8-{2-{4-[(isopropylcarbamoyl)methyl]piperazin-1-ylmethyl}benzylamino}-2,3-dihydro-1H-imidazo[4,5-g]quinazoline-2-thione.3 hydrochloride (Compound 73)

This compound was synthesized from the compound obtained in Reference Example 75.

$^1$H-NMR (DMSO-d$_6$) δ(ppm): 1.11(6H, d, J=6.6 Hz), 1.31(3H, t, J=7.3 Hz), 3.25–3.73(10H, m), 3.75–4.00(2H, m), 4.35(2H, q, J=7.3 Hz), 4.36–4.52(1H, m), 5.15(2H, d, J=4.6 Hz), 7.37–7.42(3H, m), 7.42–7.51(1H, m), 7.68–7.75 (1H, m), 7.76(1H, s), 8.47(1H, s), 8.52–8.55(1H, m), 10.86 (1H, br), 13.75(1H, s).

EXAMPLE 74

3-Ethyl-8-{2-[4-(3,4-methylenedioxybenzyl)piperazin-1-ylmethyl]benzylamino}-2,3-dihydro-1H-imidazo[4,5-g]quinazoline-2-thione.3 hydrochloride (Compound 74)

This compound was synthesized from the compound obtained in Reference Example 76.

$^1$H-NMR (DMSO-d$_6$) δ(ppm): 1.32(3H, t, J=7.1 Hz), 3.28–3.91(10H, m), 4.35(2H, q, J=7.1 Hz), 4.45–4.61(2H, m), 5.15(2H, d, J=3.6 Hz), 6.06(2H, s), 6.93(1H, d, J=7.9 Hz), 7.11–7.14(1H, m), 7.33–7.42(3H, m), 7.51–7.53(1H, m), 7.71–7.74(1H, m), 7.75(1H, s), 8.45(1H, s), 8.94(1H, s), 10.81(1H, s), 13.73(1H, s).

EXAMPLE 75

3-Ethyl-8-{2-[4-(ethoxycarbonyl)piperidin-1-ylmethyl]benzylamino}-2,3-dihydro-1H-imidazo[4,5-g]quinazoline-2-thione.2 hydrochloride (Compound 75)

This compound was synthesized from the compound obtained in Reference Example 77.

$^1$H-NMR (DMSO-d$_6$) δ(ppm): 1.21(3H, t, J=7.1 Hz), 1.31(3H, t, J=7.1 Hz), 2.07–2.25(4H, m), 3.22–3.35(2H, m), 3.37–3.65(3H, m), 4.11(2H, q, J=7.1 Hz), 4.35(2H, q, J=7.1 Hz), 4.56(2H, s), 5.14(2H, d, J=5.3 Hz), 7.35–7.44(2H, m), 7.51–7.57(1H, m), 7.74–7.88(2H, m), 8.46(1H, s), 8.89(1H, s), 10.88(1H, br), 13.75(1H, s).

EXAMPLE 76

3-Ethyl-8-{2-[4-(ethoxycarbonyl)piperidin-1-ylmethyl]benzylamino}-2,3-dihydro-1H-imidazo[4,5-g]quinazolin-2-one.2 hydrochloride (Compound 76)

This compound was synthesized from the compound obtained in Reference Example 77.

¹H-NMR (DMSO-d₆) δ(ppm): 1.20–1.28(6H, m), 2.07–2.30(4H, m), 3.07–3.25(2H, m}, 3.38–3.50(3H, m), 3.94(2H, q, J=7.3 Hz), 4.10(2H, q, J=7.3 Hz), 4.55(2H, s), 5.10(2H, d, J=5.0 Hz), 7.38–7.43(2H, m), 7.51–7.55(2H, m), 7.73–7.77(2H, m), 8.27(1H, s), 8.84(1H, s), 10.74(1H, s), 12.01(1H, s).

EXAMPLE 77

3-Ethyl-8-{2-[4-(2-pyridyl)piperidin-1-ylmethyl]benzylamino}-2,3-dihydro-1H-imidazo[4,5-g]quinazolin-2-one.3 hydrochloride (Compound 77)

This compound was synthesized from the compound obtained in Reference Example 16.

¹H-NMR (DMSO-d₆) δ(ppm): 1.28(3H, t, J=7.2 Hz), 3.44–3.70(4H, m), 3.75–3.98(4H, m), 4.52–4.75(4H, m), 5.14(2H, d, J=5.0 Hz), 7.00(1H, dd, J=6.4 Hz, 6.4 Hz), 7.36–7.44(3H, m), 7.48–7.58(2H, m), 7.86(1H, d, J=6.4 Hz), 7.99(1H, dd, J=7.4 Hz, 8.9 Hz), 8.13(1H, d, J=7.4 Hz), 8.29(1H, s), 8.93(1H, s), 10.81(1H, br), 11.77(1H, br), 11.99(1H, s).

EXAMPLE 78

8-{2-[3-(Diethylamino)propoxy]benzylamino}-3-ethyl-2,3-dihydro-1H-imidazo[4,5-g]quinazolin-2-one.2 hydrochloride (Compound 78)

This compound was synthesized from the compound obtained in Reference Example 62.

¹H-NMR (DMSO-d₆) δ(ppm): 1.21–1.31(9H, m), 2.18–2.23(2H, m), 3.08–3.38(6H, m), 3.95(2H, q, J=6.9 Hz), 4.16(2H, t, J=5.8 Hz), 4.91(2H, d, J=5.3 Hz), 6.90(1H, dd, J=7.3 Hz, 7.3 Hz), 7.03(1H, d, J=8.3 Hz), 7.21–7.29(2H, m), 7.54(1H, s), 8.28(1H, s), 8.83(1H, s), 10.39(1H, br), 10.80 (1H, br), 12.00(1H, s).

EXAMPLE 79

3-Ethyl-8-[3-(3-morpholinopropoxy)benzylamino]-2,3-dihydro-1H-imidazo[4,5-g]quinazoline-2-thione.2 hydrochloride (Compound 79)

This compound was synthesized from the compound obtained in Reference Example 79.

¹H-NMR (DMSO-d₆) δ(ppm): 1.23(3H, t, J=7.1 Hz), 2.10–2.20(2H, m), 2.97–3.16(2H, m), 3.20–3.28(2H, m), 3.38–3.41(2H, m), 3.73–3.99(6H, m), 4.28(2H, q, J=7.1 Hz), 4.85(2H, d, J=5.3 Hz), 6.78–6.83(1H, m), 6.91–6.93(2H, m), 7.20(1H, dd, J=8.0 Hz, 8.2 Hz), 7.67(1H, s), 8.35(1H, s), 8.80(1H, s), 10.73(1H, br), 11.31(1H, br), 13.71(1H, s).

EXAMPLE 80

8-{3-[3-(Diethylamino)propoxy]benzylamino}-3-ethyl-2,3-dihydro-1H-imidazo[4,5-g]quinazoline-2-thione.2 hydrochloride (Compound 80)

This compound was synthesized from the compound obtained in Reference Example 81.

¹H-NMR (DMSO-d₆) δ(ppm): 1.21–1.34(9H, m), 2.09–2.19(2H, m), 3.07–3.20(6H, m), 4.06(2H, t, J=5.9 Hz), 4.35(2H, q, J=6.9 Hz), 4.93(2H, d, J=5.3 Hz), 6.87(1H, d, J=6.9 Hz), 6.99(1H, d, J=7.3 Hz), 7.01(1H, s), 7.27(1H, dd, J=6.9 Hz, 7.3 Hz), 7.75(1H, s), 8.42 (1H, s), 8.86(1H, s), 10.62(1H, br), 10.77(1H, br), 13.76(1H, s).

EXAMPLE 81

3-Ethyl-8-[3-(3-morpholinopropoxy)benzylamino]-2,3-dihydro-1H-imidazo[4,5-g]quinazolin-2-one.2 hydrochloride (Compound 81)

This compound was synthesized from the compound obtained in Reference Example 79.

¹H-NMR (DMSO-d₆) δ(ppm): 1.23(3H, t, J=7.4 Hz), 2.17–2.24(2H, m), 3.05–3.13(2H, m), 3.24–3.42(2H, m), 3.47–3.51(2H, m), 3.88–4.07(8H, m), 4.91(2H, d, J=5.6 Hz), 6.88(1H, d, J=7.6 Hz), 6.98(1H, s), 6.99(1H, d, J=6.6 Hz), 7.28(1H, dd, J=6.6 Hz, 7.6 Hz), 7.48(1H, s), 8.19(1H, s), 8.83(1H, s), 10.55(1H, br), 11.17(1H, br), 12.02(1H, br).

EXAMPLE 82

3-Ethyl-8-[4-(3-morpholinopropoxy)benzylamino]-2,3-dihydro-1H-imidazo[4,5-g]quinazoline-2-thione.2 hydrochloride (Compound 82)

This compound was synthesized from the compound obtained in Reference Example 83.

¹H-NMR (DMSO-d₆) δ(ppm): 1.30(3H, t, J=7.1 Hz), 2.10–2.24(2H, m), 2.80–3.25(6H, m), 3.78–4.00(4H, m), 4.04(2H, t, J=6.1 Hz), 4.35(2H, q, J=7.1 Hz), 4.88(2H, d, J=5.6 Hz), 6.93(2H, d, J=8.6 Hz), 7.36(2H, d, J=8.6 Hz), 7.72(1H, s), 8.37(1H, s), 8.86(1H, s), 10.70(1H, s), 11.40 (1H, s), 13.76(1H, br).

EXAMPLE 83

3-Ethyl-8-[4-(4-morpholinobutoxy)benzylamino]-2,3-dihydro-1H-imidazo[4,5-g]quinazoline-2-thione.2 hydrochloride (Compound 83)

This compound was synthesized from the compound obtained in Reference Example 85.

¹H-NMR (DMSO-d₆) δ(ppm): 1.30(3H, t, J=7.1 Hz), 1.72–1.89(4H, m), 2.96–3.19(6H, m), 3.75–4.00(6H, m), 4.35(2H, q, J=7.1 Hz), 4.88(2H, d, J=5.3 Hz), 6.92(2H, d, J=8.6 Hz), 7.35(2H, d, J=8.6 Hz), 7.72(1H, s), 8.38(1H, s), 8.87(1H, s), 10.79(1H, s), 11.14(1H, s), 13.77(1H, s).

EXAMPLE 84

8-{4-[4-(Diethylamino)butoxy]benzylamino}-3-ethyl-2,3-dihydro-1H-imidazo[4,5-g]quinazoline-2-thione.2 hydrochloride (Compound 84)

This compound was synthesized from the compound obtained in Reference Example 87.

¹H-NMR (DMSO-d₆) δ(ppm): 1.15–1.32(9H, m), 1.65–1.90(4H, m), 2.98–3.15(6H, m), 3.97(2H, t, J=6.3 Hz), 4.35(2H, q, J=7.3 Hz), 4.87(2H, d, J=5.6 Hz), 6.91(2H, d, J=8.6 Hz), 7.34(2H, d, J=8.6 Hz), 7.76(1H, s), 8.41(1H, s), 8.85(1H, s), 10.48(1H, s), 10.75(1H, br), 13.76(1H, s).

EXAMPLE 85

3-Ethyl-8-[2-(4-ethylpiperazin-1-ylmethyl)benzylamino}-2,3-dihydro-1H-imidazo[4,5-g]quinazolin-2-one.3 hydrochloride (Compound 85)

This compound was synthesized from the compound obtained in Reference Example 53.

¹H-NMR (DMSO-d₆) δ(ppm): 1.26–1.35(6H, m), 3.19–3.30(2H, br), 3.40–4.05(12H, m), 5.13(2H, d, J=5.0 Hz), 7.37–7.43(2H, m), 7.50–7.56(2H, m), 7.75(1H, s), 8.25(1H, s), 8.90(1H, s), 10.65(1H, s), 11.99(1H, s).

EXAMPLE 86

3-Ethyl-8-[3-(2-morpholinoethoxy)benzylamino]-2,3-dihydro-1H-imidazo[4,5-g]quinazolin-2-one (Compound 86)

This compound was synthesized from the compound obtained in Reference Example 44.

¹H-NMR (DMSO-d₆) δ(ppm): 1.27(3H, t, J=7.2 Hz), 2.41–2.50(4H, m), 2.65(2H, t, J=5.9 Hz), 3.53–3.57(4H, m), 3.92(2H, q, J=7.2 Hz), 4.03(2H, t, J=5.9 Hz), 4.74(2H, d, J=5.9 Hz), 6.78(1H, d, J=6.4 Hz), 6.90(1H, s), 6.92(1H, d, J=6.9 Hz), 7.19(1H, dd, J=6.4 Hz, 6.9 Hz), 7.32(1H, s), 7.82(1H, s), 8.32(1H, s), 8.52(1H, t, J=5.9 Hz), 11.37(1H, s).

EXAMPLE 87

3-Ethyl-8-[3-(2-piperidinoethoxy)benzylamino]-2,3-dihydro-1H-imidazo[4,5-g]quinazolin-2-one.2 hydrochloride (Compound 87)

This compound was synthesized from the compound obtained in Reference Example 45.

¹H-NMR (DMSO-d₆) δ(ppm): 1.29(3H, t, J=7.2 Hz), 1.68–2.00(6H, m), 2.90–3.10(2H, m), 3.20–3.50(4H, m), 3.94(2H, q, J=7.2 Hz), 4.41–4.45(2H, m), 4.91(2H, d, J=5.4 Hz), 6.90(1H, d, J=8.4 Hz), 7.01–7.06(2H, m), 7.28(1H, dd, J=7.9 Hz, 8.4 Hz), 7.54(1H, s), 8.25(1H, s), 8.80(1H, s), 10.65(1H, t, J=5.4 Hz), 12.00(1H, s).

EXAMPLE 88

8-{3-[3-(Diethylamino)propoxy]benzylamino}-3-ethyl-2,3-dihydro-1H-imidazo[4,5-g]quinazolin-2-one.2 hydrochloride (Compound 88)

This compound was synthesized from the compound obtained in Reference Example 81.

¹H-NMR (DMSO-d₆) δ(ppm): 1.19–1.31(9H, m), 2.09–2.20(2H, m), 3.07–3.20(6H, m), 3.94(2H, q, J=7.4 Hz), 4.06(2H, t, J=6.2 Hz), 4.90(2H, d, J=5.9 Hz), 6.87(1H, d, J=6.9 Hz), 6.98(1H, d, J=6.4 Hz), 6.99(1H, s), 7.26(1H, dd, J=6.4 Hz, 6.9 Hz), 7.52(1H, s), 8.22(1H, s), 8.80(1H, s), 10.56–10.65(2H, m), 12.00(1H, s).

EXAMPLE 89

8-{2-[(Dimethylamino)methyl]benzylamino}-3-ethyl-2,3-dihydro-1H-imidazo[4,5-g]quinazoline-2-thione.2 hydrochloride (Compound 89)

This compound was synthesized from the compound obtained in Reference Example 88.

¹H-NMR (DMSO-d₆) δ(ppm): 1.32(3H, t, J=6.9 Hz), 2.85(3H, s), 2.86(3H, s), 4.36(2H, q, J=6.9 Hz), 4.60(2H, s), 5.13(2H, d, J=5.4 Hz), 7.35–7.44(2H, m), 7.52–7.56(1H, m), 7.67–7.73(1H, m), 7.79(1H, s), 8.47(1H, s), 8.88(1H, s), 10.77(1H, br), 10.87(1H, br), 13.73(1H, s).

Industrial Applicability

According to the present invention, there can be provided imidazoquinazoline derivatives or pharmaceutically acceptable salts thereof which have the strong and selective cGMP-specific PDE inhibitory activity and are useful for treating or ameliorating cardiovascular diseases such as thrombosis, angina pectoris, hypertension, heart failure, arterial sclerosis, as well as asthma and the like.

We claim:

1. An imidazoquinazoline derivative represented by formula (I):

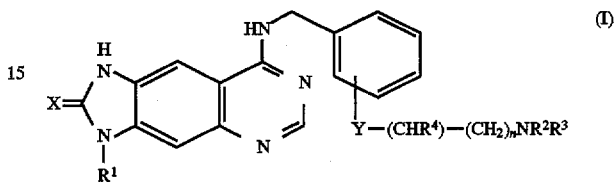

wherein $R^1$ represents hydrogen, substituted or unsubstituted lower alkyl, cycloalkyl, lower alkenyl, substituted or unsubstituted aralkyl, substituted or unsubstituted aryl, substituted or unsubstituted heteroarylalkyl, or substituted or unsubstituted heteroaryl, $R^2$ and $R^3$ represent independently hydrogen, substituted or unsubstituted lower alkyl, substituted or unsubstituted aralkyl, substituted or unsubstituted aryl, substituted or unsubstituted heteroarylalkyl, or substituted or unsubstituted heteroaryl, or $R^2$ and $R^3$ are combined to represent a substituted or unsubstituted heterocyclic group containing a nitrogen atom, $R^4$ represents hydrogen or substituted or unsubstituted lower alkyl, X represents O or S, Y represents a single bond or O, n represents 0, 1, 2, or 3, or a pharmaceutically acceptable salt thereof.

2. An imidazoquinazoline derivative or a pharmaceutically acceptable salt thereof according to claim 1, wherein $R^1$ represents substituted or unsubstituted lower alkyl.

3. An imidazoquinazoline derivative or a pharmaceutically acceptable salt thereof according to claim 1 or 2, wherein $R^2$ and $R^3$ are combined to represent a substituted or unsubstituted heterocyclic group containing a nitrogen atom.

4. A pharmaceutical composition containing an imidazoquinazoline derivative or a pharmaceutically acceptable salt thereof according to any of claims 1 to 2.

5. A pharmaceutical composition containing an imidazoquinazoline derivative or a pharmaceutically acceptable salt thereof according to claim 3.

* * * * *

UNITED STATES PATENT AND TRADEMARK OFFICE
CERTIFICATE OF CORRECTION

PATENT NO. : 5,698,560
DATED : December 16, 1997
INVENTOR(S) : YASUO ONODA ET AL.

It is certified that error appears in the above-identified patent and that said Letters Patent is hereby corrected as shown below:

ON THE TITLE PAGE AT [56] References Cited
  FOREIGN PATENT DOCUMENTS, Insert: --WO 06648  3/1995  PCT--.

COLUMN 1
  Line 3, "PCT/JP96/60497," should read --PCT/JP96/00497,--.

COLUMN 4
  Line 12, "Then," should read --Now--.

COLUMN 8
  Line 6, "thiocarbenyldiimidazole," should read
     --thiocarbonyldiimidazole,--.

COLUMN 20
  Line 67, "8.74(1H, br)." should read --8.74(1H, s), 11.9-
     12.2(1H, br).--.

COLUMN 22
  Line 39, "aluminium" should read --aluminum--.

COLUMN 23
  Line 66, "[2(hydroxymethyl)" should read --[2-
     (hydroxymethyl)--

COLUMN 24
  Line 28, "2,32-2.62" should read --2.32-2.62--.

COLUMN 25
  Line 47, "was" should read --were--.

UNITED STATES PATENT AND TRADEMARK OFFICE
CERTIFICATE OF CORRECTION

PATENT NO. : 5,698,560
DATED : December 16, 1997
INVENTOR(S): YASUO ONODA ET AL.

It is certified that error appears in the above-identified patent and that said Letters Patent is hereby corrected as shown below:

COLUMN 26
  Line 23, "7-ethylamino-[4-" should read --7-ethylamino-4-[4---;
  Line 41, "$^1$NMR" should read --$^1$H-NMR--;
  Line 52, "7-ethylamino-[4-" should read --7-ethylamino-4-[4---.

COLUMN 27
  Line 5, "aluminium" should read --aluminum--;
  Line 53, "2,34 mmol)" should read --2.43 mmol)--.

COLUMN 29
  Line 42, "2,31" should read --2.31--.

COLUMN 30
  Line 9, "was" should read --were--;
  Line 20, "aluminium" should read --aluminum--;
  Line 40, "$^1$H-NMR-(CDCl$_3$)" should read --$^1$H-NMR (CDCl$_3$)--.

COLUMN 31
  Line 30, "aluminium" should read --aluminum--.

COLUMN 33
  Line 12, "-6nitroquinazoline" should read ---6-nitroquinazoline--;
  Line 14, "-[4-" should read ---4-[4---;
  Line 28, "-[2-" should read ---4-[2---;
  Line 30, "$^1$H-NM$_{(CDCl3)}$)" should read --$^1$H-NMR(CDCl$_3$)--.

UNITED STATES PATENT AND TRADEMARK OFFICE
CERTIFICATE OF CORRECTION

PATENT NO.  : 5,698,560

DATED       : December 16, 1997

INVENTOR(S) : YASUO ONODA ET AL.

It is certified that error appears in the above-identified patent and that said Letters Patent is hereby corrected as shown below:

COLUMN 34
   Line 1, "$^1$H-NMR" should read --¶ $^1$H-NMR--;
   Line 2, "8(ppm):" should read --δ(ppm):--;
   Line 31, "1-methylhomopiperazineo" should read --1-methylhomopiperazine--.

COLUMN 35
   Line 34, "minium" should read --minum--.

COLUMN 36
   Line 2, "aluminium" should read --aluminum--.

COLUMN 37
   Line 46, "aluminium" should read --aluminum--.

COLUMN 38
   Line 6, "aluminium" should read --aluminum--.

COLUMN 39
   Line 8, "Examples 75" should read --Example 75--;
   Line 34, "7-ethylamino-[2-" should read --7-ethylamino-4-[2---;
   Line 41, "J=2,3 Hz," should read --J=2.3 Hz,--.

COLUMN 40
   Line 23, Close up right margin;
   Line 25, "aluminium" should read --aluminum--;
   Line 50, "J=2,3 Hz," should read --J=2.3 Hz,--.

UNITED STATES PATENT AND TRADEMARK OFFICE
CERTIFICATE OF CORRECTION

PATENT NO.  :  5,698,560

DATED       :  December 16, 1997

INVENTOR(S):  YASUO ONODA ET AL.

It is certified that error appears in the above-identified patent and that said Letters Patent is hereby corrected as shown below:

COLUMN 41
  Line 1, "aluminium" should read --aluminum--;
  Line 28, "aluminium" should read --aluminum--;
  Line 58, "aluminium" should read --aluminum--.

COLUMN 42
  Line 19, "aluminium" should read --aluminum--.
  Line 50, Close up right margin.

COLUMN 45
  Line 36, "3Ethyl-" should read --3-Ethyl---;

COLUMN 49
  Line 4, "1.50-11.80" should read --11.50-11.80--.

COLUMN 50
  Line 22, "3.77" should read --13.77--.

UNITED STATES PATENT AND TRADEMARK OFFICE
CERTIFICATE OF CORRECTION

PATENT NO.   : 5,698,560

DATED        : December 16, 1997

INVENTOR(S): YASUO ONODA ET AL.

It is certified that error appears in the above-identified patent and that said Letters Patent is hereby corrected as shown below:

COLUMN 62
  Line 44, "any of claims 1 to 2." should read --claim 1 or 2.--.

Signed and Sealed this

Twenty-eighth Day of July, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,698,560

DATED : December 16, 1997

INVENTOR(S) : YASUO ONODA ET AL.

It is certified that error appears in the above-identified patent and that said Letters Patent is hereby corrected as shown below:

COLUMN 34

Line 41, "1-methylhomopiperazineo" should read --1-methylhomopiperazine.--

Signed and Sealed this

Seventeenth Day of November, 1998

Attest:

BRUCE LEHMAN

Attesting Officer        Commissioner of Patents and Trademarks